US 7,429,481 B2
United States Patent
Bergman et al.

(10) Patent No.: US 7,429,481 B2
(45) Date of Patent: Sep. 30, 2008

(54) TARGETING VIRUSES USING A MODIFIED SINDBIS GLYCOPROTEIN

(75) Inventors: Ira Bergman, Pittsburgh, PA (US); Patricia Whitaker-Dowling, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 79 days.

(21) Appl. No.: 11/227,778

(22) Filed: Sep. 14, 2005

(65) Prior Publication Data

US 2006/0127981 A1   Jun. 15, 2006

Related U.S. Application Data

(60) Provisional application No. 60/614,791, filed on Sep. 30, 2004, provisional application No. 60/609,573, filed on Sep. 14, 2004.

(51) Int. Cl.
C12N 1/68 (2006.01)
C12N 15/00 (2006.01)

(52) U.S. Cl. .................................. 435/320.1; 435/69.1
(58) Field of Classification Search ............... 435/320.1
See application file for complete search history.

(56) References Cited

U.S. PATENT DOCUMENTS

| | | | |
|---|---|---|---|
| 6,432,699 B1 * | 8/2002 | Meruelo et al. ........... | 435/320.1 |
| 6,596,268 B1 * | 7/2003 | Coffey et al. .............. | 424/93.2 |
| 6,649,157 B2 * | 11/2003 | Coffey et al. .............. | 424/93.1 |
| 2002/0192824 A1 * | 12/2002 | Meruelo et al. ............. | 435/456 |
| 2003/0049845 A1 * | 3/2003 | Meruelo et al. ............. | 435/456 |

OTHER PUBLICATIONS

Paul et al. AIDS Research and Human Retroviruses, 1993, vol. 9, No. 10. pp. 963-970.*
Schubert et a. J. Virol. 1992, vol. 66, No. 33, pp. 1579-1589.*
Somia et al., Proc. Natl. Acad. Sci. USA, 1995, vol. 92, pp. 75570-7574.*
Davis et al., 2006, Structural polyprotein [contains: Spike glycoprotein E2]. GenBank Accession No. P11259.
Lindencrona, J. A. et al., CD4+ T cell-mediated HER-2/neu-specific tumor rejection in the absence of B cells. International Journal of Cancer 109: 259-264.
Miller, M. A., C. L. Lavine, S. D. Klas, L. M. Pfeffer, and M. A. Whitt, 2004, Recombinant replication-restricted VSV as an expression vector for murine cytokines. Protein Expression & Purification 33: 92-103.
Aichele et al., 2003, Macrophages of the splenic marginal zone are essential for trapping of blood-borne particulate antigen but dispensable for induction of specific T cell responses. J Immunol. 171(3):1148-55.
Bander, N.H. et al., 2003, Targeted systemic therapy of prostate cancer with a monoclonal antibody to prostate-specific membrane antigen. Semin Oncol. 30: 667-676.

Bergman, I. et al., 2003, Vesicular stomatitis virus. expressing a chimeric Sindbis glycoprotein containing an Fc antibody binding domain targets to Her2/neu overexpressing breast cancer cells. Virology 316: 337-347.
Bucheit, A.D. et al., 2003, An oncolytic measles virus engineered to enter cells through the CD20 antigen. Mol. Ther. 7: 62-72.
Cohen, R.B., 2003, Epidermal growth factor receptor as a therapeutic target in colorectal cancer. Clin Colorectal Cancer. 2: 246-251.
Ercolini, A. M. et al., 2003, Identification and characterization of the immunodominant rat HER-2/neu 1\1HC class I epitope presented by spontaneous mammary tumors from HER-2/neu-transgenic mice. Journal of Immunology 170 :4273-4280.
Martin, F. et al., 2003, Targeted retroviral infection of tumor cells by receptor cooperation. J. Virol. 77: 2753-2756.
Nemunaitis, J. et al., 2003, Pilot trial of intravenous infusion of a replication-selective adenovirus (Onyx-015) in combination with chemotherapy or IL-2 treatment in refractory cancer patients. Cancer Gene Therapy 10: 341-352.
Peng, K.W., et al., 2003, Oncolytic measles viruses displaying a single-chain antibody against CD38, a myeloma cell marker. Blood 101: 2557-2562.
Stojdl, D. F., et al., 2003, VSV strains with defects in their ability to shutdown innate immunity are potent systemic anti-cancer agents. Cancer Cell 4: 263-275.
Wannesson, L. and Ghielmini, M., 2003, Overview of Antibody Therapy in BCell Non-Hodgkin's Lymphoma. Clin Lymphoma. 4 Suppl 1: S5-S12.
Aarts, W. M. et al., 2002, Vector-based vaccinelcytokine combination therapy to enhance induction of immune responses to a self-antigen and antitumor activity. Cancer Res. 62: 5770-5777.
Ali, S. A., et al., 2002, Tumor regression induced by intratumor therpy with a disabled infectious single cycle (DISC) herpes simplex virus (HSV) vector, DISC/HSV/murine granulocyte-macrophage colony-stimulating factor, correlates with antigen-specific adaptive immunity. Journal of Immunology 168:3512-3519.
Buteau, C. et al., 2002, Challenges in the development of effective peptide vaccines for cancer. [Review] [90 refs]. Mayo Clinic Proceedings 77: 339-349.
Chew, H. K., 2002, Medical management of breast cancer: today and tomorrow. [Review] [75 refs]. Cancer Biotherapy & Radiopharmaceuticals 17: 137-149.
Fernandez, M. et al., 2002, Genetically engineered vesicular stomatitis virus in gene therapy: application for treatment of malignant disease. Journal of Virology 76: 895-904.
Hindle, W., 2002, Breast cancer: introduction. [Review] [33 refs]. Clinical Obstetrics & Gynecology 45: 738-745.

(Continued)

Primary Examiner—Bruce Campell
Assistant Examiner—Bao Qun Li
(74) Attorney, Agent, or Firm—Baker Botts L.L.P.

(57) ABSTRACT

The present invention relates to viruses that are engineered to contain a surface ligand molecule which targets the virus to a cell of interest. In particular non-limiting embodiments, the cell of interest is desirably ablated and may be a cancer cell, an infected cell, a cell exhibiting a non-malignant proliferative disorder, or a cell of the immune system. Alternatively, the cell of interest is a target for gene therapy.

7 Claims, 12 Drawing Sheets

OTHER PUBLICATIONS

Hu, H. M. et al., 2002, CD28, TNF receptor, and IL-12 are critical for CD4-independent cross-priming of therapeutic antitumor CD8+ T cells. Journal of Immunology 169: 4897-4904.

Mami-Chouaib, F. et al., 2002, Antitumor cytotoxic T-lymphocyte response in human lung carcinoma: identification of a tumor-associated antigen. Immunol Rev. 188: 114-121.

Miller, G. et al., 2002, Endogenous granulocyte-macrophage colony-stimulating factor overexpression in vivo results in the long-term recruitment of a distinct dendritic cell population with enhanced immunostimulatory function. Journal of Immunology 169: 2875-2885.

Mwangi, W., et al., 2002, DNA-encoded fetal liver tyrosine kinase 3 ligand and granulocyte macrophage-colony stimulating factor increase dendritic cell recruitment to the inoculation site and enhance antigen-specific CD4+. T cell responses induced by DNA vaccination of outbred animals. Journal of Immunology 169: 3837-3846.

Perez-Diez, A. et al., 2002, Intensity of the vaccine elicited immune response determines tumor clearance. Journal of Immunology 168: 338-347.

Pu, Z., et al., 2002, Distinct recognition by two subsets of T cells of an MHC class peptide complex. Proceedings of the National Academy of Sciences of the United States of America 99: 8844-8849.

Ring, C. J., 2002, Cytolytic viruses as potential anti-cancer agents. [Review] [159 refs]. Journal of General Virology 83: 491-502.

Stern, B. V. et al., 2002, Vaccination with tumor peptide in CpG adjuvant protects via IFN-gamma-dependent CD4 cell immunity. Journal of Immunology 168: 6099-6105.

Vogel, C. L. et al., 2002, Efficacy and safety of trastuzumab as a single agent in first-line treatment of HER2-overexpressing metastatic breast cancer. Journal of Clinical Oncology 20: 719-726.

Yamazaki, M. et al., 2002, Effective gene therapy for medullary thyroid carcinoma using recombinant adenovirus inducing tumor-specific expression of interleukin-12. Gene Therapy 9: 64-74.

Yang, Y. A. et al., 2002, Life~ime exposure to a soluble TGF-beta antagonist protects mice against metastasis without adverse side effects.[comment]. Journal of Clinical Investigation 109: 1607-1615.

Zhang, W. et al., 2002, Placement of the structural proteins in Sindbis virus. J Virol. 76: 11645-11658.

Balachandran, S., M. Porosnicu, and G. N. Barber, 2001, Oncolytic activity of vesicular stomatitis virus is effective against tumors exhibiting aberrant p53, Ras, or myc function and involves the induction of apoptosis. Journal of Virology 75: 3474-3479.

Baselga, J. and Albanell, J., 2001, Mechanism of action of anti-HER2 monoclonal antibodies. Ann Oncol. 12 Suppl 1: S35-41.

Beatty, G. and Y. Paterson, 2001, IFN-gamma-dependent inhibition of tumor angiogenesis by tumor angiogenesis by tumor-infiltrating CD4+ T cells requires tumor responsiveness to IFN-gamma. Journal of Immunology 166: 2276-2282.

Bergman, I. et al., 2001, Treatment of meningeal breast cancer xenografts in the rat using an anti-p185/HER2 antibody. Clin. Cancer Res. 7: 2050-2056.

Chu E and DeVita, V.T., 2001, Principles of Cancer Management: Chemotherapy, p. 289-306. In H. S. R. S. DeVita VT Jr. (ed.), Cancer: Principles and Practice of Oncology. Lippincott, Williams & Wikins, Philadelphia.

Danova, M., Porta, C., Ferrari, S., and Riccardi, A., 2001, Strategies of medical treatment for metastatic breast cancer (Review). [Review] [64 refs]. International Journal of Oncology 19: 733-739.

de Mattos CA, de Mattos CC, and Rupprecht CE. 2001. Rhabdoviruses, pp. 1245-1277. In Fundamental Virology, (D. Knipe et al (eds.)); Lippincott Williams & Wilkins, Philadelphia.

Elzey, B. D et al., 2001, Immunization with type 5 adenovirus recombinant for a tumor antigen in combination with recombinant canarypox virus (AL V AC) cytokine gene delivery induces destruction of established prostate tumors. International Journal of Cancer 94: 842-849.

Griffith, T. S. et al., 2001, Inhibition of murine prostate tumor growth and activation of immunoregulatory cells with recombinant canarypox viruses. J. Natl. Cancer Inst. 93: 998-1007.

Gunn, G. R., et al., 2001, Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16. Journal of Immunology 167: 6471-6479.

Hammond, A. L. et al., 2001, Single-chain antibody displayed on a recombinant measles virus confers entry through the tumor-associated carcino embryonic antigen. J. Virol. 75: 2087-2096.

Igarashi, T et al., 2001, Re-treatment of relapsed indolent B-cell lymphoma with rituximab. International Journal of Hematology 73: 13-221.

Khare, P.D., Shao-Xi, L., Kuroki, M., Hirose, Y., Arakawa, F., Nakamura, K., Tomita, Y., Kuroki, M., 2001. Specifically targeted killing of carcinoembryonic antigen (CEA)-expressing cells by a retroviral vector displaying single-chain variable fragmented antibody to CEA and carrying the gene for inducible nitric oxide synthase. Cancer Res. 61, 370-375.

Lamikanra, A., Z. K. Pan, S. N. Isaacs, T. C. Wu, and Y. Paterson. 2001. Regression of established human papillomavirus type 16 (HPV-16) immortalized tumors in vivo by vaccinia viruses expressing different forms of HPV-16 E7 correlates with enhanced CD8(+) T-cell responses that home to the tumor site. Journal of Virology 75:9654-9664.

Lipsky PE and DiamondB. 2001. Autoimmunity and autoimmune diseases, p. 1839-1843. In Brauwald E. Fauci AS, Isselbacher KJ, Kasper DL, Hauser SL, Longo DL, and Jameson JL (eds.), Harrison's principles of internal medicine. McGraw-Hill, New York.

Morizono, K., Bristol, G., Xie, Y.M., Kung, S.K., Chen, I.S., 2001. Antibody-directed targeting of retroviral vectors via cell surface antigens. J. Virol. 75, 8016-8020.

Phan, G. Q., P. Attia, S. M. Steinberg, D. E. White, and S. A. Rosenberg. 2001. Factors associated with response to high-dose interleukin-2 in patients with metastatic melanoma. J. Clin. Oncol. 19:3477-3482.

Pilon, S. A., M. P.Piechocki, and W.Z. Wei. 2001. Vaccination with cytoplasmic ErbB-2 DNA protects mice from mammary tumor growth without anti-ErbB-2 antibody. Journal of Immunology 167:3201-3206.

Putzer, B. M., Stiewe, F. Rodicker, O~ScWldgen, S. Ruhm, O. Dirsch M. Fiedler, U. Damen, B. Tennant, C. Scherer, F. L. Graham, and M. Roggendorf. 2001. Large nontransplanted hepatocellular carcinoma in woodchucks: treatment with adenovirus-mediated delivery of interleukiri 121B7.1 genes. J. NatL Cancer Inst. 93:472-479.

Quinones-Kochs, M. I., M. J. Schenell, L. Buonocore, and J. K. Rose. 2001. Mechanisms of loss of foreign gene expression in recombinant vesicular stomatitis viruses. Virology 287:427-435.

Reilly, R. T., J. P. Machiels, L. A. Emens, A. M. Ercolini, F. I. Okoye, R. Y. Lei, D. Weintraub, and E. M. Jaffee. 2001. The collaboration of both humoral and cellular HER-2/neu targeted immune responses is required for the complete eradication of HER-2/neu-expressing tumors. Cancer Res. 61:880-883.

Rose, J.K., Whitt, M.A., 2001. Rhabdoviridae: the viruses and their replication. In Knipe, D., Howley, P. (Eds.), Fundamental Virology. Lippincott Williams & Wilkins, Philadelphia, pp. 1221-1244.

Shankaran, V., H. Ikeda, A. T. Bruce, J. M. White, P. E. Swanson, L. J. Old, and R. D. Schreiber. 2001. IFNgamma and lymphocytes prevent tumour development and shape tumour immunogenicity. Nature 410:1107-1111.

Slamon, D. J., Leyland-Jones, B., Shak, S., Fuchs, H., Paton, V., Bajamonde, A., Fleming, T., Eirmann, W., Wolter, J., Pegram, M., Baselga, J., and Norton, L. 2001. Use of chemotherapy plus a monoclonal antibody against HER2 for metastatic breast cancer that overexpreses HER2.[comment]. New England Journal of Medicine 344, 783-792.

Tyler, KL. and Nathanson, N. (2001). Pathogenesis of Viral Infections. In "Fundamental Virology" (D. Knipe and P. Howley, Eds.), pp. 199-244. Lipincott Williams & Wilkins, Philadelphia.

Wildner, O., 2001. Oncolytic viruses as therapeutic agents. Ann. Med. 33, 291-304.

Wu, J. T., Byrne, H. M., Kirn, D. H., and Wein, L. M. 2001. Modeling and analysis of a virus that replicates selectively in tumor cells. Bulletin of Mathematical Biology 63, 731-768.

Zelazny, E., B. Li, A. M. Anagnostopoulos, A. Coleman, and A. S. Perkins. 2001. Cooperating oncogenic events in murine mammary tumorigenesis: assessment of ErbB2, mutant p53, and mouse mammary tumor virus. . Experimental & Molecular Pathology 70: 183-193.

Zhou, H., W. D. Chen, X. Qin, K. Lee, L. Liu, S. D. Markowitz, and S. L. Gerson. 2001. MMTV promoter hypomethylation is linked to spontaneous and MNU associated c-neu expression and mammary carcinogenesis in MMTV c-neu transgenic mice, Oncogene 20:6009-6017.

Zwiebel, J.A., 2001. Cancer gene and oncolytic virus therapy. Semin. Oncol. 28, 336-343.

Amici, A., A. Smorlesi, G. Noce, G. Santoni, P. Cappelletti, L. Capparuccia, R. Coppari, R. Lucciarini, C. Petrelli, and M. Provincialli. 2000. DNA vaccination with full-length or truncated neu protective immunity against the developlment odf spontaneous mammary tumors in HER-2/neu transgenic mice. Gene Therapy 7:703-706.

Balachandran, S. and Barber, G. N. 2000. Vesicular stomatitis virus (VSV) therapy of tumors. Iubmb Life 50, 135-138.

Balachandran, S., Roberts, P. C., Kipperman, T., Bhalla,K. N., Compans, R. W., Archer, D. R., and Barber, G. N. 2000. Alpha/beta interferons potentiate virus-induced apoptosis through activation of the FADD/Caspase-8 death signaling pathway. Journal of Virology 74, 1513-1523.

Bergman, I., P. H. Basse, M. A. Barmada, J. A. Griffin, and N. K. Cheung. 2000. Comparison of in vitro antibody-targeted cytotoxicity using mouse, rat and human effectors. Cancer Immunology & Immunotherapy 49:259-266.

Bussfeld, D., M. Nain, P. Hofmann, D. Gemsa, and H. Sprenger. 2000. Selective induction of the monocyte attracting chemokines MCP-1 and IP-10 in vesicular stomatitis virus-infected human monocytes. Journal of Interferon & Cytokine Research 20:615-621.

Chiari, R., Hames, G., Stroobant, V., Texier, C., Maillere, B., Boon, T., Coulie, P.G. 2000. Identification of a tumor-specific shared antigen derived from an Eph receptor and presented to CD4 T cells on HLA class II molecules. Cancer Res. 60:4855-4863.

Kim, S. H., J. F. Carew, D. A. Kooby, J. Shields, C. Entwisle, S. Patel, J. P. Shah, and Y. Fong. 2000. Combination gene therapy using multiple immunomodulatory genes transferred by a defective infectious single cycle herpes virus in squamous cell cancer. Cancer Gene Therapy 7:1279-1285.

Parker, J. N., G. Y. Gillespie, C. E. Love, S. Randall, R. J. Whitley, and J. M. Market. 2000. Engineered herpes simplex virus expressing IL-12 in the treatment of experimental murine brain tumors. Proc. Natl Acad Sci USA 97:2208-2213.

Phinney, B.S., Blackburn, K., Brown, D.T., 2000. The surface conformation of Sindbis virus glycoproteins E1 and E2 at neutral and low pH, as determined by mass spectrometry-based mapping. J. Virol. 74, 646 5667-5678.

Reilly, R. T., Gottlieb, M. B., Ercolini, A. M., Machiels, J. P., Kane, C. E., Okoye, F. I., Muller, W. J., Dixon, K. H., and Jaffee, E. M. 2000. HER-2/neu is a tumor rejection target in tolerized HER-2/neu transgenic mice. Cancer Research 60, 3569-3576.

Stojdl, D. F., Lichty, B., Knowles, S., Marius, R., Atkins, H., Sonenberg, N., and Bell, J. C. 2000. Exploiting tumor-specific defects in the interferon pathway with a previously unknown oncolytic virus. Nature Medicine 6, 821-825.

Tsuboi, A., Oka, Y., Ogawa, H., Elisseeva, O.A., Li, H., Kawasaki, K., Aozasa, K., Kishimoto, T., Udaka, K., Sugiyama, H. 2000. Cytotoxic T-lymphocyte responses elicited to Wilms' tumor gene WT1 product by DNA vaccination. J Clin Immunol. 20:195-202.

Bergman, I., Barmada, M. A., Heller, G., Griffin, J. A., and Cheung, N. K. 1999. Treatment of neoplastic menigeal xenografts by intraventricular administration of an antiganglioside monoclonal antibody, 3F8. International Journal of Cancer 82, 538-548.

Bergman, I., C. R. PoW, R. Venkataramanan, G. J. Burckart, M. Stabin, M. A. Barmada, J. A. Grifrm, and N. K. Cheung. 1999. Intrathecal administration of an anti-ganglioside antibody results in specific accumulation with meningeal neoplastic xenografts in nude rats. Journal of Immunotherapy. 22: 114-123.

Chan, R., Muller, W. J., and Siegel, P. M. 1999. Oncogenic activating mutations in the neu/erbB-2 oncogene are involved in the induction of mammary tumors. [Review] [34 refs]. Annals of the New York Academy of Sciences 889, 45-51.

Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J. 1999. Multinational study of the effecacy and safety of humanized anti-HER2 monoclonal antibody in women who have HER2-overexpressing metastatic breast cancer that has progressed after chemotherapy for metastatic disease. Journal of Clinical Oncology 17, 2639-2648.

Heise, C.. C., A. M; Williams, S. Xue, Mi Propst; and'D. H. Kirn; 1999. Intravenous administration of ONYX-015, a selectively replicating adenovirus, induces antitumoral efficacy. Cancer Res. 59:2623-2628.

Kahn, J. S., Schnell, M. J., Buonocore, L., and Rose, J. K. 1999. Recombinant vesicular stomatitis virus expressing respiratory syncytial virus (RSV) glycoproteins: RSV fusion protein can mediate infection and cell fusion. Virology 254, 81-91.

Penichet, M. L., P. M. Challita, S. U. SWn, S. L. Sampogna, J. D. Rosenblatt, Morrison, and SL. 1999. In vivo properties of three human HER2/neu-expressing murine cell lines in immunocompetent mice. Laboratory Animal Science 49: 179-188.

Toda, M., S. D. Rabkin, H. Kojima, and R. L. Martuza. 1999. Herpes simplex virus as an in situ cancer vaccine for the induction of specific anti-tumor immunity. Human Gene Therapy 10:385-393.

Wang, R.F., Wang, X., Atwood, A.C., Topalian, S.L., Rosenberg, S.A. 1999. Clonin genes encoding MHC class II-restricted antigens: mutated CDC27 as a tumor antigen. Science. 284:1351-1354.

Bergman, I., G. J. Burckart, C. R. PoW, R. Venkataramanan, M. A. Barmada, J. A. Griffin, and N. K. . Cheung. 1998. Pharmacokinetics of IgG anti-ganglioside antibodies in rats and monkeys after intrathecal administration. Journal of Pharmacology & Experimental Therapeutics 284: 111-115.

Jager, E., Chen, Y.T., Drijfhout, J.W., Karbach, J., Ringhoffer, M., Jager, D., Arand, M., Wada, H., Noguchi, Y., Stockert, E., Old, L.J., Knuth, A. 1998. Simultaneous humoral and cellular immune response against cancer-testis antigen NY-ESO-1: definition of human histocompatibility leukocyte antigen (HLA)-A2-binding peptide epitopes. J Exp Med. 187:265-270.

Jiang, A., Chu, T.H., Nocken, F., Cichutek, K., Dornburg, R., 1998. Cell-type-specific gene transfer into human cells with retroviral vectors that display single-chain antibodies. J. Virol. 72, 10148-10156.

Kawakami, Y., Robbins, P.F., Wang, X., Tupesis, J.P., Parkhurst, M.R., Kang, X., Sakaguchi, K., Appella, E., Rosenberg, S.A. 1998. Identification of new melanoma epitopes on melanosomal proteins recognized by tumor infiltrating T lymphocytes restricted by HLA-A1,-A2, and -A3 alleles. J Immunol. 161:6985-6992.

Matzinger, P. 1998. An innate sense of danger. [Review] [86 refs]. Seminars in Immunology 10:399-415.

Pegram, M. D., Lipton, A., Hayes, D. F., Weber, B. L., Baselga, J. M., Tripathy, D., Baly, D., Baughman, S. A., Twaddell, T. , Glaspy, J. A., and Slamon, D. J. 1998. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. Journal of Clinical Oncology 16, 2659-2671.

Sawai, K and D. Meruelo 1998. Cell-specific transfection choriocarinoma cells by using Sindbis virus hCG expressing chimeric vector. Biochemical & Biophysical Research Communications 248:315-323.

Schnell, M. J., Buonocore, L., Boritz, E., Ghosh, H. P., Chernish, R., and Rose, J. K. 1998. Requirement for a non-specific glycoprotein cytoplasmic domain sequence to drive efficient budding of vesicular stomatitis virus. EMBO Journal 17, 1289-1296.

Yang, Q., Mamounas, M., Yu, G., Kennedy, S., Leaker, B., Merson, J., Wong-Staal, F., Yu, M., Barber, J.R., 1998. Development of novel cell surface CD34-targeted recombinant adeno-associated virus vectors for gene therapy. Hum. Gene. Ther. 9, 1929-1937.

Bachmann, M. F., U. Kalinke, A.Althage, G. Freer, C. Burkhart, H. Roost, M. Aguet, H. Hengartner, and R. M. Zinkernagel. 1997. The role of antibody concentration and avidity in antiviral protection. Science 276:2024-2027.

Bergman, I., M. Ahdab-Barmada, S. S. Kemp, J. A. Griffin,and N. K. Cheung. 1997. A rat model ofleptomeningeal human neoplastic xenografts. J. Neurooncol. 34:221-231.

Jung and Pluckthun: 1997 Improving in vivo folding and stability of a single-chain Fv antibody fragment by loop grafting Protein Engineering, vol. 10, pp. 959-966.

Li, B., J. M. Rosen, J. McMenamin-Balano, W. J. Muller, and A. S. Perkins. 1997. neu/ERBB2 cooperates with p53-172H during mammary tumorigenesis in transgenic mice. Molecular & Cellular Biology 17:3155-3163.

Ohno, K., K. Sawai, Y. Iijima, B. Levin, and D. Meruelo. 1997. Cell-specific targeting of Sindbis virus vectors displaying IgG-binding domains of protein A. Nature Biotechnology 15:763-767.

Rosenfeld, M. R., I. Bergman, L. Schramm, J. A. Griffin, M. G. Kaplitt, and P. I. Meneses. 1997. Adeno associated viral vector gene transfer into lepotmeningeal xenografts. J. Neurooncol. 34: 139-144.

Schnell, M.J., Johnson, J.E., Buonocore, L., Rose, J.K., 1997. Construction of a novel virus that targets HIV-1-infected cells and controls HIV-1 infection. Cell 90, 849-857.

Fuchs, E. J. and P. Matzinger. 1996. Is cancer dangerous to the immune system? [Review] [46 refs]. Seminars in Immunology 8:271-280.

Jost, C.R., Titus, J.A., Kurucz, I., Segal, D.M., 1996. A single-chain bispecific Fv2 molecule produced in mammalian cells redirects lysis by 617 activated CTL. Mol. Immunol. 33, 211-219.

Kalinke, D., E. M. Bucher, B. Ernst, A. Oxenius, H. P. Roost, S. Geley, R. Kofler, R. M. Zinkernagel, and H. Hengartner. 1996. The role of somatic mutation in the generation of the protective humoral immune response against vesicular stomatitis virus. Immunity 5:639-652.

Marin, M., Noel, D., Valsesia-Wittman, S., Brockly, F., Etienne-Julan, M., Russell, S., Cosset, F.L., Piechaczyk, M., 1996. Targeted infection of human cells via major histocompatibility complex class I molecules by Moloney murine leukemia virus-derived viruses displaying single-chain antibody fragment-envelope fusion proteins. J. Virol. 70, 2957-2962.

Qin, H. and S. K. Chatterjee. 1996. Cancer gene therapy using tumor cells infected with recombinant vaccinia virus expressing GM-CSF. Human Gene Therapy 7:1853-1860.

Robbins, P.F., El-Gamil, M., Li, Y.F., Kawakami, Y., Loftus, D., Applella, E., Rosenberg, S.A 1996. A mutated beta-catenin gene encodes a melanoma-specific antigen recognized by tumor infiltrating lymphocytes. J Exp Med. 183:1185-1192.

Schnell, M. J., Buonocore, L., Kretzschmar, E., Johnson, E., and Rose, J. K. 1996 Foreign glycoproteins expresses from recombinant vesicular stomatitis viruses are incorporated efficiently into virus particles. Proceedings of the National Academy of Sciences of the United States of America 93, 11359-11365.

Schnell, M. J., Buonocore, L., Whitt, M. A., and Rose, J. K. 1996 The minimal conserved transcription stop-start signal promotes stable expression of a foreign gene in vesicular stomatitis virus. Journal of Virology 70, 2318-2323.

Wang, R. F., Appella, E., Kawakami, Y., Kang, X., Rosenburg, S.A. 1996. Identification of TRP-2 as a human tumor antigen recognized by cytotoxic T lymphocytes. J Exp Med. 184:2207-2216.

Houbiers, J.G., van der Burg, S.H., van de Watering, L.M., Tollenaar, R.A., Brand, A., van de Velde, C.J., Melief, C.J. 1995. Antibodies against p53 are associated with poor prognosis of colorectal cancer. Br J Cancer. 72:637-641.

Lawson, N. D., E. A. Stillman, M. A. Whitt, and J. K. Rose. 1995. Recombinant vesicular stomatitis viruses from DNA [published erratum appears in Proc Natl Acad Sci USA Sep. 12, 1995;92(19): 9009]. Proc Natl Acad Sci USA 92:4477-4481.

Plakhov, I. V., Arlund, E. E., Aoki, C., and Reiss, C. S. 1995. The earliest events in vesicular stomatitis virus infection of the murine olfactory neuroepithelium and entry of the central nervous system. Virology 209, 257-262.

Sariola, M., Saraste, J., Kuismanen, E., 1995. Communication of post-Golgi elements with early endocytic pathway: regulation of endoproteolytic cleavage of Semliki Forest virus p62 precursor. J. Cell Sci. 108, 2465-2475.

Smith, T.J., Cheng, R.H., Olson, N.H., Peterson, P., Chase, E., Kuhn, R.J., Baker, T.S., 1995. Putative receptor binding sites on alphaviruses as visualized by cryoelectron microscopy. Proc. Natl. Acad. Sci. U.S.A. 92, 10648-10652.

Wang, R.F., Parkhurst, M.R., Kawakami, Y., Robbins, P.F., Rosenburg, S.A. Utilization of an alternative open reading frame of a noraml gene in generating a novel human cancer antigen. J Exp Med. 183:1131-1140.

Wolfel, T., Hauer, M., Schneider, J., Serrano, M., Wolfel, C., Klehmann-Hieb, E., De Plaen, E., Hankeln, T., Meyer zum Buschenfelde, K.H., Beach, D. 1995. A p16INK4a-insensitive CDK4 mutant targeted by cytolytic T lymphocytes in a human melonoma. Science. 269:1281-1284.

Fossum, B., Gedde-Dehl, T., 3rd, Breivik, J., Eriksen ,J.A., Spurkland, A., Thorsby, E., Gaudernack, G. 1994. p21-ras-peptide-specific T-cell responses in a patient with colorectal cancer. CD4+ and CD8+ T cells recognize a peptide corresponding to a common mutation (13Gly—>Asp). Int J Cancer. 56:40-45.

Kawakami, Y., Eliyahu, S., Sakaguchi, K., Robbins, P.F., Rivoltino, L., Yannelli, J.R., Appella, E., Rosenburg, S.A. 1994. Identification of the immunodominant peptides of the MART-1 humna melanoma antigen recognized by the majority of HLA-A2-restricted tumor infiltrating lymphocytes. J Exp Med. 180:347-352.

Livingston, P.O., Wong, G.Y., Adluri, S., Tao, Y., Padavan, M., Parente, R., Hanlon, C., Calves, M.J., Helling, F., Ritter, G. 1994. Improves survival in stage III melanoma patients with GM2 antibodies: a randomized trial of adjuvant vaccination with GM2 ganglioside. J Clin Oncol. 12:1036-1044.

Press, M. F., Pike, M. C., Hung, G., Zhou, J. Y., Ma, Y., George, J., Dietz-Band, J., James, W., Slamon, D. J., Batsakis, J. G. and et al. 1994. Amplification and overexpression of HER-2/neu in carcinomas of the salivary gland: correlation with poor prognosis. Cancer Research 54, 5675-5682.

Rott, O., Herzog, S., and Cash, E. 1994. Autoimmunity caused by host cell protein-containing viruses. Medical Microbiology & Immunology 183, 195-204.

Russell, S. J. 1994. Replicating vectors for gene therapy of cancer: risks, limitations and prospects. [Review]. European Journal of Cancer 30A, 1165-1171.

Russell, S. J. 1994. Replicating vectors for cancer therapy: a question of strategy. Semin. Cancer Biol. 5, 437-443.

Bergman, I., Arbit, E., Rosenblum, M., Larson, S. M., Heller, G., and Cheung, N. K. 1993. Treatment of spinal epidural neuroblastoma xenografts in rats using anti-GD2 monoclonal antibody 3F8. Journal of Neuro-Oncology 15, 235-242.

Dubuisson, J. and C. M. Rice. 1993. Sindbis virus attachment: isolation and characterization of mutants with impaired binding to vertebrate cells. Journal of Virology 67:3363-3374.

Niehans, G. A., Singleton,T. P., Dykoski, D., and Kiang, D. T. 1993. Stability of HER-2/neu expression over time and at multiple metastatic sites. Journal of the National Cancer Institute 85, 1230-1235.

Guy, C. T., M. A. Webster, M. Schaller, T. J. Parsons, R. D. Cardiff, and W. J. Muller 1992. Expression of the neu protooncogene in the mammary epithelium of transgenic mice induces metastatic disease. Proceedings of the National Academy of Sciences of the United States of America 89: 10578-10582.

Ohashi et al. 1991. Ablation of "tolerance" and induction of diabetes by virus infection in viral antigen transgenic mice. Cell 65:305-317.

van der Bruggen, P., Traversari, C., Chomez, P., Lurquin, C., de Plaen, E., Van den Eynde, B., Knuth, A., Boon, T. 1991. A gene encoding an antigene recognized by cytolytic T lymphocytes on a humna melanoma. Science. 254:1643-1647.

Watson, D.G., Moehring, J.M., Moehring, T.J., 1991. A mutant CHO-K1 strain with resistance to Pseudomonas exotoxin A and alphaviruses fails to cleave Sindbis virus glycoprotein PE2. J. Virol. 65, 2332-2339.

Kern, J.A., Schwartz, D. A., Norberg, J. E., Weiner, D. B., Greene, M. I., Torney, L., and Robinson, R. A. 1990. p185 neu expression in human lung adenocarcinomas predicts shortened survival. Cancer Research 50, 5184-5187.

Press, M. F., Cordon-Cardo, C., and Slamon, D. J. 1990. Expression of the HER-2/neu proto-oncogene in normal human adult and fetal tissues. Oncogene 5, 953-962.

Cerny, A., S. Sutter, H. Bazin, H. Hengartner, and R. M. Zinkernagel. 1988. Clearance of lymphocytic choriomeningitis virus in antibody- and B-cell-deprived mice. Journal of Virology 62: 1803-1807.

Cerny, A., C. Heusser, S. Sutter, A. W. Huegin, H. Bazin, H. Hengarther, and R. M. Zinkernagel. 1986. Generation of agammaglobulinaemic mice by prenatal and postnatal exposure to polyclonal or monoclonal anti-IgM antibodies. Scandinavian Journal of Immunology 24:437-445.

Vassalli, J. D., Lombardi, T., Wohlwend, A., Montesano, R., and Orci, L. 1986. Direct cell-to-cell transmission of vesicular stomatitis virus. J Cell Science 85, 125-131.

Bergman, et al., Treatment of implanted mammary tumors with recombinant vescular stomatitis virus targeted to Her$^2$/neu, *Int. J. Cancer*, 121, p. 425-430 (2007).

Gao, et al., Rapid Adaptation of a Recombinant Vescular Stomatitis Virus to a Targeted Cell Line, *Journal of Virology*, Sep. 2006, p. 8603-8612.

* cited by examiner

SEQUENCE LISTING

<160> NUMBER OF SEQ ID NOS: 6

<210> SEQ ID NO 1
<211> LENGTH: 67
<212> TYPE: DNA
<213> ORGANISM: Artificial Sequence
<220> FEATURE:
<223> OTHER INFORMATION: Synthetic Primer

<400> SEQUENCE: 1

```
gcgggtaacc agctcaggtg gaggcggttc aggcggaggt ggctctggcg gtggcggatc      60
tgctagc                                                               67
```

<210> SEQ ID NO 2
<211> LENGTH: 78
<212> TYPE: DNA
<213> ORGANISM: Artificial Sequence
<220> FEATURE:
<223> OTHER INFORMATION: Synthetic Primer

<400> SEQUENCE: 2

```
gcgggttacc agagacccgg aaccagacga gacaggtgcc agagggtaga cagacggtgc      60
ggtcgtttta gcatcgat                                                   78

<210> SEQ ID NO 3
<211> LENGTH: 93
<212> TYPE: DNA
<213> ORGANISM: Artificial Sequence
<220> FEATURE:
<223> OTHER INFORMATION: Synthetic Primer

<400> SEQUENCE: 3
gcgacgcgtc gtacggtaac ctcgagaaag cggccgcgcg cgtttaaact atgaaaaaaa      60
ctaacagaga tccactatgg tgagcaaggg cga                                  93

<210> SEQ ID NO 4
<211> LENGTH: 59
<212> TYPE: DNA
<213> ORGANISM: Artificial Sequence
<220> FEATURE:
<223> OTHER INFORMATION: Synthetic Primer

<400> SEQUENCE: 4
gcggctagcc gtgatatctg ttagtttttt tcatactgag ttacttgtac agctcgtcc      59

<210> SEQ ID NO 5
<211> LENGTH: 64
<212> TYPE: DNA
<213> ORGANISM: Artificial Sequence
<220> FEATURE:
<223> OTHER INFORMATION: Synthetic Primer

<400> SEQUENCE: 5
ggtaaccagc tcaggtggag gcggttcagg cggaggtggc tctggcggtg gcggatctgc      60
tagc                                                                  64

<210> SEQ ID NO 6
<211> LENGTH: 76
<212> TYPE: DNA
<213> ORGANISM: Artificial Sequence
<220> FEATURE:
<223> OTHER INFORMATION: Synthetic Primer

<400> SEQUENCE: 6
atcgatgcta aaacgaccgc accgtcctgt ctacccactg gcacctgtct cgtctggatc      60
cgggtctctg gtaacc                                                     76
```

TARGETING VIRUSES USING A MODIFIED SINDBIS GLYCOPROTEIN

PRIORITY CLAIM

This application claims priority to U.S. Provisional Application Ser. No. 60/614,791, filed Sep. 30, 2004, and U.S. Provisional Application No. 60/609,573, filed Sep. 14, 2004, both of which are incorporated by reference herein in their entireties.

STATEMENT REGARDING GOVERNMENT SUPPORT

The present invention was supported by government grant DAMD 17-00-1-0201, so that the United States Government has certain rights herein.

INTRODUCTION

This invention relates to therapeutic viruses and methods of use thereof.

BACKGROUND OF INVENTION

Metastatic breast cancer is a frequently fatal disease that requires new therapy. Breast cancer is the most common cause of cancer death in women worldwide. There were 39,600 estimated breast cancer deaths in the U.S. in 2002 (Hindle, W. 2002. Breast cancer: introduction. [Review] [33 refs]. *Clinical Obstetrics & Gynecology* 45, 738-745).

Therapy for metastatic breast cancer is inadequate. In most cases, metastatic breast cancer cannot be cured and current medical therapy is merely palliative (Chew, H. K. 2002. Medical management of breast cancer: today and tomorrow. [Review] [75 refs]. *Cancer Biotherapy & Radiopharmaceuticals* 17, 137-149; Danova, M., Porta, C., Ferrari, S., and Riccardi, A. 2001. Strategies of medical treatment for metastatic breast cancer (Review). [Review] [64 refs]. *International Journal of Oncology* 19, 733-739. )

The survival of patients with metastatic disease has not consistently improved over the past decade. The incidence of breast cancer is rising and may increase further with the widespread use of estrogen replacement therapy in postmenopausal women. Despite the advances in early detection conferred by mammography, prevention of breast cancer is presently not feasible to any significant extent.

Weekly treatment with a humanized antibody to the HER2/neu receptor called Herceptin® (Trastuzumab) has been promising as both as a single agent and in combination with standard chemotherapy in patients with HER2/neu over-expressing metastatic breast cancer. (Pegram, M. D., Lipton, A., Hayes, D. F., Weber, B. L., Baselga, J. M., Tripathy, D., Baly, D., Baughman, S. A., Twaddell, T., Glaspy, J. A., and Slamon, D. J. 1998. PHASE II STUDY OF RECEPTOR-ENHANCED CHEMOSENSITIVITY USING RECOMBINANT HUMANIZED ANTI-P185(HER2/NEU) MONOCLONAL ANTIBODY PLUS CISPLATIN IN PATIENTS WITH HER2/NEU-OVEREXPRESSING METASTATIC BREAST CANCER REFRACTORY TO CHEMOTHERAPY TREATMENT. *Journal of Clinical Oncology* 16, 2659-2671; Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., Shak, S., Stewart, S. J., and Press, M. 2002. Efficacy and safety of trastuzumab as a single agent in first-line treatment of HER2-overexpressing metastatic breast cancer. *Journal of Clinical Oncology* 20, 719-726; Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. 2001. Use of chemotherapy plus a monoclonal antibody against HER2 for metastatic breast cancer that overexpresses HER2. [comment]. *New England Journal of Medicine* 344, 783-792; Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J. 1999. Multinational study of the efficacy and safety of humanized anti-HER2 monoclonal antibody in women who have HER2-overexpressing metastatic breast cancer that has progressed after chemotherapy for metastatic disease. *Journal of Clinical Oncology* 17, 2639-2648). Gene amplification of Her2/neu has been noted in 10-40% of primary human breast, ovarian, cervical, endometrial, lung, and pancreatic cancers and is an independent and strong predictor of poor prognosis. (Kern, J. A., Schwartz, D. A., Nordberg, J. E., Weiner, D. B., Greene, M. I., Torney, L., and Robinson, R. A. 1990. p185 neu expression in human lung adenocarcinomas predicts shortened survival. *Cancer Research* 50, 5184-5187; Press, M. F., Cordon-Cardo, C., and Slamon, D. J. 1990. Expression of the HER-2/neu proto-oncogene in normal human adult and fetal tissues. *Oncogene* 5, 953-962; Press, M. F., Pike, M. C., Hung, G., Zhou, J. Y., Ma, Y., George, J., Dietz-Band, J., James, W., Slamon, D. J., Batsakis, J. G., and et al. 1994. Amplification and overexpression of HER-2/neu in carcinomas of the salivary gland: correlation with poor prognosis. *Cancer Research* 54, 5675-5682; Niehans, G. A., Singleton, T. P., Dykoski, D., and Kiang, D. T. 1993. Stability of HER-2/neu expression over time and at multiple metastatic sites. *Journal of the National Cancer Institute* 85, 1230-1235).

[Viruses and viral vectors that kill specific cells are being designed for cancer therapy (Ring, C. J., 2002. Cytolytic viruses as potential anti-cancer agents. J. Gen. Virol. 83, 491-502; Russell, S. J., 1994. Replicating vectors for cancer therapy: a question of strategy. Semin. Cancer Biol. 5, 437-443; Wildner, O., 2001. Oncolytic viruses as therapeutic agents. Ann. Med. 33, 291-304; Zwiebel, J. A., 2001. Cancer gene and oncolytic virus therapy. Semin. Oncol. 28, 336-343. ) Cytolytic replicating viruses represent a new and fundamentally different approach to cancer therapy. Cytolytic viruses differ from standard chemotherapy and radiation therapy in how they target and kill tumor cells. Targeting is achieved by specific binding of the virus to the cancer cell. Viral cytolysis is not dependent on cell growth or division. Viral delivery to its target can be achieved not only via the bloodstream and lymphatic system, but also by cell to cell transmission, spread through the interstitial fluid both within and between tissue planes and by perineural spread. (Tyler, K L. and Nathanson, N. (2001). Pathogenesis of Viral Infections. In "Fundamental Virology" (D. Knipe and P. Howley, Eds.), pp. 199-244. Lippincott Williams & Wilkins, Philadelphia; Plakhov, I. V., Arlund, E. E., Aoki, C., and Reiss, C. S. 1995. The earliest events in vesicular stomatitis virus infection of the murine olfactory neuroepithelium and entry of the central nervous system. *Virology* 209, 257-262; Vassalli, J. D., Lombardi, T., Wohlwend, A., Montesano, R., and Orci, L. 1986. Direct cell-to-cell transmission of vesicular stomatitis virus. *Journal of Cell Science* 85, 125-131). Replicating viruses do not have to be delivered to every tumor cell on the first pass but can spread in waves from the initial site of infection throughout the entire tumor. (Wu, J. T., Byrne, H. M., Kim, D. H., and Wein, L. M. 2001. Modeling and analysis of a virus that replicates selectively in tumor cells. *Bulletin of Mathematical Biology* 63, 731-768). Virus therapy would be unique among biological and chemotherapies in having the potential to be more effective in solid masses of tumor than in minimal residual disease. Moreover, large tumor deposits may initially shield virus from the host immunologic response, because they are devoid of lymphatic drainage, express few MHC antigens and elaborate locally immunosuppressive products. (Russell, S. J. 1994. Replicating vectors for gene therapy of cancer: risks, limitations and prospects. [Review]. *European Journal of Cancer* 30A, 1165-1171).

Breast cancer represents an excellent target for a cytolytic virus, because metastatic disease occurs in masses; tumor associated cell surface receptors are known; and breast tissue is not essential. Destruction of all breast tissue, cancerous or non-cancerous, by direct viral cytolysis or indirect host immunologic response is an acceptable outcome where necessary to achieve therapeutic benefit.

Synergy between virus therapy and chemotherapy is possible because: 1) the basis of viral selectivity is not the faster growth rate of tumor cells compared with most normal tissues; 2) viral oncolysis is likely to produce inflammation and neovascularization within the tumor which will promote delivery of chemotherapeutic agents to tumor cells; 3) chemotherapeutic agents will suppress the host immunologic response and prolong the duration of viral spread and oncolysis. Overlapping toxicities between viral therapy and chemotherapy are not expected because the mechanisms of action are so different (Nemunaitis, J., Cunningham, C., Tong, A. W., Post, L., Netto, G., Paulson, A. S., Rich, D., Blackburn, A., Sands, B., Gibson, B., Randlev, B., and Freeman, S. 2003. Pilot trial of intravenous infusion of a replication-selective adenovirus (ONYX-015) in combination with chemotherapy or IL-2 treatment in refractory cancer patients. *Cancer Gene Therapy* 10, 341-352).

Vesicular Stomatitis Virus (VSV) is an excellent candidate for development as an oncolytic virus, because it is an efficient cell killer that grows and spreads rapidly and yet is safe for human use (de Mattos, C. A., de Mattos, C. C., Rupprecht, C. E., 2001. Rhabdoviruses. In: Knipe, D., Howley, P. (Eds.), Fundamental Virology. Lippincott Williams & Wilkins, Philadelphia, pp. 1245-1277). VSV is endemic in certain human populations, but is not pathogenic. Wild type (wt) VSV has eradicated established tumors in mice when injected intratumorally or intravenously (Balachandran, S., Porosnicu, M., Barber, G. N., 2001. Oncolytic activity of vesicular stomatitis virus is effective against tumors exhibiting aberrant p53, Ras, or myc function and involves the induction of apoptosis. J. Virol. 75, 3474-3479; Fernandez, M., Porosnicu, M., Markovic, D., Barber, G. N., 2002. Genetically engineered vesicular stomatitis virus in gene therapy: application for treatment of malignant disease. J. Virol. 76, 895-904). Selectivity was based on the absence of an interferon response in the tumor cells (Stojdl, D. F., Lichty, B., Knowles, S., Marius, R., Atkins, H., Sonenberg, N., Bell, J. C., 2000. Exploiting tumor-specific defects in the interferon pathway with a previously unknown oncolytic virus. Nat. Med. 6, 821-825).

VSV has many advantages for development as cancer therapy including, most importantly, safety. Although primarily a mild disease of horses, cattle and swine, there are parts of Central America where serologic studies demonstrate that subclinical infection is common in the human population. Use of this agent does not introduce a new virus into the human host and serious illness almost never occurs. VSV is an RNA virus that cannot integrate into the mammalian genome and has no known transforming abilities. It does not produce a persistent infection. A major reason for safety in the humans is that VSV rapidly induces a strong interferon (IFN) response which protects the host (Ring, C. J. 2002. Cytolytic viruses as potential anti-cancer agents. *Journal of General Virology* 83, 491-502).

VSV is an enveloped negative strand RNA virus with a single surface glycoprotein (gp) called G that fully determines binding of the virus to target cells as well as promoting pH-dependent fusion of the virus envelope with endosome membranes (Rose, J. K., Whitt, M. A., 2001. Rhabdoviridae: the viruses and their replication. In: Knipe, D., Howley, P. (Eds.), Fundamental Virology Lippincott Williams & Wilkins, Philadelphia, pp. 1221-1244). VSV contains only 5 genes and can be created entirely from vectors that express these genes, without effect on viral packaging. The viral genome has the capacity to accommodate additional genetic material. At least two additional transcription units, totaling 4.5 kb, can be added to the genome. Added genes are stably maintained in the genome upon repeated passage (Schnell, M. J., Buonocore, L., Boritz, E., Ghosh, H. P., Chernish, R., and Rose, J. K. 1998. Requirement for a non-specific glycoprotein cytoplasmic domain sequence to drive efficient budding of vesicular stomatitis virus. *EMBO Journal* 17, 1289-1296; Schnell, M. J., Buonocore, L., Kretzschmar, E., Johnson, E., and Rose, J. K. 1996a. Foreign glycoproteins expressed from recombinant vesicular stomatitis viruses are incorporated efficiently into virus particles. *Proceedings of the National Academy of Sciences of the United States of America* 93, 11359-11365; Schnell, M. J., Buonocore, L., Whitt, M. A., and Rose, J. K. 1996b. The minimal conserved transcription stop-start signal promotes stable expression of a foreign gene in vesicular stomatitis virus. *Journal of Virology* 70, 2318-2323; Kahn, J. S., Schnell, M. J., Buonocore, L., and Rose, J. K. 1999. Recombinant vesicular stomatitis virus expressing respiratory syncytial virus (RSV) glycoproteins: RSV fusion protein can mediate infection and cell fusion. *Virology* 254, 81-91).

VSV infection also elicits strong humoral and cellular immune responses and evokes an inflammatory response at the site of infection that includes macrophages, neutrophils and lymphocytes. VSV incorporates portions of the cellular plasma membrane into its envelope and can cause the immune system to react to these antigens. Immunization with VSV grown in myelin basic protein (MBP) expressing cell cultures evoked a T cell response to the "self" MBP protein (Rott, O., Herzog, S., and Cash, E. 1994. Autoimmunity caused by host cell protein-containing viruses. *Medical Microbiology & Immunology* 183, 195-204).

VSV has also been demonstrated to be a potent oncolytic virus. It kills any tumor cell that it infects within hours and affects both dividing and non-dividing cells. Studies of subcutaneous and pulmonary tumors in mice demonstrated that wild type (wt) VSV administered directly into subcutaneous tumor at a dose of $2 \times 10^7$ PFU (plaque forming units) or IV at a dose of $5 \times 10^6$ PFU achieved tumor regression but did not produce replicating infections in body organs (Fernandez, M., Porosnicu, M., Markovic, D., and Barber, G. N. 2002. Genetically engineered vesicular stomatitis virus in gene therapy: application for treatment of malignant disease. *Journal of Virology* 76, 895-904). Many tumor cell types have lost responsiveness to IFN and are therefore very sensitive to killing by VSV, making this virus an excellent candidate for cancer therapy (Stojdl, D. F., Lichty, B., Knowles, S., Marius, R., Atkins, H., Sonenberg, N., and Bell, J. C. 2000. Exploiting tumor-specific defects in the interferon pathway with a previously unknown oncolytic virus. *Nature Medicine* 6, 821-825; Stojdl, D. F., Lichty, B. D., tenOever, B. R., Paterson, J. M., Power, A. T., Knowles, S., Marius, R., Reynard, J., Poliquin, L., Atkins, H., Brown, E. G., Durbin, R. K., Durbin, J. E., Hiscott, J., and Bell, J. C. 2003a. VSV strains with defects in their ability to shutdown innate immunity are potent systemic anti-cancer agents. *Cancer Cell* 4, 263-275; Stojdl, D. F., Lichty, B. D., tenOever, B. R., Paterson, J. M., Power, A. T., Knowles, S., Marius, R., Reynard, J., Poliquin, L., Atkins, H., Brown, E. G., Durbin, R. K., Durbin, J. E., Hiscott, J., and Bell, J. C. 2003b. VSV strains with defects in their ability to shutdown innate immunity are potent systemic anti-cancer agents. *Cancer Cell* 4, 263-275).

The present inventors have previously reported the development of a recombinant VSV whose only surface glycoprotein (gp) was a Sindbis virus (SV) gp, called Sindbis-ZZ, which could be targeted to breast cancer cells (Bergman et al. Vesicular stomatitis virus expressing a chimeric Sindbis glycoprotein containing an Fc antibody binding domain targets to Her2/neu overexpressing breast cancer cells. Virology. Nov. 25, 2003;316(2):337-47. ) The cellular receptor for G is ubiquitous and VSV promiscuously infects most cell types. The surface gp of SV consists of an E1 fusion protein and an E2 binding protein. Deletion of amino acids 72 and 73 within E2 reduces binding and infectivity of the virus >90% (Dubuisson, J., Rice, C. M., 1993. Sindbis virus attachment: isolation and characterization of mutants with impaired binding to vertebrate cells. J. Virol. 67, 3363-3374). The Sindbis gp gene was further modified at this site by others to encode two synthetic immunoglobulin G (IgG) Fc-binding domains called ZZ derived from protein A of the *Staphylococcus aureus* spa gene (Ohno, K., Sawai, K., Iijima, Y., Levin, B., Meruelo, D., 1997. Cell-specific targeting of Sindbis virus vectors displaying IgG-binding domains of protein A. Nat. Biotechnol. 15, 763-767; Morizono, K., Bristol, G., Xie, Y. M., Kung, S. K., Chen, I. S., 2001. Antibody-directed targeting of retroviral vectors via cell surface antigens. J. Virol. 75, 8016-8020; Sawai, K., Meruelo, D., 1998. Cell-specific transfection of choriocarcinoma cells by using Sindbis virus hCG expressing chimeric vector. Biochem. Biophys. Res. Commun. 248, 315-323). Sindbis viruses and retroviruses expressing this ZZ-modified gp could be targeted to specific cells by the addition of antibody. The inventors incorporated this glycoprotein gene into the VSV genome and made a VSV that expressed this modified Sindbis gp and not the native VSV G gp. Genetic engineering has previously been developed to create VSV from plasmid components (Schnell, M. J., Buonocore, L., Kretzschmar, E., Johnson, E., Rose, J. K., 1996. Foreign glycoproteins expressed from recombinant vesicular stomatitis viruses are incorporated efficiently into virus particles. Proc. Natl. Acad. Sci. U.S.A. 93, 11359-11365). The inventors showed that VSV recombinant virus and pseudotype virus expressing the Sindbis ZZ gp could be targeted to Her2/neu expressing breast cancer cells using antibody to Her2/neu.

Targeting of the VSV containing Sindbis-ZZ however was inefficient, since its mechanism required the intermediate binding of a cell-specific antibody with a non-specific antibody binding site expressed on the viral surface. In vivo competition for the non-specific antibody binding site will include the large pool of host IgG antibodies. In addition, selective adaptation of this virus on targeted cells was difficult, because each new generation of virus required additional antibody to allow binding and infection of the next round of cells.

Previous attempts to target viruses to cancer cells using single chain antibodies (SCA) have also been limited due to low titer. Previous reports using SCA to target retroviruses, adeno-associated virus (AAV) and attenuated measles virus (MV) produced viral titers of about $1\times10^5$/ml (Jiang et al., 1998; Khare et al., 2001; Marin et al., 1996; Martin et al., 2003; Yang et al., 1998). Also, the SCA gene was not incorporated into the retroviral genome and the viruses could not replicate. In addition, these viruses cannot be used directly to kill tumor cells because they are not cytolytic. For MV, the titers against specific cells were $6\times10^4$-$6\times10^5$/ml and in addition native MV binding was not at all attenuated. Rather, the tropism of the virus was extended to cells not normally infected by MV. Unlike retroviruses, however, these targeted MV were replication competent and cytolytic (Bucheit et al., 2003; Hammond et al., 2001; Peng et al., 2003).

Although VSV is a potent oncolytic virus, wild type VSV can cause significant morbidity if the virus enters the brain of animals. The possibility of such movement into the brain becomes a significant barrier to its practical application for therapeutic purposes.

Thus, there remains a need in the art for viruses, compositions and methods which enable safe, efficient and effective use of these viruses in the treatment of disorders and diseases, such as breast cancer.

SUMMARY OF THE INVENTION

The present invention relates to viruses that are engineered to contain a surface ligand molecule which targets the virus to a cell of interest. In particular non-limiting embodiments, the cell of interest is desirably ablated and may be a cancer cell, an infected cell, a cell exhibiting a non-malignant proliferative disorder, or a cell of the immune system. Alternatively, the cell of interest is a target for gene therapy.

In particular embodiments where the cell of interest is desirably destroyed, the virus of the present invention is a cytolytic replicating virus. In other embodiments, where the viability of the target cell is to be maintained, the virus of the invention is a non-lytic virus. A viral surface protein associated with infectivity may be modified to reduce infectivity of non-target cells and to incorporate a target cell-specific ligand. Viruses used according to the invention are preferably enveloped viruses.

In a preferred non-limiting embodiment of the invention, the virus is a recombinant replicating VSV (rrVSV) engineered to express a modified glycoprotein (gp) gene derived from the Sindbis virus. In a further embodiment of the invention, the viral surface proteins further comprise a single chain antibody (SCA) with specificity for a cell surface protein. In a still further embodiment of the invention, the cell surface protein is the human epidermal growth factor receptor Her2/neu protein, erbb2.

The viruses of the present invention may also express various therapeutic genes, including cytokines such as GM-CSF, IL-12, interferon beta, interferon gamma, IL-2, Il-10, agonists or antagonists thereof, or other cytokine or chemokine.

The present invention further relates to methods of producing the modified virus disclosed herein, having improved expression of a modified glycoprotein. The present invention also relates to methods of producing a modified virus having improved infectivity into specific cell types.

The present invention still further relates to method of using the modified virus to target to specific cell types. The viruses can be used in cancer therapy, gene therapy, treatment of various immune, autoimmune and/or inflammatory diseases, treatment of infectious diseases, and in the facilitation of organ, tissue or cell transplantation. In related embodiments, the present invention provides for pharmaceutical compositions comprising modified virus.

DETAILED DESCRIPTION OF THE INVENTION

Figure 1A:
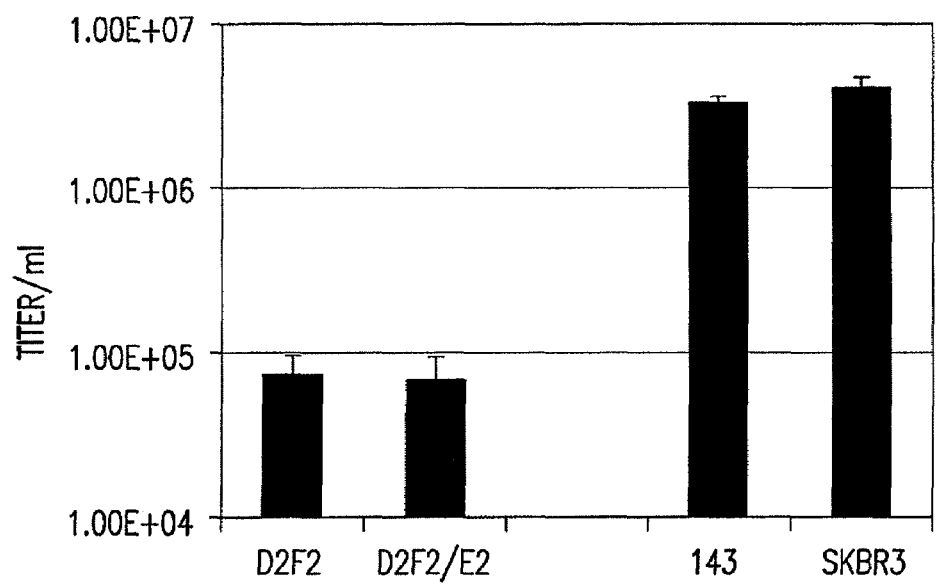
FIGS. 1A-1B shows bar graphs of the titer on two pairs of cell lines, one with and one without Her2/neu, of non-replicating VSV-EGFP-ΔG coated with wt Sindbis gp (FIG. 1A) and pseudotype VSV-EGFP-ΔG coated with Sindbis-SCA-erbb2 gp (FIG. 1B).

The present invention is related to viruses having an altered surface protein that targets preferentially to specific cells. Preferably, the viruses of the present invention are enveloped viruses such as vesicular stomatitis virus ("VSV"), or members of the Retrovirus, Rhabdovirus, Alphavirus, Togavirus, Flavivirus, Coronavirus, Orthomyxovirus, or Bunyavirus family. For embodiments in which the target cell is to be ablated, the virus is preferably a cytolytic virus (or a pseudotype of VSV). For embodiments in which the target cell is not to be destroyed (such as gene therapy applications) the virus is preferably non-lytic (e.g., a retrovirus or a lentivirus). In particularly preferred non-limiting embodiments, the virus may be a vesicular stomatitis virus (VSV).

For example but not by way of limitation, the genome of a recombinant virus according to the invention may comprise a site for insertion of a surface protein associated with infectivity as well as a site for insertion of a therapeutic gene (e.g. a cytokine, cytokine agonist, or cytokine antagonist). Each site may be rendered amenable to the insertion of alternative surface proteins and therapeutic genes using methods known in the art; for example, each site may be flanked by restriction enzyme cleavage sites to facilitate insertion of cassettes comprising the desired genes. Each gene should be in expressible form according to the life cycle of the parent virus (see below for "stop-start" site for VSV), and where appropriate should be operably linked to a suitable promoter element.

The surface protein associated with infectivity may be derived from the same type of virus as the recombinant virus or another type of virus. In non-limiting embodiments, the surface protein is a modified form of Sindbis E2 and/or E1 proteins.

In a specific non-limiting embodiment of the invention, a rrVSV genome comprises a modified Sindbis E2 binding gp and the native E1 fusion gp. These proteins in the Sindbis virus have been attributed to the binding and fusion mechanisms of the virus during infection. In a preferred embodiment of the invention, the Sindbis E2 binding gp and/or E1 fusion gp is modified to exhibit reduced binding and/or infectivity. Preferably, binding and/or infectivity is(are) reduced by at least about 50 percent, at least about 75 percent, or at least about 90 percent. A modification may be an insertion, a deletion, or a substitution of one or more amino acid.

In particular non-limiting embodiments, the surface protein associated with infectivity, which, in modified form, is incorporated into a virus according to the invention, is the Sindbis E2 protein. The Sindbis E2 gene encodes a peptide that is 423 amino acids in length, representing positions 329-751 of the peptide encoded by the entire structural gene complex. An amino acid sequence of E2 is provided at GenBank Accession No. P11259. Herein, amino acid positions are defined so that the first amino acid of E2 is position 1

(which would be position 329 of the entire complex). The E2 gene is modified to decrease infectivity of non-target cells, by insertion, deletion, or substitution of one or more amino acid. E2 residues 55, 121, and 260 have been associated with viral virulence (Kobiler, D., Rice, C. M., Brodie, C., Shahar, A., Dubuisson, J., Halevy, M., Lustig, S. 1999. A single nucleotide change in the 5' noncoding region of Sindbis virus confers neurovirulence in rats. J Virol. 73:10440-6) and residues 69-74 and 170-220 have been associated with viral binding (Dubuisson, J., Rice, C. M. 1993. Sindbis virus attachment: isolation and characterization of mutants with impaired binding to vertebrate cells. J. Virol. 67:3363-74; Myles, K. M., Pierro, D. J., Olson, K. E. 2003. Deletions in the putative cell receptor-binding domain of Sindbis virus strain MRE16 E2 glycoprotein reduce midgut infectivity in Aedes aegypti. J Virol. 77:8872-81). Accordingly, in particular non-limiting embodiments, the Sindbis E2 gene may be modified by insertion, deletion, or substitution of one or more amino acid residues at position 69, 70, 71, 72, 73, 74, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 55, 121 or 260. Preferably, but not my way of limitation, the modification comprises a deletion of amino acids 72 and 73 of the E2 binding gp, and/or amino acid 70 is mutated from Lys to Glu. In another specific non-limiting embodiment, E1 can be modified by ligation to the intracytoplasmic domain of VSV G.

In various non-limiting embodiments of the invention, a VSV virus comprises a modified Sindbis E2 binding gp with reduced infectivity and a ligand which targets the modified virus to a cell of interest. Preferably, the ligand is linked to E2 gp. A modified E2 gp may comprise linkage to the ligand as its sole modification (e.g., as an insertional mutation) or may comprise one or more additional modification. In non-limiting embodiments, the modification may be insertion of a targeting ligand. The ligand may be a binding partner for any receptor associated with the cell of interest, and preferably is not expressed by native virus. Alternatively, the ligand may bind indirectly to a target cell specific antigen, for example via an immunoglobulin molecule.

In a first set of non-limiting embodiments, the ligand may be an IgG binding domain. For example, the IgG-binding domains derived from staphylococcal protein A that bind to the Fc (constant) region of IgG immunoglobulins. Display of a synthetic derivative of IgG-binding domains of protein A (ZZ) domains promote targeting the recombinant VSV to the host cell of interest when used in combination with an appropriate antibody. The VSV of the present invention called VSV-Sindbis-ZZ displays increased binding capacity to IgG. In a preferred embodiment, the VSV comprises Sindbis gp modified between amino acids 71 and 74 to express two ZZ domains. This ZZ modified VSV can be targeted to any antigen by using the appropriate antibody, where the antibody targets cell surface markers of cancer cells, specific cells of the immune system or any cell with a relatively specific cell surface marker in order to delete that cell. Other examples of IgG binding domains may also be employed.

In a second set of non-limiting embodiments, the ligand may be a single chain antibody (SCA) with specificity for a cell surface protein. Other SCA could be incorporated into the surface protein that would target the virus to any cell surface receptor including proteins, glycolipids or glycoproteins. The SCA may recognize any target-cell specific antigen, including but not limited to p53, ras, β-catenin, CDK4, CDC27, α actinin-4, HER2, WT1, EphA3, EGFR, CD4, CD8, CD20 MAGE, BAGE, GAGE, NY-ESO-1, Tyrosinase, TRP1/gp75, TRP2, gp100, Melan-A/MART1, gangliosides, or PSMA (Houbiers, J. G., van der Burg, S. H., van de Watering, L. M., Tollenaar, R. A., Brand, A., van de Velde, C. J., Melief, C. J. 1995. Antibodies against p53 are associated with poor prognosis of colorectal cancer. Br J Cancer. 72:637-641.; Fossum, B., Gedde-Dahl, T., 3rd, Breivik, J., Eriksen, J. A., Spurkland, A., Thorsby, E., Gaudemack, G. 1994. p21-ras-peptide-specific T-cell responses in a patient with colorectal cancer. CD4+ and CD8+ T cells recognize a peptide corresponding to a common mutation (13Gly->Asp). Int J Cancer. 56:40-45. ; Robbins, P. F., El-Gamil, M., Li, Y. F., Kawakami, Y., Loftus, D., Appella, E., Rosenberg, S. A 1996. A mutated beta-catenin gene encodes a melanoma-specific antigen recognized by tumor infiltrating lymphocytes. J Exp Med. 183:1185-1192. ; Wolfel, T., Hauer, M., Schneider, J., Serrano, M., Wolfel, C., Klehmann-Hieb, E., De Plaen, E., Hankeln, T., Meyer zum Buschenfelde, K. H., Beach, D. 1995. A p16INK4a-insensitive CDK4 mutant targeted by cytolytic T lymphocytes in a human melanoma. Science. 269:1281-1284. ; Wang, R. F., Wang, X., Atwood, A. C., Topalian, S. L., Rosenberg, S. A. 1999. Cloning genes encoding MHC class II-restricted antigens: mutated CDC27 as a tumor antigen. Science. 284:1351-1354. ; Mami-Chouaib, F., Echchakir, H., Dorothee, G., Vergnon, I., Chouaib, S. 2002. Antitumor cytotoxic T-lymphocyte response in human lung carcinoma: identification of a tumor-associated antigen. Immunol Rev. 188:114-121. ; Baselga, J., Albanell, J. 2001. Mechanism of action of anti-HER2 monoclonal antibodies. Ann Oncol. 12 Suppl 1:S35-41. ; Tsuboi, A., Oka, Y., Ogawa, H., Elisseeva, O. A., Li, H., Kawasaki, K., Aozasa, K., Kishimoto, T., Udaka, K., Sugiyama, H. 2000. Cytotoxic T-lymphocyte responses elicited to Wilms' tumor gene WT1 product by DNA vaccination. J Clin Immunol. 20:195-202. ; Chiari, R., Hames, G., Stroobant, V., Texier, C., Maillere, B., Boon, T., Coulie, P. G. 2000. Identification of a tumor-specific shared antigen derived from an Eph receptor and presented to CD4 T cells on HLA class II molecules. Cancer Res. 60:4855-4863. ; Cohen, R. B. 2003. Epidermal growth factor receptor as a therapeutic target in colorectal cancer. Clin Colorectal Cancer. 2:246-251.; Wannesson, L., Ghielmini, M. 2003. Overview of Antibody Therapy in BCell Non-Hodgkin's Lymphoma. Clin Lymphoma. 4 Suppl 1:S5-S12. ; van der Bruggen, P., Traversari, C., Chomez, P., Lurquin, C., De Plaen, E., Van den Eynde, B., Knuth, A., Boon, T. 1991. A gene encoding an antigen recognized by cytolytic T lymphocytes on a human melanoma. Science. 254:1643-1647. ; Jager, E., Chen, Y. T., Drijfhout, J. W., Karbach, J., Ringhoffer, M., Jager, D., Arand, M., Wada, H., Noguchi, Y., Stockert, E., Old, L. J., Knuth, A. 1998. Simultaneous humoral and cellular immune response against cancer-testis antigen NY-ESO-1:definition of human histocompatibility leukocyte antigen (HLA)-A2-binding peptide epitopes. J Exp Med. 187:265-270. ; Kawakami, Y., Robbins, P. F., Wang, X., Tupesis, J. P., Parkhurst, M. R., Kang, X., Sakaguchi, K., Appella, E., Rosenberg, S. A. 1998. Identification of new melanoma epitopes on melanosomal proteins recognized by tumor infiltrating T lymphocytes restricted by HLA-A1, -A2, and -A3 alleles. J Immunol. 161:6985-6992. ; Wang, R. F., Parkhurst, M. R., Kawakami, Y., Robbins, P. F., Rosenberg, S. A. Utilization of an alternative open reading frame of a normal gene in generating a novel human cancer antigen. J Exp Med. 183:1131-1140. ; Wang, R. F., Appella, E., Kawakami, Y., Kang, X., Rosenberg, S. A. 1996. Identification of TRP-2 as a human tumor antigen recognized by cytotoxic T lymphocytes. J Exp Med. 184:2207-2216. ; Kawakami, Y., Eliyahu, S., Sakaguchi, K., Robbins, P. F., Rivoltini, L., Yannelli, J. R., Appella, E., Rosenberg, S. A. 1994. Identification of the immunodominant peptides of the MART-1 human melanoma antigen recognized by the majority of HLA-A2-restricted tumor infiltrating lymphocytes. J Exp Med. 180:347-352. ; Livingston, P. O., Wong, G. Y., Adluri, S., Tao, Y., Padavan, M., Parente, R., Hanlon, C., Calves, M. J., Helling, F., Ritter, G. 1994. Improved survival in stage III melanoma patients with GM2 antibodies: a randomized trial of adjuvant vaccination with GM2 ganglioside. J Clin Oncol. 12:1036-1044. ; Bander, N. H., Nanus, D. M., Milowsky, M. I., Kostakoglu, L., Vallabahajosula, S., Goldsmith, S. J. 2003. Targeted systemic therapy of prostate cancer with a monoclonal antibody to prostate-specific membrane antigen. Semin Oncol. 30:667-676).

In a third set of non-limiting embodiments, the ligand may bind to a cellular receptor, and may be, for example, transferring, a cytokine (such as ciliary neurotrophic factor) or a receptor-binding antagonist thereof, ligands for integrin or cadherin molecules, etc. For example the gene for the dendritic cell ligand B7.1 could be inserted at the SCA site within the gene coding for the modified Sindbis glycoprotein gene. The virus would then be targeted to cells that express the Cd28 or CTLA4 receptors. In a further embodiment of the invention, the cell surface protein is the human epidermal growth factor receptor Her2/neu protein, erbb2.

In further non-limiting embodiments of the invention, the viruses of the present invention may also express various genes, such as, but not limited to, cytokine or chemokines, such as GM-CSF and IL-12, interferon beta, interferon gamma, IL-10, or an agonist or an antagonist thereof, or any other viral or mammalian gene. Examples of other genes, include, but is not limited to, urokinase, tumor necrosis factor-α (TNF-α) or interleukin-4 (IL-4), herpesvirus thymidine kinase (HSV-TK), purine nucleoside phosphorylase, cytosine deaminase, and EGFP.

The VSV of the present invention may also exhibit temperature sensitivity. Such VSV exhibit the following mutations, Amino Acid 55 in E2 and Amino Acid 246 in E2, preferably where amino acid 55 in E2 is changed from glutamine to arginine and amino acid 246 in E2 is changed from histidine to arginine.

Other mutations that exhibit improved properties include the following within the single chain domain as numbered by Jung and Pluckthun: Protein Engineering, Vol 10, pp 959-966, 1997: $_{pro}52a_{leu}$ and $_{ala}78_{thr}$. The $_{pro}52a_{leu}$ mutation is located in an antibody complementarity determining region, CDR2 and the $_{ala}78_{thr}$ mutation is in a framework region, FR3. Such a mutation resulted in increased incorporation of gp into the viral envelope, improved infectivity, faster entry, decreased interferon induction, much greater stability and much improved viral production.

In an embodiment of the invention, the VSV preparations produce high titers. The rrVSV expressing SCA to Her2/neu called Sindbis-SCA-erbb2 achieves titers of $3.1\times10^7$/ml. Generally, the rrVSV particles of the present invention grew to titers of $10^7$/ml. In addition, the preparations are stable in response to freeze/thaw cycles and can be further concentrated. The present invention also contemplates the substitution of the native VSV G intracellular tail in place of the E1 intracellular tail to create a rrVSV of higher titer.

The present invention also contemplates methods of producing the modified virus disclosed herein. The method comprises generating the viral vectors, where the viruses exhibited improved titer and higher gp expression. The method comprises subjecting the VSV to one or more serial passages. A single pass of the newly created VSV in SKBR3 cells, a human breast cancer line that overexpresses Her2/neu, causes reversion of the phenotype of the surface glycoprotein from temperature sensitive to temperature insensitive. A single or multiple series of passes may be sufficient to achieve such a characteristic. For example, serial passage for 15 passes on D2F2/E2 cells, a mouse mammary carcinoma cell line stably transfected with human Her2/neu, increased viral titer from an initial value of $2\times10^5$/ml to a final titer of $2.3\times10^7$/ml.

One method of producing recombinant VSV is disclosed in Lawson et al. (Lawson, N. D., Stillman, E. A., Whitt, M. A., Rose, J. K., 1995. Recombinant vesicular stomatitis viruses from DNA. Proc. Natl. Acad. Sci. U.S.A. 625 92, 4477-4481.)

In a specific, non-limiting embodiment, rrVSV may be engineered to incorporate a SCA (or by analogy, another ligand) as follows. The gene segment coding for the mature SCA structural protein without the signal sequence may be amplified with a series of primers to produce the following construct: ggtaacc(BstE II) agctcaggtggaggcggttcaggcggag-gtggctctggcggtggcg gatctgctagc (Nhe 1) (SEQ ID NO:5)-mature SCA-erbB2-atcgat(Cla 1) gctaaaacgaccgcaccgtcct-gtctac ccactggcacctgtctcgtctggatccgggtctctggtaacc (BstE II) (SEQ ID NO:6). A flexible poly-glycine linker may be placed preceding the mature SCA, between the BstE II and Nhe 1 restriction sites. A spacer adapted from Jost (Jost et al., 1996) and consisting of the first 13 amino acids of the CH 1 region of the 2C 11 hamster monoclonal antibody and a flexible serine-glycine end may be placed following the mature SCA, between the Ca 1 and BstE II restriction sites. This construct may be placed between amino acids 71 and 74 of the Sindbis gp to create a chimeric Sindbis gp which includes the first 71 amino acids of E2 followed in order by a poly-glycine linker, SCA to erbb2, CHI1 linker, the remainder of the E2 Sindbis gp and the entire E1 Sindbis gp. This construct enables easy replacement of the specific SCA-erbb2 with any other SCA or other ligand by digesting and ligating at the Nhe1 and Cla1 sites.

In a rrVSV, in order to provide for expression of a modified surface antigen associated with infectivity and/or ligand and/or therapeutic gene (e.g. cytokine, cytokine agonist or cytokine antagonist), a VSV "stop-start signal" may be operably linked to the gene encoding the surface antigen and/or ligand and/or therapeutic gene. A native start-stop signal occurs in front of each gene in VSV that stops expression of the previous gene and starts expression of the next one using the VSV L polymerase which is packaged with the virus. An Mlu1 site in front of the glycoprotein gene may be used for this purpose, and the following construct may be prepared by PCR: Mlu1-[e.g., therapeutic gene such as GM-CSF]-Stop-Start-Mlu1. This cassette may be inserted into the VSV genome.

In working examples of the invention, reverse genetics was used to identify four base pair mutations in the Sindbis glycoprotein gene that resulted in a greatly improved virus. The adapted virus showed higher density of glycoprotein on the viral envelope, improved infectivity, faster entry into infected cells, higher burst size and greater stability. The selection process did not alter any other gene sequence within the virus. These changes have been incorporated into a vector expressing the viral genome to reproducibly create rrVSV with these beneficial mutations. Further, the mouse GM-CSF gene was incorporated into the rrVSV genome and it was demonstrated that this virus could eradicate breast cancer cells implanted into the peritoneum of immune competent mice. Four of seven cured animals that were re-challenged with the Her2/neu expressing breast cancer tumor did not develop tumor and more importantly, 3 of these 4 that were then challenged with the parent mouse tumor that does not express Her2/neu, also did not develop tumor. This result indicates that following viral therapy the animals have developed immunity not only to the Her2/neu receptor but also to unrelated tumor antigens within the parent tumor.

Accordingly, the present invention may be used in various therapeutic applications, and provides for a method of targeting therapy to a cell of interest comprising administering, to the cell, a modified virus as disclosed herein. The cell may be present in a subject, which may be a human or a non-human subject (in vivo administration), or may be present in vitro, for example in a cell culture, or ex vivo, for example in a tissue or organ to be transplanted.

The present invention provides for a method of destroying a cell, and/or decreasing the size of a population of cells, comprising administering, to the cell or cell population, optionally contained in a subject, a modified virus as disclosed herein. In specific non-limiting embodiments, the virus is a cytolytic virus comprising a surface antigen binding protein modified to decrease its infectivity of non-target cells, and comprising a ligand that targets the virus to the target cell of interest. Optionally, the modified virus further contains a gene encoding a cytokine, cytokine agonist or cytokine antagonist in expressible form. Such methods may be used, for example and not by way of limitation, in the treatment of a malignancy or a non-malignant or pre-malignant disorder of cell proliferation, where, e.g., the ligand binds to a tumor specific or proliferative disorder specific antigen. In alternative non-limiting embodiments, the methods may be used in conjunction with organ transplantation, where the modified virus is targeted to cells of the immune system, for example by ligands that bind to CD4 or CD8 cell surface antigens, to elicit an immunosuppressive response. In still other non-limiting embodiments, the method may be used to treat an infection associated with expression of a pathogen-associated surface antigen, where the ligand is directed at the surface antigen. Where the modified virus is administered to a subject, the amount administered would depend upon the virus used, and may range from about $10^5$ to about $10^{10}$ pfu. Where the virus is rrVSV, the amount administered may be between about $10^7$ to about $10^9$ pfu, preferably, where the subject is a human, between about $10^8$ and $10^9$ pfu. Administration may be by any method known in the art, including intravenous, intrathecal, intraperitoneal, intramuscular, subcutaneous, oral, nasal, or by direct local injection or instillation. The virus may be administered as a single dose, as repeated doses, or in divided doses.

Where the modified viruses of the invention are to be used to treat malignancy, the methods of the invention may be practiced in conjunction with other forms of therapy such as chemotherapy, radiotherapy, etc. In a specific, non-limiting embodiment, the present invention provides for a method of treating a subject having malignancy comprising administering a chemotherapeutic agent to the subject, thereby reducing the number of cells of the immune system of the subject, followed by or concurrently with administering modified virus according to the invention.

The present invention further provides for pharmaceutical compositions comprising an effective amount of modified virus as described above, in a suitable pharmaceutical carrier. Such compositions may comprise one or more additional bioactive agent, such a chemotherapeutic agent, a cytokine, a cytokine agonist, or a cytokine antagonist.

EXAMPLES

Example 1

Materials

Cells, antibodies and chemicals. The following cell lines were obtained from American Type Culture Collection (ATCC) (Rockville, Md.) and grown using standard tissue culture techniques in a humidified incubator at 37 8C with 5% CO2:SKBR3 human breast adenocarcinoma, 143 human osteosarcoma, COS-7 simian kidney and BHK 21 hamster kidney. SKBR3 cells are known Her2/neu amplified/overexpressing breast cancer cells whereas 143 do not express measurable Her2/neu (Bergman et al., 2001). D2F2/E2 is a mouse mammary tumor line that has been stably transfected with a vector expressing the human Her2/neu gene and was a obtained from Dr. Wei-Zen Wei, Karmanos Cancer Institute, Wayne State University, Detroit, Mich. D2F2 is the parent mouse mammary tumor cell line. Absence of mycoplasma contamination in all cell lines was confirmed by the Gen-Probe rapid detection system (Gen-Probe Incorp., San Diego, Calif.). MAb 4D5, a mouse monoclonal antibody directed to the Her2/neu receptor was provided by Genentech, Inc. (San Francisco, Calif.). Herceptin, the humanized form of 4D5 was obtained from Genentech. Bafilomycin A1 was obtained from Kamiya Biomedical Co. (Seattle, Wash.).

Example 2

Creation of Vector Expressing Sindbis gp Mutations (Sindbis-SCA)

This example discloses the steps for generating a vector expressing a modified Sindbis gp with amino acids 72 and 73 deleted and an SCA with linkers on each side placed in this site.

PCR as detailed below was performed to create the following construct called PCR product #1:BstEIl-Glycine linker-Nhe 1-Single chain antibody (SCA)-Cla1-Spacer-BstEII. Preceding the mature SCA, between the BstEII and Nhe1 restriction sites, a flexible poly-glycine linker was inserted. Following the mature SCA between the Cla1 and BstEII restriction sites, a spacer adapted from Jost et al. (1996) was inserted and consisting of the first 13 amino acids of the CH1 region of the 2C11 hamster monoclonal antibody and a flexible serine-glycine end. This construct was used to replace ZZ between amino acids 71 and 74 of the Sindbis-ZZ chimeric gp to create a chimeric Sindbis gp which consisted of the first 71 amino acids of E2 followed in order by a poly-glycine linker, SCA to erbb2, CH1 linker, the remainder of the E2 Sindbis gp and the entire E1 Sindbis gp. This construct was called Sindbis-SCA-erbb2. It was designed so that the specific SCA-erbb2 in this construct could easily be replaced with any other SCA by digesting and ligating at the Nhe1 and Cla1 sites.

Site directed mutagenesis was used to destroy any BstEII, Nhe1 or Cla1 sites within the gene for the SCA while retaining the original amino acid sequence.

The following primers were used:
Forward primer: (SEQ ID NO:1)
gcgGGT AACCagctcaggtggaggcggttcag-gcggaggtggcggctctggcggtggcggatctGCT AGC
first 21 bases expressing the mature SCA protein (does not include signal sequences)
Reverse primer: (SEQ ID NO:2)
gcgGGTT ACCagagacccggaaccagacgagacag-gtgccagagggtagacagacggtgcggtcgttttagcATCGAT last 21 bases expressing the mature SCA protein excludeing the stopm codon.

The PCR product was ligated into a cloning vector, bacteria transformed, clonal DNA isolated, digested with BstEII, and the digested PCR product #1 was purified. Sindbis-ZZ obtained from Dr. Irvin S. Y. Chen, University of California, Los Angeles Medical School, was digested with BstEII. The ~8 kb vector was purified and the 0.4 kb insert was discarded. This vector is referred to as Vector #1.

PCR product #1 was ligated with Vector #1, bacteria transformed, colonies grown, clonal DNA purified, and the sequence was confirmed. This vector was referred to as Vector Sindbis-SCA. It is an expression vector which is used to make pseudotype non-replicating VSV with SCA on the viral surface as described below. It was used to make pseudotype VSV virus but it can be used to also make pseudotype virus with any other virus that expresses a glycoprotein on its surface. This construct was also placed into the VSV genome to make rrVSV whose only surface gp was the modified Sindbis gp.

Example 3

Creation of Vector Comprising EGFP
(MCS-EGFP-δ G/XN2)

The VSV-G gene was removed from the VSV genome and replaced it with the gene for enhanced green fluorescent protein(EGFP) and a multiple cloning site (MCS). The PCR protocol as detailed below was followed to create the following construct called PCR product #2:Mlu 1-MCS-Stop-Start-EG FP-Stop-Start-Nhe 1

The EGFP gene was amplified using PCR from vector EGFRPN-1 (Clontech, Palo Alto, Calif.) using the following primers to add a multiple cloning site containing Not 1 and Pme 1 restriction sites and VSV transcription stop and start signals (italics) in front of the gene for EGFP:
Forward primer: (SEQ ID NO:3)
gcgACGCGT cgtacggtaacctcgagaaagcggc-cgcgcgctttaaactatgaaaaaaactaacagagat
ccactatggtggtgagcaagggcga
Reverse primer: SEQ ID NO:4)
gcgGCT AGCcgtggatatctgt-tagttttttttcatactgagttacttgtacagctcgtcc The PCR product was ligated into a cloning vector, bacteria was transformed, clonal DNA was isolated and digested with Mlu1 and Nhe1, and the digested PCR product #2 was purified. XN2 (obtained from Dr. John K. Rose, Yale University School of Medicine) was digested with Mlu1 and Nhe1. The 14.4 kb vector was purified and the 1.6 kb insert was discarded. This vector was called Vector #2.

PCR product #2 was ligated with Vector #2, bacteria were transformed, colonies were grown, the clonal DNA purified and the sequence was confirmed. This vector was called Vector MCS-EGFP-δ G/XN2. It is an expression vector which is used to make pseudotype non-replicating VSV with SCA on the viral surface as described below. Appropriate glycoprotein genes can be placed in the Mlu1 or MCS or Nhe1 sites to create replicating recombinant VSV as described below.

Example 4

Creation of Vector Expressing Modified Sindbis gp and SCA (Sindbis-SCA/XN2)

The gene for Sindbis-SCA was inserted within the VSV genome. Plasmid pcDNA3.1 (Invitrogen, San Diego Calif.) was digested with Nhe1 and Hind III. The ends were blunted, religated, bacteria transformed, a clone was isolated and grown and the DNA was purified. This vector is referred to as Vector pcDNA3.1-Nhe1.

Sindbis-SCA was digested with BamH1 and the 3.9 kb insert was purified expressing the modified Sindbis gp with SCA and linkers. This insert was referred to as Sindbis-SCA. If there are BamH1 sites within the SCA, then a partial digest with BamH1 can be performed and the 3.9 kb band picked. Alternatively, site directed mutagenesis of the BamH1 sites can be performed.

The insert Sinbis-SCA was ligated with Vector pcDNA3.1-Nhe, and the bacteria was transformed. A clone was isolated in which the direction of vector insertion was 5'-Not1-insert-Pme1. The DNA was purified. The correct clone was confirmed by PCR and sequencing and this vector was referred to as Vector Sindbis-SCA/pcDNA3.1

Any SCA or ligand can be substituted into Vector Sindbis as follows. SCA/pcDNA3.1 by using PCR to place an Nhe 1 site at the beginning and a Cla 1 site at the end of the new SCA or ligand. The original Vector SindbisSCA/pcDNA3.1 is digested with Nhe1 and Cla1 and the new SCA or ligand is ligated in. The Vector Sindbis-SCA/pcDNA3.1 is digested with Not1 and Pme1 and the 3.9 kb insert is purified caliln-sert-Not1-Sindbis-SCA-Pme1.

The modified Sindbis gp gene is placed in the VSV genome as follows. The Vector Sindbis-SCA/pcDNA3.1 is digested with Not1 and Pme1 and the 3.9 kb insert is purified and called insert Not1-Sindbis-SCA-Pme1. Vector MCS-EGFP-δ G/XN2 is digested with Not1/Pme1 and the 13.5 kb band is purified. The insert-Not1-Sindbis-SCA-Pme1 is ligated with Vector MCS-EGFP-δ G/XN2. Bacteria are transformed, colonies grown, DNA purified and the correct clone is confirmed by PCR and/sequencing. This vector is called Vector Sindbis-SCA-GFPδ G/XN2. Sindbis-SCA is now in the VSV genome in place of the G gene. This method was used to place the gene for Sindbis-SCA-Her2 into the VSV genome and called Vector Sindbis-SCA-Her2-EGFP-δ G/XN2. The same method was used to place the gene for Sindbis-SCA-Her2 into the VSV genome containing the gene for GM-CSF and called Vector Sindbis-SCA-Her2-GMCSF-EGFP-δ G/XN2. Any SCA or ligand can be placed in this site by following the earlier direction to put the new SCA or ligand into Vector Sindbis-SCA/pcDNA3.1. The same targeting glycoproteins can be placed in any virus by placing InsertNot1-Sindbis-SCA-Pme1 within the genome of that virus.

Example 5

Creation of Vector Expressing GM-CSF
(GM-CSF-Sindbis-SCA-EGFP-δ G/XN2)

The mouse GM-CSF gene underwent PCR using primers that added an Mlu 1 site in front of the GM-CSF gene and stop and start signals followed by an Mlu 1 site at the end of the gene. This PCR product was digested with Mlu1 and ligated into the genome Vector MCS-EGFP-δ G/XN2 at the Mlu1 site.

Example 6

Creation of Non-Replicating VSV Expressing Only Sindbis-SCA

VSV pseudotypes were created by transfecting BHK-21 with either Sindbis gp or Sindbis-SCA-erbb2 gp. Two days later, the transfected BHK-21 was infected with non-replicating pseudotype VSV EGFP-δ G with VSV-G on the surface at an MOI of 6. This initial non-replicating pseudotype VSV EGFP-δ G with VSV-G on the surface was made by the methods detailed in paragraph 70. Supernatant containing virus was harvested one day following infection and stored at −70° C. All pseudotype viruses used were made in BHK 21 cells. Titers were determined by adsorbing the virus at different dilutions on the indicator cell line in wells of a 6-well tray (Corning Inc.) for 2 h, washing and replacing the media. Green cells were counted in an inverted fluorescent microscope (Axiovert 135, Carl Zeiss, Inc., Thornwood, N.Y.) 1 day later.

Example 7

Replicating Recombinant VSV (rrVSV) Expressing Only Sindbis-SCA

A fully infectious replicating VSV from vector components using the technique of Lawson and Rose was created. The following vectors were transfected simultaneously into BHK-21 cells: Vector Sindbis-SCA-EGFP-δ G/XN2 (or VectorGM-CSF:Sindbis-SCA-EGFP-δ G/XN2), pBS-P, pBS-L, pBS-N and pBS-G (the latter 4 vectors all obtained from Dr. John K. Rose, Yale University School of Medicine. One day later, these transfected BHK-21 were transfected with vaccinia, vTF-7. Two days later, supernatant was harvested which contains replicating recombinant VSV-Sindbis-SCA-EGFP-δ G or VSV-GMCSF-Sindbis-SCAEGFP-δ G. This virus was amplified by applying the supernatant to BHK-21 cells that have been transfected with a vector expressing VSV-G (e.g. CMV-VSV-G, obtained from Dr. Paul Robbins, University of Pittsburgh). The supernatant was harvested two days later and infected on cells recognized by the Sindbis-SCA such as SKBR3 or D2F2/E2 in order to make viral stocks. The supernatant was harvested two days later and titered on an indicator cell line. The virus harvested from this supernatant contained the VSV genome which had been deleted of the G gene and had either two extra genes: EGFP and Sindbis-SCA or 3 extra genes: GM-CSF, EGFP and Sindbis-SCA. The only glycoprotein expressed on the viral surface is Sindbis-SCA. This virus was referred to as rrVSV-Sindbis-SCA or rrVSV-GM-CSF-Sindbis-SCA. Titers were determined as detailed for pseudovirus, except that after 2 h of viral adsorption the media was replaced with media containing 30 nM Bafilomycin A1 to avoid counting newly produced virus. The same technique was used to make non-replicating pseudotype VSV EGFP-δ G with VSV-G employed in paragraph 69 as follows: EGFP-δ G/XN2, pBS-P, pBS-L, pBS-N, and pBS-G were transfected into COS-7 cells and infected at MOI=6 with vTF-7, a vaccinia virus expressing T7 polymerase (NIH AIDS research and reference reagent program, Rockville, Md.). Virus were harvested from the supernatant 2 days later and amplified on BHK 21 cells that were transfected with CMV-VSV-G using a standard lipofectamine protocol.

Inhibition of viral titer by antibody to erbb2 was determined by incubating cells at 4° C. first with antibody for 30 min and then with virus and antibody for 60 min. This temperature was chosen to prevent antibody capping and endocytosis into the cell. The cells were then incubated overnight at 37° C. and the titer measured at 24 h. The percent inhibition was 1−(titer with antibody)/(titer without antibody)×100.

Viral RNA was harvested, converted to cDNA using RT-PCR and sequenced to prove that the gene for Sindbis-SCA-erbb2 was appropriately placed in the VSV genome.

Growth of replicating virus was determined by adsorbing the virus at MOI=0.005 for 2 h on the indicator cell line, plated at 2×10⁵ cells in one well of a 6 well tray, washing three times, replacing the media and counting green cells in an inverted fluorescent microscope every 6 h for 24 h. The number of infected cells could not be accurately counted after this time because of cell clumping and lysis of early infected cells. Cytopathic effect (CPE) was determined by adsorbing the virus on the indicator cell line in one well of a 6-well tray at MOI=10 for 2 h, washing, replacing the media and harvesting all cells after 1 day. The number of live cells in the virus infected well was divided by the number of live cells in a no virus control well and multiplied by 100 to determine the percentage of living cells following treatment. The percent CPE was 100 minus this number.

Example 8

Flow Cytometry

SKBR3 cells, 4×10⁵/well, and 143 cells, 2×10⁵/well, were plated simultaneously individual wells of 6 well tissue culture trays (Corning Inc., Cat#3516, Corning, N.Y.). These cell numbers were chosen because we knew from previous experience that in 24 h, the wells would be nearly confluent with about equal numbers of adherent cells of the two cell lines. Cells were infected with rrVSV expressing Sindbis-SCA-erbb2 at MOI=1 and harvested 8 h later. Cells were analyzed 8 h after infection before many infected cells expressed green fluorescence because at later times cell death interfered with interpretation of the assay. Flow cytometry was performed by incubating the cells with 100 Al of anti-erbb2 MAb 4D5 and then staining with a R-Phycoerythrin-conjugated goat anti-mouse IgG antibody (Sigma P9670, St. 385 Louis, Mo.). Immunofluorescence was quantified using a FACStarPlus cytometer (Becton Dickinson, Mountainview, Calif.). All cells were included in the analysis.

Example 9

Analysis of the Protein Composition of Pseudotype and Replicating VSV and Infected Cells Preparation of $^{35}$S-labeled virus was performed as previously described with modifications (Whitaker-Dowling et al., 1983). VSV pseudotypes were created by transfecting BHK 21 with DNA encoding either Sindbis gp or Sindbis-SCA-erbb2 gp. Twenty-four hours after transfection, the media was removed from each well and replaced with 1 ml of cysteine/methionine free media (Cat#523 19050-121, Gibco/BRL,) containing 20 ACi/ml of 35S-methionine (Trans$^{35}$S-LABEL, 10 mCi/ml, ICN Biochemicals, Irvine, Calif., Cat#51006). Forty-eight hours after transfection, the cells were infected by the addition of VSV-EGFP-DG coated with G gp at a multiplicity of infection (MOI) of 5. After a 2-h adsorption period, the inoculum was removed and the cells refed with 1 ml of cysteine/methionine-free media containing 20 ACi/ml of 35S-methionine. Seventy-two hours after transfection, the media containing the radiolabeled virus was harvested, and the cell debris removed by centrifugation at 1000×g for 5 min. The virus in the supernatant was then pelleted by ultracentrifugation in a swinging bucket rotor at 80,000×g for 2 h. The virus pellets were resuspended in 200 μl of complete medium and layered on a 10% to 40% sucrose gradient containing 10 mM Tris pH 7.4, 1 M NaCl, and 1 mM EDTA. The gradient was subjected to ultracentrifugation in a swinging bucket rotor at 35,000×g for 90 min. The radiolabeled viral band was collected and diluted to 33 ml with serum-free medium and repelleted by ultracentrifugation as described. The virus pellet was resuspended in 200 µl of serum-free medium. The purified radiolabeled virus was diluted 1:1 with 2× Laemmli sample buffer and subjected to analysis by sodium dodecyl sulfate polyacrylamide gel electrophoresis using 10% acrylamide containing 0.09% bis acrylamide (Laemmli, 1970). The gel was dried under vacuum and examined by autoradiography. Viral bands were identified by their molecular weights. Viral yield following this extensive purification was low accounting, in part, for the inability to visualize the VSV P protein. Similar techniques were used to prepare 35 S-labeled recombinant replicating VSV whose surface gp was Sindbis-SCA-erbb2 or wt VSV G. Two hours after infection of SKBR3 cells in individual wells of a 6-well tissue culture tray (Corning Inc.) with either wt VSV or rrVSV at MOI=6, the media was removed and replaced with 1 ml of cysteine/methionine free media containing 20 ACi/ml of 35S-methionine. The media containing the radiolabeled virus was harvested 24 h after infection and the cell debris removed by centrifugation at 1000×g for 5 min. The virus in the supernatant was then pelleted and subjected to gel electrophoresis as above. Analysis of cellular proteins following viral infection was performed by infecting D2F2/E2 cells in individual wells of a 6 well tissue culture tray with rrVSV at MOI=1. At various times, individual wells were labeled for 2 h with 35S-methionine as above. The cell layer was then lysed in 2×Laemmli sample buffer and subjected to gel electrophoresis.

Example 10

Figure 1B:
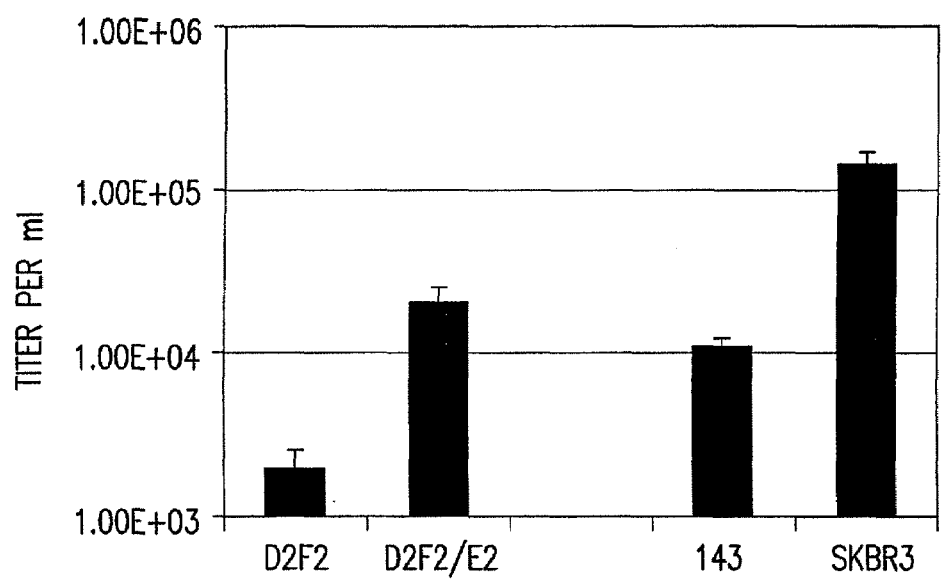
Figure 2:
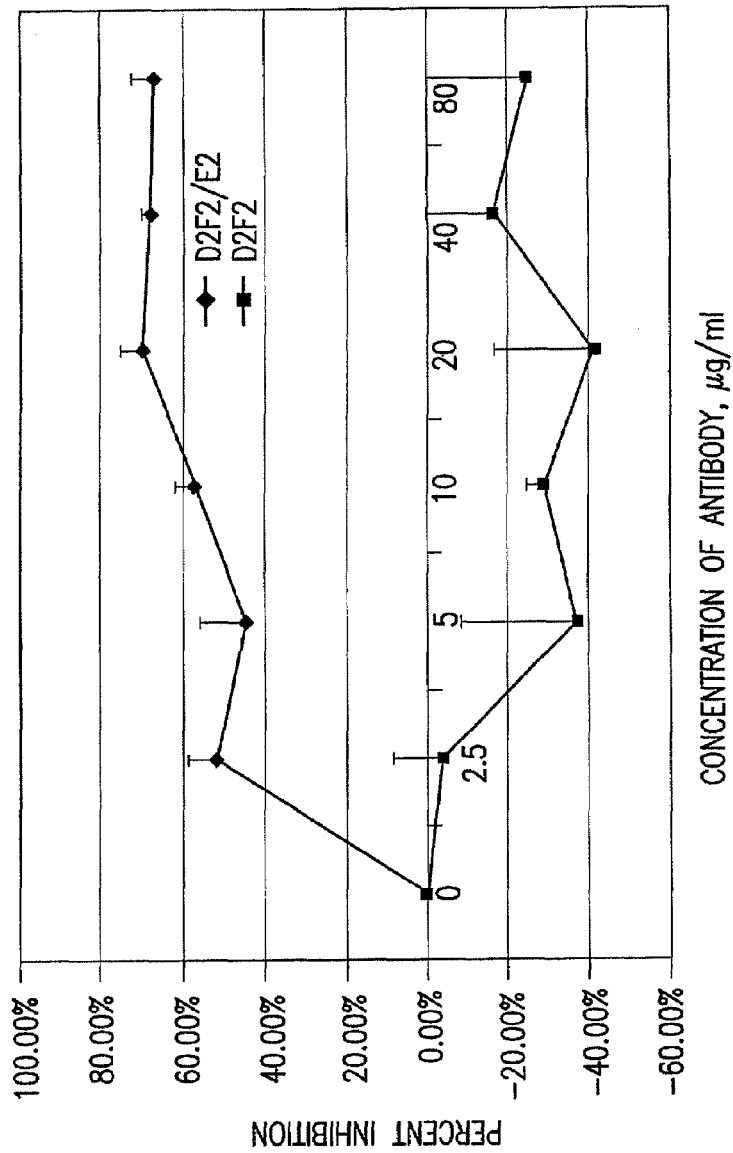
FIG. 2 shows a graph demonstrating the inhibition by anti-erbb2, Herceptin, of titer of pseudotype VSV coated with Sindbis-SCA-erbb2 gp on D2F2 and D2F2/E2 cells. Mean of two experiments with standard error bars. X-axis is log scale.

Non-Replicating Pseudotype VSV Coated With Sindbis-SCA-Erbbs GP Specifically Infects Her2/NEU Overexpressing Cells The goal was to develop VSV for clinical use in cancer therapy by restricting its tropism to cells that over-express the Her2/neu receptor. To this end, a recombinant VSV (rVSV) genome was constructed in which the G gene was replaced by a gene encoding green fluorescent protein (EGFP-DG/XN2). This construct was used to create a non-replicating virus whose genome consisted of rVSV-EGFP-0394,20G and whose surface protein, supplied in trans by transfection, was either Sindbis-SCA-erbb2 or wt Sindbis gp. Titers of these viruses were easily determined by infecting a target cell line and counting green cells 1 day later. Titers were determined on two pairs of cell lines, SKBR3 versus 143 cells and D2F2/E2 versus D2F2 cells. SKBR3 is a human breast cancer line that highly expresses Her2/neu and 143 is a human osteosarcoma cell line that does not express Her2/neu. D2F2/E2 is a mouse mammary cancer cell line that has been stably transfected with a plasmid expressing human Her2/neu and D2F2 is the parent cell line. Infection with pseudotype rVSV-EGFP-DG coated with wt Sindbis gp showed no specificity for Her2/neu expressing cells and yielded similar titers in both cell lines from each pair (FIG. 1A). On the other hand, pseudotype rVSV-EGFP-DG coated with Sindbis-SCA-erbb2 gp showed a greater than 10-fold better titer on the cell line in each pair that expressed Her2/neu (FIG. 1B). Incubation of the virus in the presence of Herceptin, an antibody directed to the erbb2 receptor on the cell surface, reduced titer on D2F2/E2, the cell line expressing erbb2 but had no effect on titer on D2F2, the parent cell line that did not express erbb2 (FIG. 2). Inhibition was antibody dose-dependent and reached a maximum of 69% inhibition at an antibody concentration of 20 ug/ml. An irrelevant antibody control had no effect. Inhibition by anti-erbb2 antibody may have been incomplete because, as suggested by others, the virus with multiple binding sites may have higher avidity for the receptor than the antibody (Martin et al., 2003). Also these antibodies bind to the cellular receptor and not to the virus and are therefore not directly neutralizing for the virus. Titer of the pseudotype rVSV-EGFP-DG coated with Sindbis-SCA-erbB2 gp was higher on the SKBR3 cells than the D2F2/E2 cells. One possible explanation was that SKBR3 cells expressed higher amounts of erbb2 on the cell surface than D2F2/E2 cells, as demonstrated by flow cytometry. The mean fluorescence on cells stained with the humanized anti-erbb2 monoclonal antibody Herceptin was 401 on SKBR3 cells, 186 on D2F2/E2 cells, and 12 on D2F2 cells. When titered on erbb2-negative cells, non-replicating pseudotype VSV coated with Sindbis-SCA-erbb2 had <3% the titer of pseudotype VSV coated with wild type Sindbis gp indicating that the chimeric Sindbis gp had severely impaired binding to the natural receptors (FIGS. 1A-B). The baseline titer of control VSV-EGFP-DG created without a surface gp was very low (<$10^3$/ml) and presumably represented residual inoculum virus used in the producer cells to create these various pseudotypes (Bergman et al. Vesicular stomatitis virus expressing a chimeric Sindbis glycoprotein containing an Fc antibody binding domain targets to Her2/neu overexpressing breast cancer cells. Virology 316, 337-347).

Example 11

Figure 3:
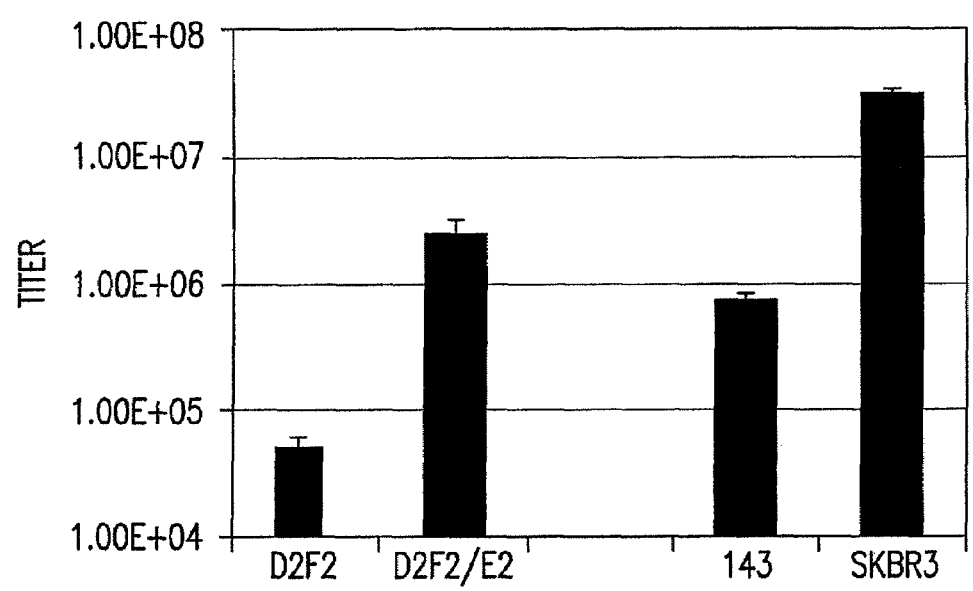
FIG. 3 shows a bar graph demonstrating the titer of replicating recombinant VSV-SCA-erbb2 on erbb2-expressing cell lines, SKBR3 and D2F2/E2, and non-erbb2-expressing cell lines, 143 and D2F2. The mean of three experiments are shown with standard error bars.
Figure 4A:
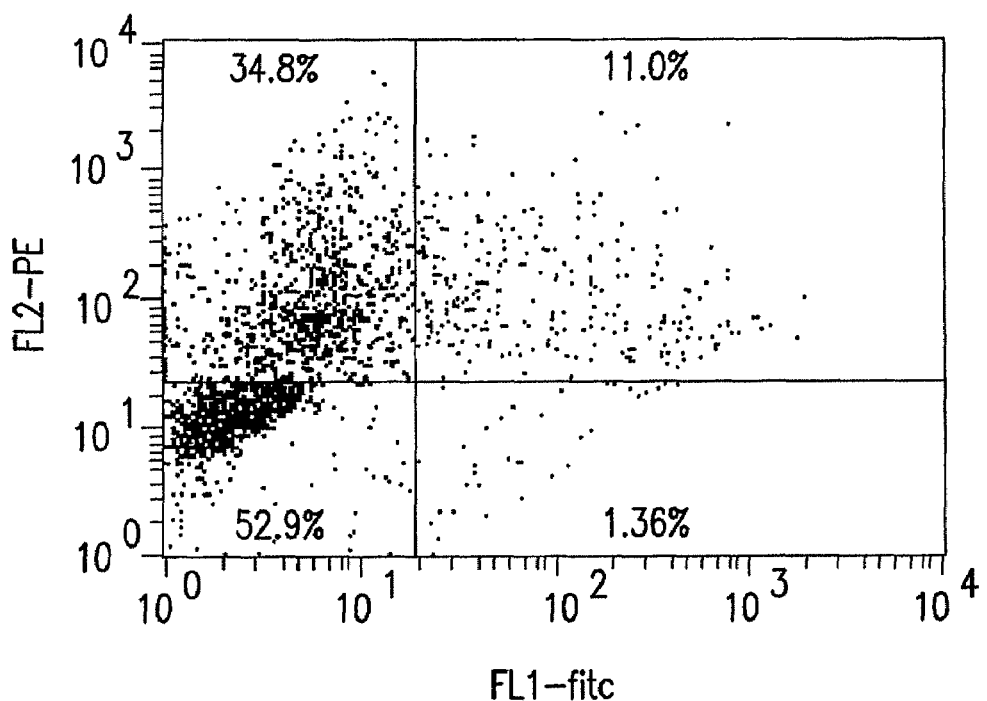
FIG. 4A shows flow cytometry analysis of a mixture of SKBR3 and 143 cells 8 hours after infection with MOI=1 with rrVSV expressing Sindbis-SCA-erbb2, where the cells are stained with anti-erbb2 Mab 4D5 followed by R-Phyco-erythrin-conjugated goat antimouse IgG antibody, showing that infected cells are positive for FL 1-Fitc (right quadrants) because the virus expresses EGFP. Erbb2 overexpressing cells are positive for FL2-PE (upper quadrants) Infected cells that are also erbb2 overexpressing are found in the upper right quadrant.
Figure 4B:
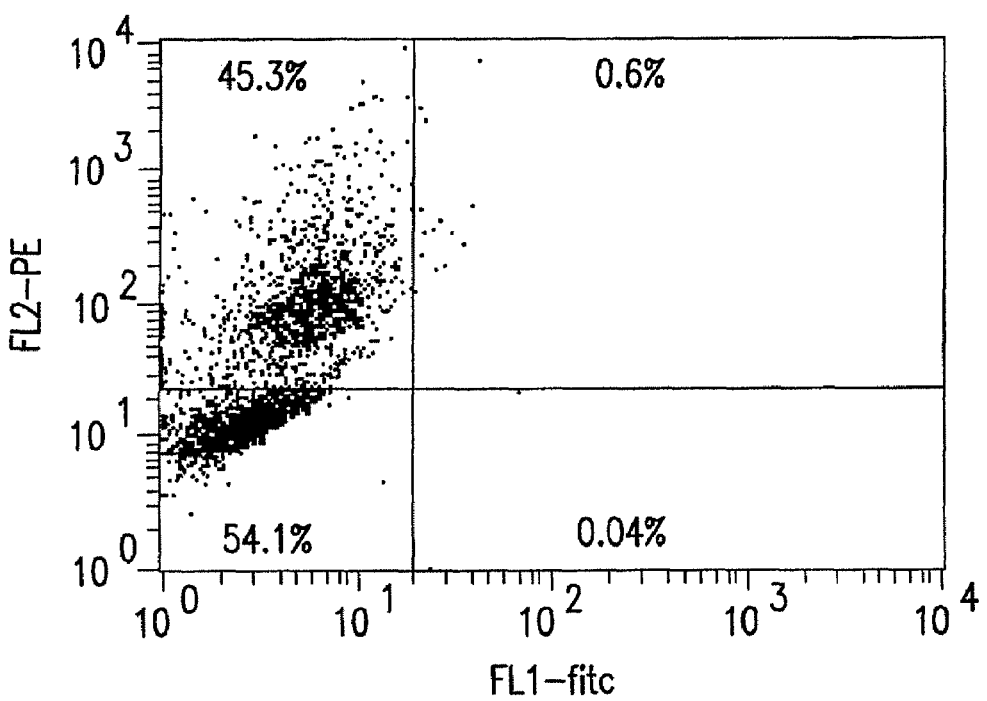
FIG. 4B shows the control plot of an uninfected mixture of SKBR3 and 143 cells stained with anti-erbb2 Mab 4D5.
Figure 5:
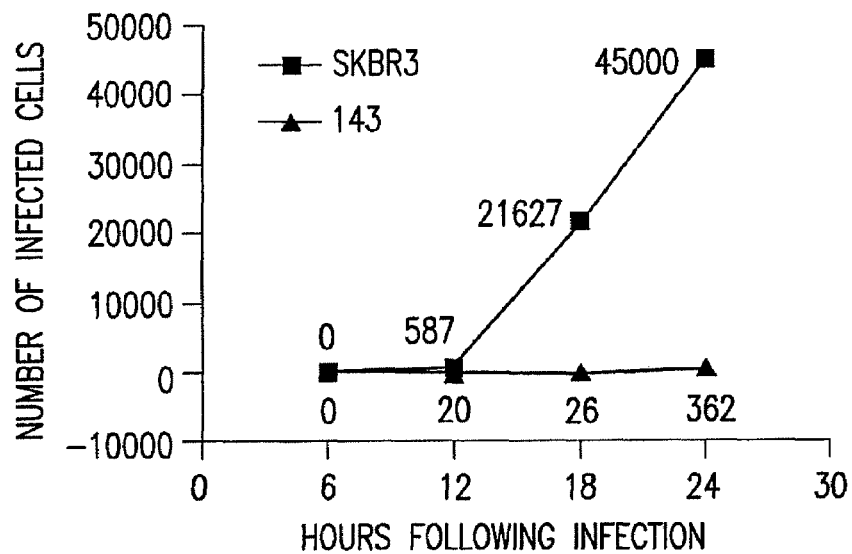
FIG. 5 shows a graph of the growth of replicating recombinant VSV-SCA-erbb2 in SKBR3 cells that express erbb2 and 143 cells that do not.

Replicating Recombinant VSV Expressing Sindbis-SCA-Erbbs GP Specifically Infects Her2/NEU Overexpressing Cells Once the inventors knew that Sindbis-SCA-erbbB2 gp targeted to the Her2/neu receptor, a recombinant VSV (rVSV) genome in which the G gene was replaced by a gene encoding Sindbis-SCA-erbb2 as well as a separate gene encoding green fluorescent protein were constructed (Sindbis-SCA-erbb2-EGFP-DG/XN2). A replication-competent VSV virus was created from this genome, which contained the gene expressing Sindbis-SCA-erbb2 in the viral genome and whose only coat proteins were the Sindbis derived E1 and Sindbis-SCA-erbb2 gp. This virus was called rrVSV-Sindbis-SCA-erbb2 and showed targeted infection of Her2/neu expressing SKBR3 and D2F2/E2 cells (FIG. 3). The titer of the rrVSV was >40-fold better on the cell line in each pair that expressed Her2/neu. Two color flow cytometric analysis demonstrated that when rrVSV expressing Sindbis-SCA-erbb2 was incubated with a mixed culture of SKBR3 and 143, 25% of the Her2/neu over-expressing SKBR3 were infected compared with 2.5% of the 143 cells (FIG. 4). In addition to specific targeting, rrVSV-expressing Sindbis-SCA-erbb2 also displayed specific replication (FIG. 5) and killing in Her2/neu expressing cells. The cytopathic effect of rrVSV was measured in cells that did and did not express Her2/neu and based on trypan blue exclusion 1 day after infection at MOI=0.5 was 92.1% in SKBR3 cells and 7.7% in 143 cells.

Example 12

Stability and Concentration of Viral Particles

In the future, clinical applications of this virus may require concentration and storage. rrVSV was reasonably resistance to freeze/thaw. Two freeze/thaw cycles of the virus produced a 21% loss of titer for wt VSV and a 39% loss of titer for rrVSV expressing Sindbis-SCA-erbb2. rrVSV expressing Sindbis-SCA-erbb2 could be easily concentrated 40 fold by filtration (Centricon-Plus-20 Centrifugal Filter Device with Biomax membrane, 100 K NMWL, Millipore Corp., Billerica, Mass.). Further concentration was not attempted. Filtration concentrated the virus from 36 ml with a titer of $1.44 \times 10^6$/ml to 0.5 ml with a titer of $5.7 \times 10^7$/ml. Recovery rate was 55%.

Example 13

Endosomal Ph Dependence

Figure 6:
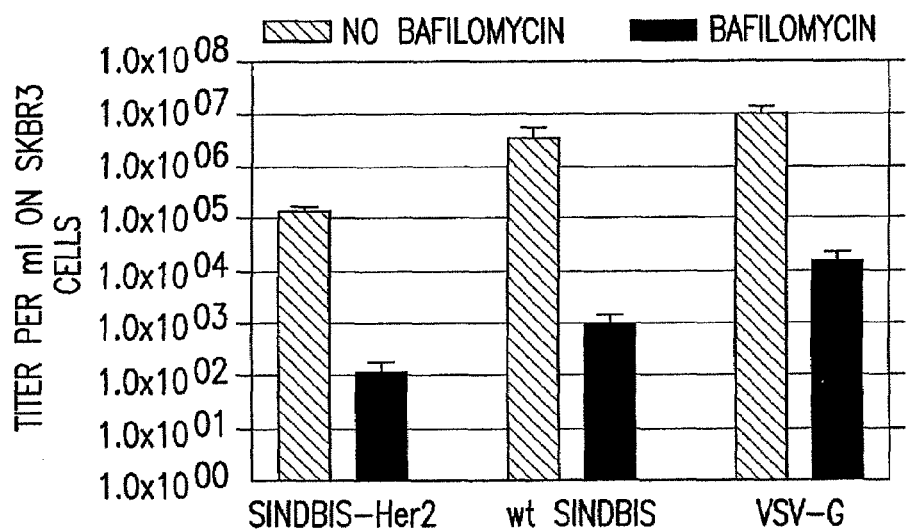
FIG. 6 shows a bar graph of the inhibition of bafilomycin Al of titer on SKBR3 cells of pseudotype VSV-EGFP-ΔG, wt Sindbis or Sindbis-SCA-erbb2. The mean of three experiments with error bars are presented.
Figure 7:
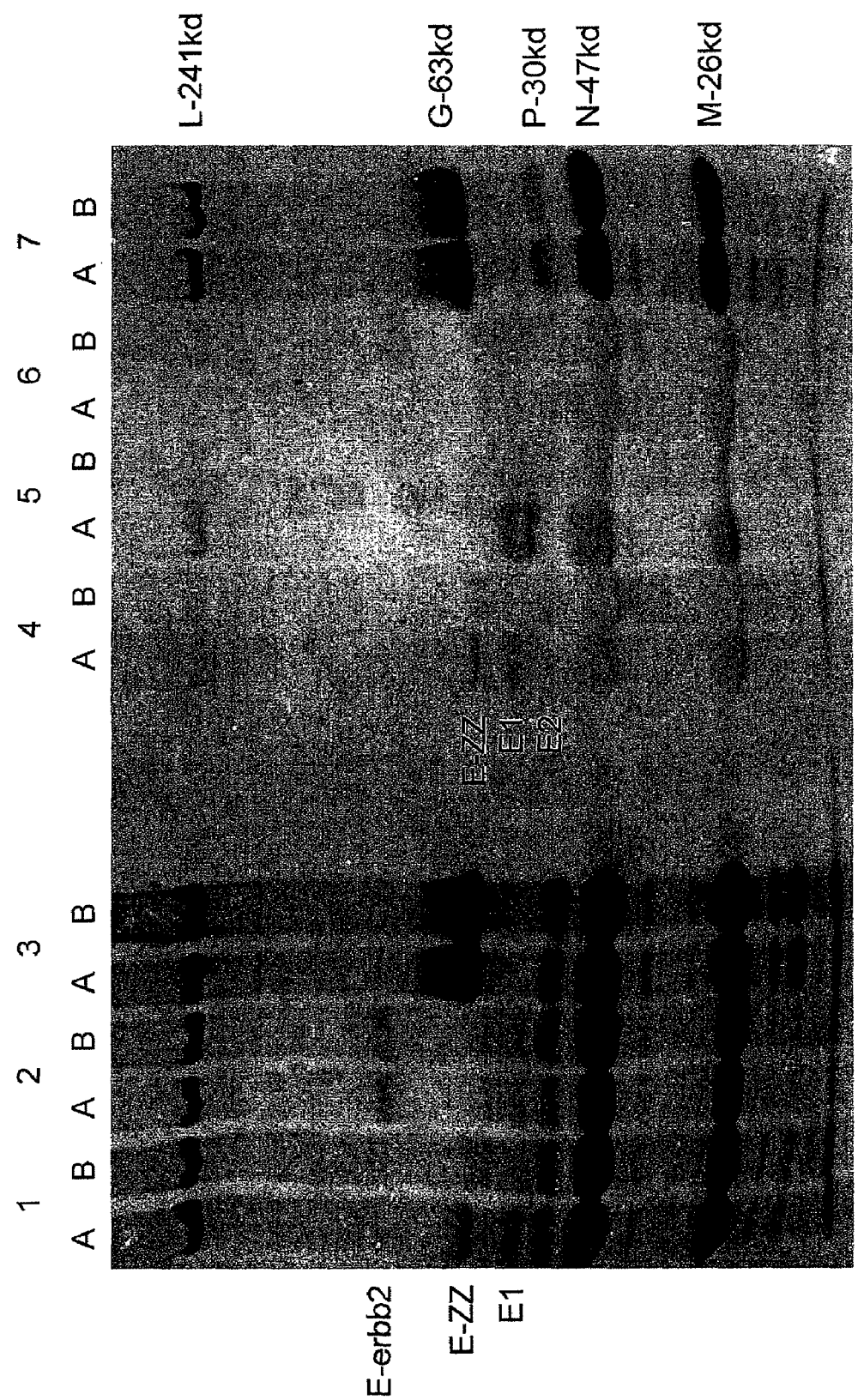
FIG. 7 shows a SDS-PAGE gel of recombinant viruses metabolically labeled with $^{35}$S-methionine, where pseudotypes were made in BHK 21 cells and wt VSV and rrVSV were grown in SKBR3 cell prepared at 32° C. (lane A) or 37° C. (lane B). The lanes contain the following viruses (1) rrVSV expressing Sindbis-AA, a modified Sindbis gp with the addition of 0.438 kb coding for two synthetic IgG Fc-binding domains (2) rrVSV expressing Sindbis-SCA-erbb2, a modified Sindbis gp with the addition of 0.867 kb coding for the SCA and linkers (3) wt VSV (4) pseudotype VSV expressing Sindbis-ZZ, a modified Sindbis gp with the addition of 0.438 kb coding for two synthetic IgG Fc-binding domains (5) pseudotype VSV expressing wt Sindbis glycoprotein (6) pseudotype VSV expressing Sindbis-SCA-erbb2, a modified Sindbis gp with the addition of 0.867 kn coding for the SCA and linkers (7) wt VSV.

Studies to determine whether rrVSV having a new attachment protein would still enter its target cells via the endosome. Bafilomycin Al, a macrolide antibiotic, is a specific inhibitor of vacuolar-type H+-ATPase that blocks acidification of the endosome. Titers on Her2/neu over-expressing SKBR3 cells of pseudotype VSV coated with either wt VSV-G gp, wt Sindbis gp or recombinant Sindbis-SCA-erbb2 gp were determined in the presence of Bafilo-mycin, 30 nM. Bafilomycin blocked N99% of infection with all three viruses indicating that viral entry of the rrVSV was endosomal-dependent (FIG. 6). It was previously shown that this concentration of Bafilomycin did not inhibit infectivity of a pseudotype VSV coated with the F and HN gp of SV5 virus which entered the cell by direct fusion with the cell membrane (Bergman et al., 2003). Protein composition of the recombinant viruses. SDS-PAGE analysis of 35S-methionine radiolabeled pseudotype was performed and replicating recombinant viruses to confirm incorporation of the expected proteins into each virus. FIG. 7 demonstrates that all rrVSV contain the VSV proteins M, N, P, and L.

Protein composition of the recombinant viruses. SDS-PAGE analysis of 35S-methionine radiolabeled pseudotype and replicating recombinant viruses was performed to confirm incorporation of the expected proteins into each virus. FIG. 7 demonstrates that all rrVSV contain the VSV proteins M, N, P, and L. All the VSV proteins except for P are clearly visible. Most importantly, the rrVSV contain the expected Sindbis E1 and modified Sindbis E2 gp and do not contain VSV G gp. Comparison of viruses expressing wt Sindbis E2, Sindbis E2 modified to express ZZ and Sindbis E2 modified to express SCA-erbb2 shows the expected higher migration of the E2 protein as larger inserts are added to the gene. Sindbis-ZZ adds 0.438 kb coding for two synthetic immunoglobulin G (IgG) Fc-binding domains, whereas Sindbis-SCA-erbb2 adds 0.867 kb coding for the SCA and linkers. The unmodified E1 band remains the same size in the three viruses. Protein analysis of the rrVSV demonstrates poor incorporation of modified Sindbis glycoprotein into the rrVSV particles compared with wt VSV particles (FIG. 7). The difference in labeling intensity is not an artifact of amino acid composition because the number of methionine amino acids in VSV-G, Sindbis E1 and Sindbis E2 are similar. Possible explanations for the difference include variations in gp synthesis, transport or viral incorporation. FIG. 7 demonstrates that wt Sindbis and Sindbis-ZZ gp incorporation into virus were better when virus was prepared at 32 than 37° C., suggesting a problem in protein transport. Incorporation of Sindbis-SCA-erbb2 was not temperature-dependent but was poor in the replicating virus and not visible in the pseudotype virus. A block in protein trafficking that is not relieved at lower temperature may explain the poor incorporation of Sindbis-SCA-erbb2.

Figure 8:
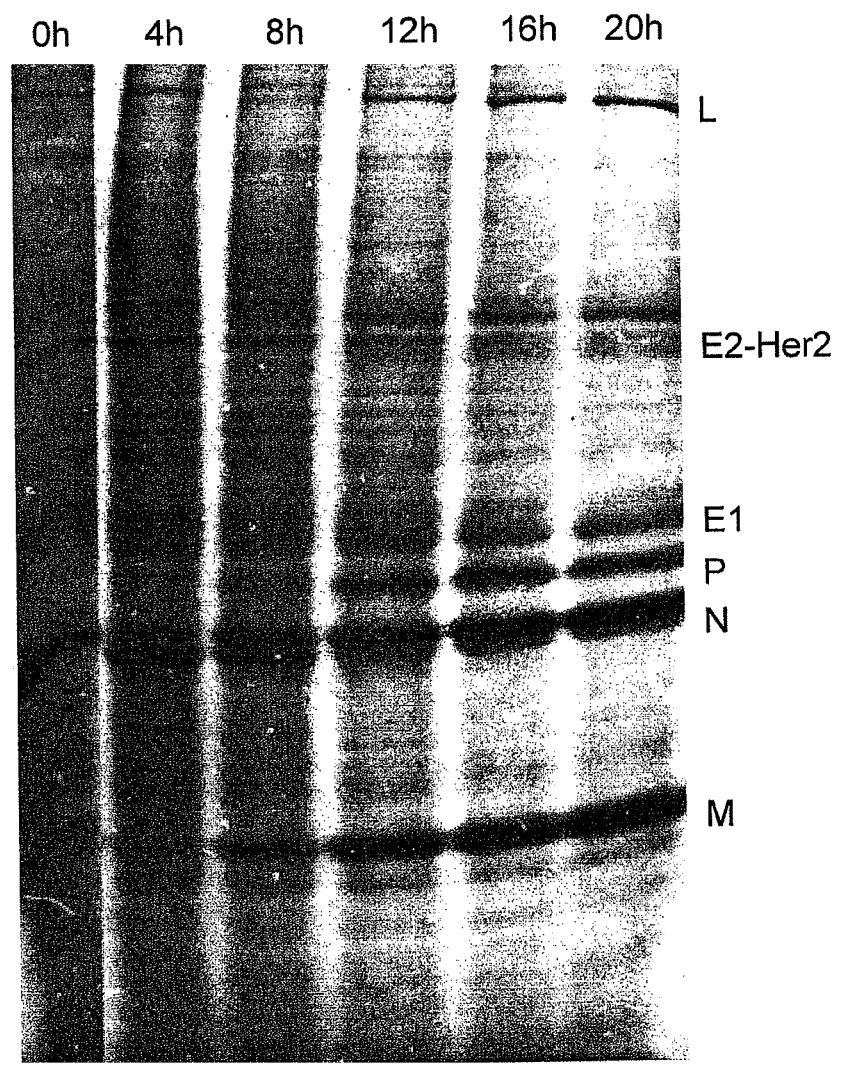
FIG. 8 shows a SDS-PAGE gel of cell extracts prepared at various following infection of D2F2/E2 cells with rrVSV expressing Sindbis-SCA-erbb2, where the cells were metabolically labeled with $^{35}$S-methionine. The wt VSV proteins are used as molecular weight markers.
Figure 9:
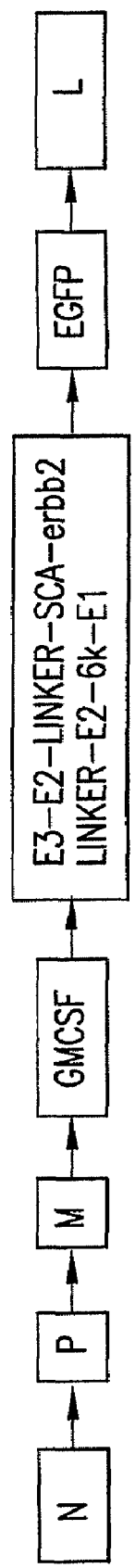
FIG. 9 shows the gene structure of the VSV expressing Sindbis-SCA-erbb2.

To examine modified Sindbis gp synthesis, SDS-PAGE analysis of cell extracts was prepared at various times following infection of D2F2/E2 cells with rrVSV expressing Sindbis-SCA-erbb2 was performed (FIG. 8). The modified E2 gp was synthesized appropriately, and as expected, there are two bands for the gp with the slightly larger band representing a precursor protein. Purified virus, as shown in FIG. 7, contains only the lower band. Cell lysate from virus infected cells treated with monensin, GolgiStopk, 0.66 Al/ml, (Cat. No. 2076KK, BD Biosciences) contains only the upper band because processing through the Golgi is interrupted (data not shown) (Sariola et al., 1995; Watson et al., 1991).

Example 14

Identification of Mutations Involved in Improved VSV Phenotype

Figure 12:
FIG. 12 shows an SDS-PAGE analysis of radiolabeled viral protein, where lane 1 is wt VSV, lane 2 is rrVSV created in SKBR3 cells, lane 3 is adapted rrVSV.

Serial passage of rrVSV expressing Sindbis-SCA-Her2 results in a virus with improved titer and better expression of gp on the viral surface. A single pass of the newly created rrVSV in SKBR3 cells, a human breast cancer line that over-expresses Her2/neu, reverted the phenotype of the surface glycoprotein from temperature sensitive to temperature insensitive. Serial passage for 15 passes on D2F2/E2 cells, a mouse mammary carcinoma cell line stably transfected with human Her2/neu increased viral titer from an initial value of $2 \times 10^5$/ml to a final titer of $2.3 \times 10^7$/ml. Radiolabeling studies showed that the rrVSV adapted to D2F2/E2 produced an altered E2 protein with improved ability to become incorporated into the viral envelope (FIG. 12). RT-PCR of genomes from the adapted viruses identified the following mutations associated with the improved phenotype.

| Phenotype | Mutations |
|---|---|
| Temperature insensitive | Amino Acid 55 in E2 (Glu to Arg) |
|  | Amino Acid 246 in E2 (His to Arg; position 535 of construct) |
| Improved gp incorporation in viral envelope | Amino Acid 52a in SCA (Pro to Leu; position 267 of construct) |
|  | Amino Acid 78 in SCA (Ala to Thr; position 293 of construct) |

Site directed mutagenesis was performed to create these mutations in the plasmid coding for the modified Sindbis gp, and make pseudotypes to prove that these mutations are responsible for the new phenotypes.

Analysis of the mutations in the adapted gp indicated two possible causes for the slower electrophoretic mobility of the adapted gp. The ala78thr mutation produced a potential O-glycosylation site on the new threonine and also changed the amino acid sequence from Asn-Thr-Ala to Asn-Thr-Thr thereby creating an N-glycosylation consensus sequence (Asn-X-Ser/Thr). The difference in electrophoretic mobility of the adapted gp was completely eliminated by treatment with PNGase, an enzyme that cleaves N-glycosylated sugars, indicating that the new N-glycosylation site in the adapted gp accounted for the difference in size of the glycoproteins. An additional O-glycosylation was excluded by demonstrating that creating the different pseudotypes in IdlD cells had no effect on the difference in size between the initial and the adapted gp. ldlD cells are unable to O-glycosylate in the absence of supplemental GalNAc and Gal (Zanni et al., 1989). If the adapted gp had an additional O-glycosylation, growth in ldlD cells would have reduced the difference in size between the two gp.

Example 15

In Vivo Therapeutic Model

D2F2/E2, a BALB/e mouse breast cancer cell line stably transfected to express the Her2/neu receptor was implanted into the peritoneum of Balb/c mice. One day later, mice were treated either with either targeted virus expressing GM-CSF, Sindbis-SCA-erbb2-GMCSF-EGFP, $1 \times 10^8$ PFU, or conditioned media. The virus is injected into the peritoneum in a large volume to ensure access of the virus to tumor deposits throughout the peritoneal space. Mice were sacrificed when they developed ascites. To date, viral toxicity in our treated animals has not been observed.

Figure 10:
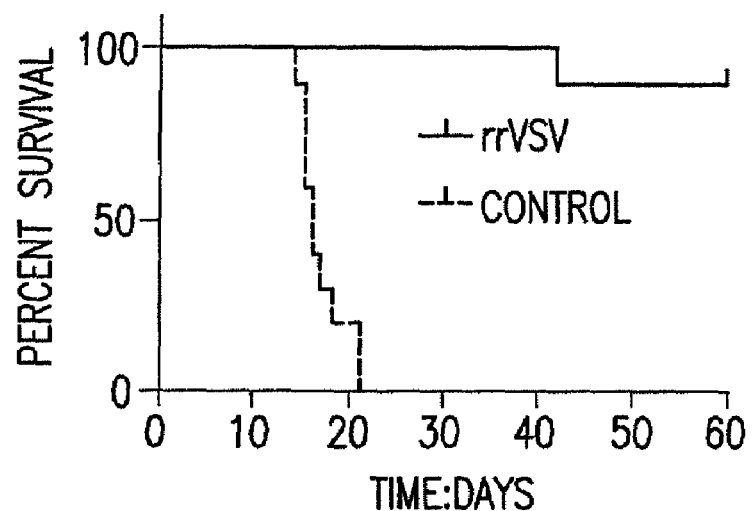
FIG. 10 shows the survival curves of mice injected with a Her2/neu-expressing cell line, D2F2/E2, that has been treated with a VSV-Sindbis-SCA.

Ten mice have been treated in each group and the survival curves (FIG. 10) show a significant benefit with virus treatment (log rank statistic p<0.00001).

Figure 11:
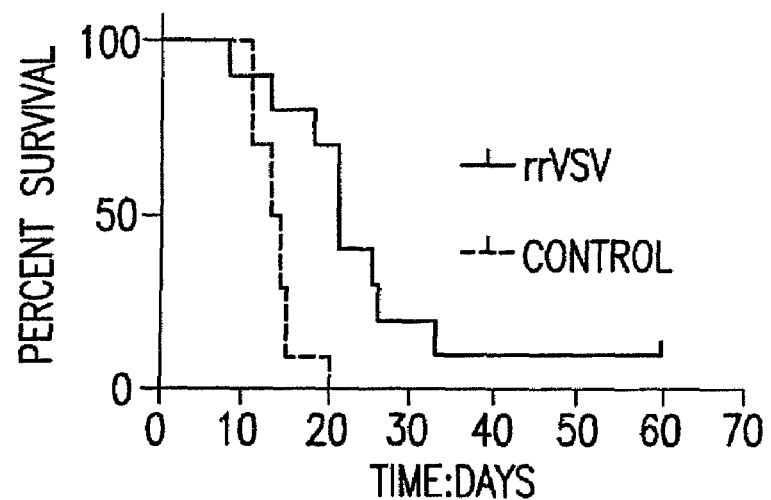
FIG. 11 shows the survival curves of mice injected with a non-Her2/neu-expressing cell line, D2F2, that has been treated with a VSV-Sindbis-SCA.

The rrVSV therapy appears to be specific for Her2/neu expressing tumors, because the results in ten mice implanted with D2F2, which does not express Her2/neu, are not nearly as therapeutic (FIG. 11).

ELISA shows high GM-CSF expression by this virus. D2F2/E2 cells infected with Sindbis-SCA-Her2-GMCSF-EGFP yielded a GM-CSF concentration on the culture supernatant of 1060-1260 ng/ml, similar to that reported by others (Miller et al. 2004 Recombinant replication-restricted VSV as an expression vector for murine cytokines. Protein Expression & Purification, 33:92-103.)

Example 16

Assay of Adaptive Immunity, T-Cell Response To Tumor Therapy, and Spread of Virus in Blood The inventors tested for an anti-tumor memory immune response. Seven animals implanted with D2F2/E2 and treated with rrVSV surviving for 2 months were re-challenged with IP D2F2/E2. Three succumbed to peritoneal tumors and 4 survived without apparent disease for 3 months. These 4 animals were then challenged with IP D2F2 tumor. One developed tumor and 3 are long-term survivors. These findings suggest that rrVSV treatment has produced an anti-tumor memory immune response and that this response is directed and therapeutically effective against antigens on the parent D2F2 cells and not just the Her2/neu antigen. This immune response probably resides in T-cells.

Figure 14:
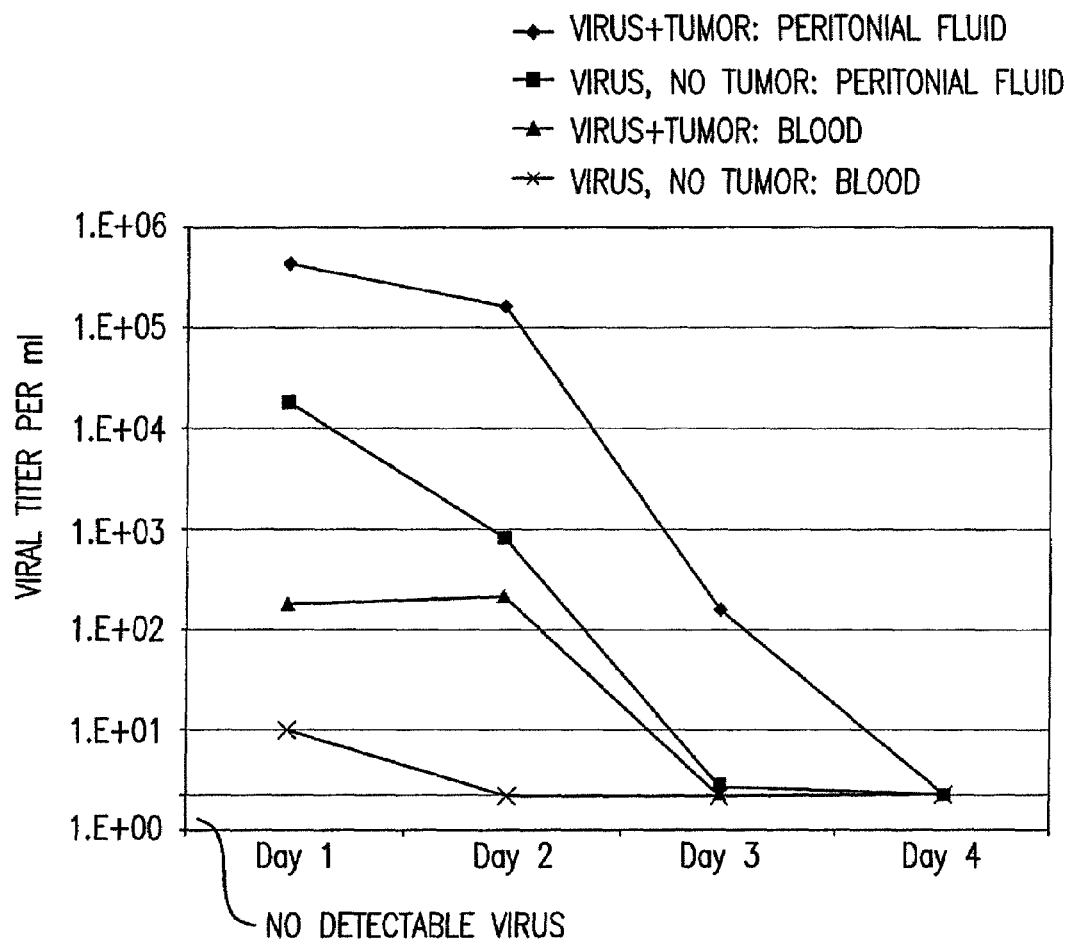
FIG. 14 shows titer of virus in peritoneal fluid and blood following IP administration of 1×10 ID VSV-Sindbis-SCA-Her2-GMCSF in animals with and without IP D2F2/E2 tumor. Mean of 5 values at each time point. The titer of virus in peritoneum and blood was more than 10 fold higher on day 1 in the animals who had tumor. Continued production of virus into the peritoneum and blood in the animals with tumor was evident between days 1 and 2.

Production and spread of rrVSV in vivo. FIG. 14 shows that rrVSV grew in peritoneal tumor and spread into the blood. The figure compares 2 groups of animals. One group received IP rrVSV 3d following IP tumor implantation and the other group received IP rrVSV into a naive peritoneum. Animals underwent peritoneal lavage and blood sampling daily for 5d following rrVSV administration with measurement of viral titers in the fluids.

The determination of the contribution of CD4 T-cells and CD8 T-cells to rrVSV therapy is performed by depleting the cells and then testing the previously successful therapy. These studies follow a similar design as the treatment trials recorded above. CD4 or CD8 T-cells are depleted by IP injection of 500 ug GK1.5 (anti-CD4) or 2.43 (anti-CD8) antibodies every other day for 3 doses and then 2x/wk. (Reilly, R. T., Gottlieb, M. B., Ercolini, A. M., Machiels, J. P., Kane, C. E., Okoye, F. I., Muller, W. J., Dixon, K. H., and Jaffee, E. M. 2000. HER-2/neu is a tumor rejection target in tolerized HER-2/neu transgenic mice. *Cancer Research* 60, 3569-3576).

The potency of this depletion regimen is tested by treating 2 naïve animals with 3 doses of antibody and then FACS analysis of splenocytes is performed. In addition, at the time of sacrifice, spleen cells are analyzed to confirm appropriate depletion of CD4 or CD8 T-cells. Control animals will receive injections of an irrelevant rat antibody. Ten animals are treated in each group. Initially, the CD4 or CD8 T-cells are depleted prior to tumor implantation and maintain depletion throughout the study. Although tumor-specific T-cells are not expected until at least 5d following implantation, it is possible that non-specific T-cells will be activated to combat tumor early after treatment. If these studies show interference with rrVSV therapy, then depletion is tested 5d after treatment. In anticipation that the major effect occurs with depletion 5d after treatment, the following parameters in animals undergoing depletion of CD4 or CD8 T-cells 5d after treatment are followed: direct tumor killing by CD4 or CD8 T-cells, presence of CD4 and CD8 cells in peritoneal fluid, presence of CD4 or CD8 cells associated with tumor in the mesentery. The basic design is as follows: Day 0:implant tumor; Day 3 (assuming SA1 shows >50% cure rate): rrVSV treatment; Day 8:deplete CD4 or CD8 T-cells; Day 15:sacrifice the animal. On the day of sacrifice, one study group undergoes peritoneal lavage, one has the mesentery harvested for paraffin embedding and one has mesentery harvested for embedding in OCT and freezing. Peritoneal cells are assayed for CD4 and CD8 T-cells by flow cytometry using the anti-CD4 MAb GK1.5 and the anti-CD8 MAb 53-6.7. Peritoneal cells are also be assayed for tumor specific cytotoxicity by using the following $^{51}$Cr-labeled tumor cells as targets: D2F2/E2, D2F2, CT26 mouse colon carcinoma, 143 human osteosarcoma. The effect of direct in vivo tumor killing by CD4 or CD8 T-cells are assessed by comparing area of tumor using quantitative image analysis of H&E stained slides of the entire mesentery. The presence of CD4 and CD8 T-cells associated with tumor are quantified by staining frozen sections of mesentery with anti-CD4 MAb GK1.5 and anti-CD8 MAb 53-6.7 and counting the number of CD4 and CD8 T-cells associated with tumor cells using image analysis. In each study, 5 animals have CD4 or CD8 T-cells depleted and 5 control animals have no depletion.

The contribution of NK cells to rrVSV therapy is also performed by depleting them and then testing the previously successful therapy. All treatment trials use the basic paradigm presented in preliminary results. $2 \times 10^6$ D2F2/E2 tumor cells in 0.1 ml PBS are implanted IP and the animals are treated a fixed number of days later with 1 ml of virus, IP. Experimental animals receive polyclonal antibody to asialo GM1, (Wako Pure Chem Industries, Richmond Va.) {Chen, Pham-Nguyen, et al. 2000 16/id}, 200 ug IP daily for 5d beginning 1d prior to tumor implantation and every 5d thereafter. The potency of this depletion regimen is tested by treating 2 naïve animals with rabbit polyclonal antibody to asialo GM1 daily for 3d and then analyzing spleen cells for the presence of NK cells with flow cytometry using the anti-NK cell MAb, DX-5. Control animals receive injections of an irrelevant rabbit antibody. Ten animals are treated in each group. In the first treatment trial, no other studies or procedures are performed with these mice. They are sacrificed when they develop ascites. Spleen cells are analyzed to confirm depletion of NK cells. If depleting NK cells has no effect on survival, then no further studies are done with this cell type. If depleting NK cells abrogates part or all of the therapeutic effect, then the requirement for NK cells early or late in the immune response and the direct tumor killing effect or an effect mediated through stimulation of T-cells are tested. To test whether NK cells are required early or late, a treatment trial in which NK cell depletion begins 5d after rrVSV therapy is performed. To test whether NK cells have a direct tumor killing effect, NK cells are depleted 1d prior to tumor implantation and the animals sacrificed 3d after rrVSV therapy. The area of the tumor in the mesentery between a group of 5 animals that are NK depleted is compared to 5 control animals using the histopathologic technique outlined in SA1.

The presence of NK cells in peritoneal fluid of rrVSV treated animals using flow cytometry and cytotoxicity assays is also tested. The basic treatment paradigm outlined above is used and animals are treated with either rrVSV or CM. UV-inactivated viruses are not used as the control because they are not inert. These viruses do not replicate, but may infect and transcribe some message, thereby provoking an IFN and immune response. Five animals are tested in each group. Peritoneal cells are harvested by lavage 3d after treatment and assayed for NK cells by flow cytometry using the DX-5 antibody and by cytotoxicity assays using 51 Cr-labeled D2F2/E2 cells as targets. Preliminary results show that treatment of peritoneal tumors with rrVSV stimulates an anti-tumor NK cell response.

The contribution of macrophages to rrVSV therapy by depleting them and then testing the previously successful therapy are tested. These studies follow the same design as detailed for NK cells above. Macrophages are depleted using Clodrolip (LCL), a liposomal drug preparations containing clodronate (Dichloromethylenebisphosphonic acid) (Laboratory of Liposomal Research, Zurich, Switzerland) administered at a dose of 200 ul IP 1d prior to tumor implantation and weekly thereafter. {Aichele, Zinke, et al. 2003 1/id} It is important to note that this regimen also depletes DC. The potency of the depletion regimen is tested by administering LCL and sacrificing 2 animals at 3d and 7d after treatment. The mesentery and associated lymph nodes are stained with the anti-mouse F4/80 antibody, BM8, the number of macrophages counted using image analysis and compare with untreated animals. Mice treated with empty liposomes or left untreated show the same phenotype, therefore untreated is an appropriate control. {Aichele, Zinke, et al. 2003 1/id} As with NK cells, the macrophages are initially depleted prior to tumor implantation. If depleting macrophages cells abrogates part or all of the therapeutic effect, then macrophages are tested for the requirement of an early or late in the immune response, whether they have a direct tumor killing effect or an effect mediated through stimulation of T-cells. To test whether macrophages are required early or late, a treatment trial is performed in which macrophages depletion begins 5d after rrVSV therapy. To test whether macrophages have a direct tumor killing effect, the macrophages are depleted 1d prior to tumor implantation and the animals sacrificed 3d after rrVSV therapy. The area of tumor in the mesentery between a group of 5 animals who are macrophage depleted is compared to 5 control animals using the histopathologic technique outlined in SA1. Isolation of macrophages by peritoneal lavage is unnecessary, because the tissue macrophages studies are tightly adherent cells, unlikely to be washed into the peritoneal fluid. The presence of macrophages are quantified in the mesentery following rrVSV therapy as follows. The basic treatment paradigm outlined above is used. Animals are treated with either rrVSV or CM and sacrificed 3d or 7d later. The mesentery and associated lymph nodes are stained with the anti-mouse F4/80 antibody, BM8, and the number of macrophages associated with tumor cells are counted using image analysis. The BM8 antibody is used with paraffin processed tissue, allowing H&E staining of sections adjacent to immunohistochemically stained sections and simplifying identification of tumor, inflammatory cells and normal tissue cells. Five animals in each group are compared.

Example 17

Animal Model Using Her2/neu Gene Under MMTV Promotor

Testing of the virus of the present invention occurs in additional animal models that more closely simulate human cancer. The disadvantage of the current model is that the implanted tumor cells are not fully autologous to the host animal. They were derived from the same inbred breed, but small variations may have been introduced in tissue culture. More clearly, the Her2/neu gene that has been stably transfected into these cells produces a protein foreign to the host that evokes an antibody response to the Her2/neu protein product. These differences do not result in tumor rejection. All of the untreated animals developed fatal peritoneal tumors.

Animal models of breast cancer in transgenic mice, FVB/N-TgN(MMTVneu)202Mul (The Jackson Laboratory, Bar Harbor, Me.) which express the non-activated rat Her2/neu gene under an MMTV promoter are developed. Seventy to 86% of these mice spontaneously develop focal mammary adenocarcinomas at a mean age of 205 to 234days. Lung metastasis develop in 38 to 72% of tumor bearing animals living to 8 months of age. Reilly, R. T., Gottlieb, M. B., Ercolini, A. M., Machiels, J. P., Kane, C. E., Okoye, F. I., Muller, W. J., Dixon, K. H., and Jaffee, E. M. 2000. HER-2/neu is a tumor rejection target in tolerized HER-2/neu transgenic mice. *Cancer Research* 60, 3569-3576; Chan, R., Muller, W. J., and Siegel, P. M. 1999. Oncogenic activating mutations in the neu/erbB-2 oncogene are involved in the induction of mammary tumors. [Review] [34 refs]. *Annals of the New York Academy of Sciences* 889, 45-51; Zelazny, E., Li, B., Anagnostopoulos, A. M., Coleman, A., and Perkins, A. S. 2001. Cooperating oncogenic events in murine mammary tumorigenesis: assessment of ErbB2, mutant p53, and mouse mammary tumor virus. *Experimental & Molecular Pathology* 70, 183-193). Her2/neu message and protein are highly expressed in the mammary tumors but not in adjacent normal mammary epithelium. A cell line, NT-2,derived from one of these spontaneious mammary tumors is employed to verify that therapeutic efficacy and viral kinetics in implanted peritoneal tumors are similar to the results established in Balb/c mice. An implanted pulmonary model which more closely simulates metastatic disease in humans is also employed. This model allows the optimization of intravenous viral therapy and determination of viral kinetics following virus administration into the blood stream. Intravenous injection of virus is clinically most useful. All tumors require a blood supply making all of them accessible by this route. Injection is simple and uniform. Theoretically, only small numbers of replicating virus are delivered to each tumor site, because the virus multiplies once infection occurs. Although the virus may be cleared rapidly from blood, if any reaches tumor and it replicates in tumor but not other tissue, then at 72 h there will be virus in tumor and not other tissue. Previous work has already shown that IV administration of VSV delivers virus to subcutaneous and pulmonary tumors. (Balachandran, Porosnicu et al., 2001b; Balachandran, Roberts et al., 2000; Balachandran & Barber, 2000; Balachandran, Porosnicu et al., 2001a)

The advantage of this model is that the tumor is fully autologous to the host animal. An rrVSV that contains an SCA specific for the rat neu product and not the human Her2/neu receptor product is created. The appropriate SCA called C11, obtained from Dr. Winifred Wels, is used here. A pseudotype VSV, whose only surface gp is Sindbis-C11, specifically infecting cells expressing rat neu is generated. The titers were $2 \times 10^6$/ml on TUBO cells and $6.7 \times 10^5$/ml on NT-2 cells which express rat neu compared with $4.9 \times 10^4$/ml on CT26 cells and $5 \times 10^4$/ml on 143 cells which do not express rat neu. The corresponding rrVSV is also prepared. Upon establishment of efficacy in transgenic animals implanted with NT2, this therapy in transgenic mice that spontaneously develop focal mammary Her2/neu expressing adenocarcinomas and lung metastases is tested. Primary mammary tumors in TgN FVB mice are surgically excised when they reach 1 cm in diameter. At that point, metastatic pulmonary tumors are predicted to be present in about 50% of animals. Success in this model supports the development of this therapy for human disease. This model system is slow and expensive, because animals must be bred and then watched until they spontaneously develop tumors, but is most likely to predict clinical utility. This model closely simulates human disease with slow growth of an endogenous tumor from an initial clone followed by multiple and progressive mutations133 and escape from any attempted host immune response. Pulmonary metastases are studied, and not focal mammary tumors, because in humans the primary breast tumor is easily treated surgically. The clinical problem is metastases.

It is certain that rrVSV infection will be curtailed by the host immune response. (Bachmann, M. F., U. Kalinke, A. Althage, G. Freer, C. Burkhart, H. Roost, M. Aguet, H. Hengartner, and R. M. Zinkemagel. 1997. The role of antibody concentration and avidity in antiviral protection. Science 276: 2024-2027). Because viral amplification and spread may determine therapeutic efficacy, rrVSV infection may be prolonged by temporarily disabling the host antibody response. This is likely to be effective, because the major adaptive immune response to VSV is neutralizing antibody production. (Kalinke, D., E. M. Bucher, B. Ernst, A. Oxenius, H. P. Roost, S. Geley, R. Kofler, R. M. Zinkemagel, and H. Hengartner. 1996. The role of somatic mutation in the generation of the protective humoral immune response against vesicular stomatitis virus. Immunity 5:639-652). The same strategy was successful in prolonging LCMV infection in mice. (Cerny, A., S. Sutter, H. Bazin, H. Hengartner, and R. M. Zinkemagel. 1988. Clearance of lymphocytic choriomeningitis virus in antibody- and B-cell-deprived mice. Journal of Virology 62: 1803-1807). It is also a legitimate therapeutic maneuver because it is safe clinically. (Igarashi, T., T. Ohtsu, H. Fujii, Y. Sasaki, Y. Morishima, M. Ogura, Y. Kagami, T. Kinoshita, M. Kasai, Y. Kiyama, Y. Kobayashi, K. Tobinai, and C. IDEe. 2001. Re-treatment of relapsed indolent B-celllymphoma with rituximab. International Journal of Hematology 73:213-221).

The potency of various rrVSV therapy is determined. All treatment trials use the basic paradigm presented above. $2 \times 10^6$ D2F2/E2 tumor cells in 0.1 ml PBS are implanted IP and the animals are treated a fixed number of days later with 1 ml of virus, IP. Control animals receive UV inactivated virus. No other studies or procedures are performed with these mice. Animals are sacrificed when they develop ascites. The presence of peritoneal tumor is confirmed by inspection of the peritoneum and histopathology. Ten animals are treated in each group because this study size is practical and sufficient to detect therapeutically relevant differences. (Bergman, Barmada et al., 1999; Bergman, Arbit et al., 1993) Power analysis using the log rank statistic on survival curves indicates that for n=10, one-tailed p=0.05, there is 90% power to detect a difference in survival from 0 to 0.5 and 80% power to detect a difference from 0.1 to 0.6. Animals that survive without apparent disease for 2 months are re-challenged first with D2F2/E2 cells and later with D2F2 cells to prove the presence of adaptive immunity.

Efficacy when rrVSV expressing GM-CSF is administered Id after tumor implantation has been proven. A trial using rrVSV expressing GM-CSF to treat 3d tumor implants is initiated. If treatment produces >50% survival, then the treatment of 7d tumor implants is performed. If treatment of 3d tumor implants shows <50% survival, then the treatment of 3d tumor implants with rrVSV expressing GM-CSF, rrVSV expressing IL-12 and rrVSV expressing no cytokine is performed. A dose response curve using varying PFU of the most effective rrVSV to treat 3d tumor implants is also performed. The dose of the most effective rrVSV is employed and compared to a single treatment with 3 and 5doses of rrVSV. All animals are treated on day 3 following tumor implant and some also receive therapy on days 5, 7, 9 and 11.

Tumor burden following treatment is also measured. Image analysis of the entire mesentery is performed to assess total tumor burden. Three day D2F2/E2 tumor implants are treated with either rrVSV, rrVSV expressing GM-CSF, rrVSV expressing IL-12 or conditioned media (CM). Animals are sacrificed on days 1, 2, 4, 7 and 10 following treatment and the entire mesentery is harvested. Five animals are analyzed at each time point in order to produce reliable mean data which is assessed by the standard error of the mean. Preliminary results show that on day 3 following implantation, all of the peritoneal tumor is in the mesentery. The entire tissue is harvested, mounted in paraffin and processed on a microscope slide depicting the entire mesentery. These images are captured on a video screen. Boundaries are hand drawn on the screen around every tumor nodule and Image Pro analysis software calculates the total tumor area. In addition, at the time of animal sacrifice, peritoneal lavage is performed with 5 ml of PBS. The number of tumor cells in the lavage fluid is determined by quantitative PCR and by flow cytometry. Flow cytometry is performed using live cells stained with the humanized anti-Her2/neu monoclonal antibody (MAb), Herceptin, followed by an anti-human FITC conjugated rabbit antibody. All cells are collected by centrifugation and DNA harvested.

These methods are much easier to perform and quantify than image analysis, but it is not clear that the number of tumor cells shed into the peritoneum will correlate with total tumor burden. The results obtained by these 3 methods are compared to determine whether flow cytometry or qPCR can substitute for image analysis in assessing total tumor burden. qPCR has the additional advantage that it can be performed on total DNA obtained from any tissue containing tumor and unlike flow cytometry does not require disaggregating tissue to obtain live cells.

Figure 13:
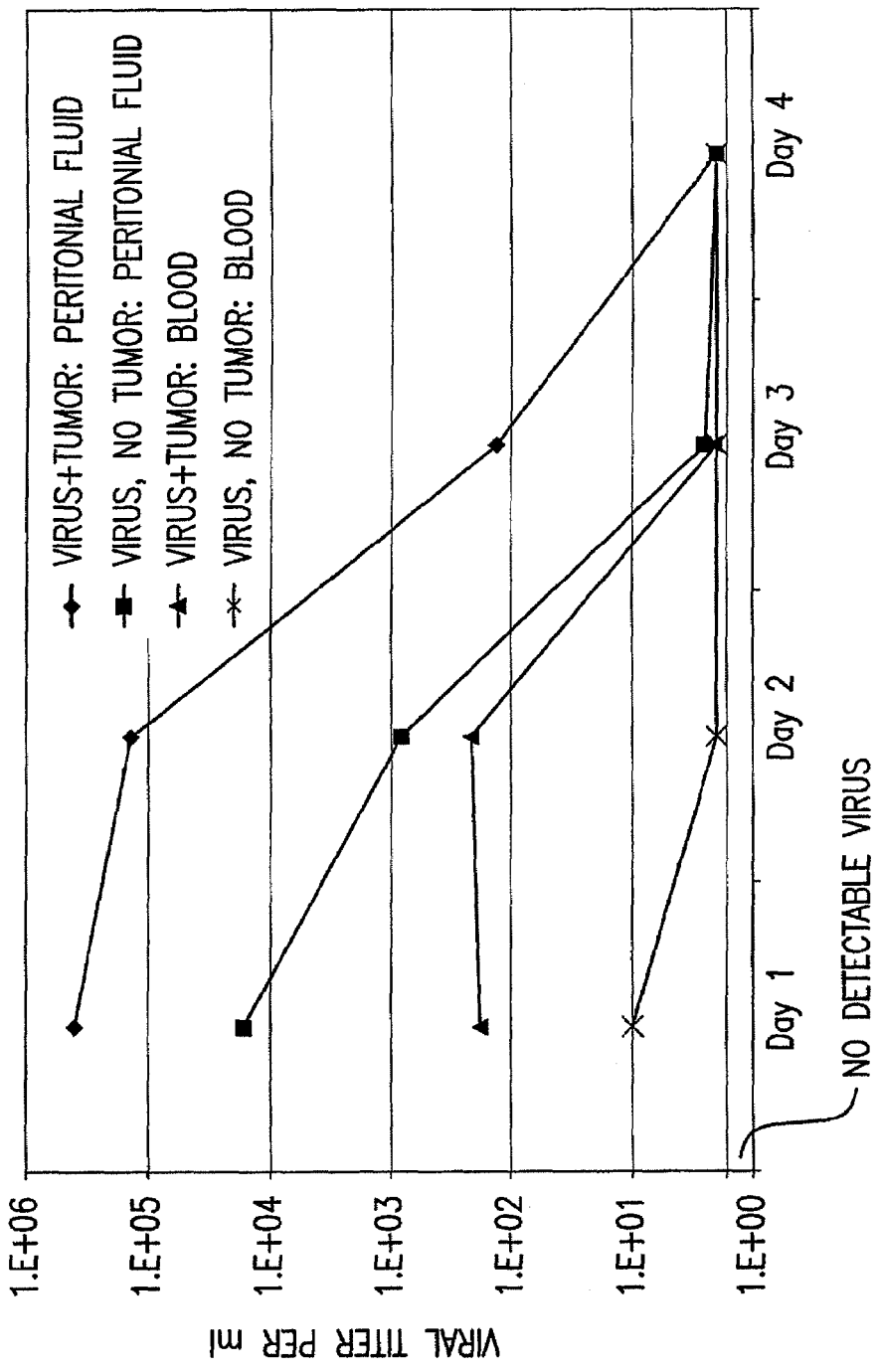
FIG. 13 shows a bar graph of the titer of virus in the peritoneal fluid and blood following administration of 1×108 PFU VSV-Sindbis-SCA-Her-GMCSF in animals with and without IP D2F2/E2 tumor, where each time point is a mean of five values.

Viral persistence is also measured. Preliminary results suggest that rrVSV treatment of peritoneal implants of D2F2/E2 cells result in viral production and shed into the peritoneum and blood for 2d following treatment (FIG. 13).

Peritoneal lavage and blood sampling to quantify viral persistence for each therapeutic rrVSV and viral persistence following multiple administrations is performed. VSV is known to be a strong inducer of type 1 IFN and this innate defense probably accounts for the disappearance within days after administration of rrVSV. rrVSV that express cytokines and those that do not is hypothesized to exhibit similar kinetics of disappearance. Elimination may be more rapid following multiple administrations because of the development of neutralizing antibodies.

Toxicity is assessed by histopathologic examination and assay of viral titer in various organs following rrVSV treatment. Three day D2F2/E2 tumor implants are treated with either rrVSV, rrVSV expressing GM-CSF, rrVSV expressing IL-12 or CM. Five animals receive peritoneal lavage, blood draw and are sacrificed 3d following treatment. The following organs are harvested: heart, lung, liver, spleen, kidney, small intestine and brain. A sample of each organ are emulsified in a Dounce tissue homogenizer (Bellco Glass, Inc., Vineland, N.J.) and viral titer is determined per gram of tissue for these organs as well as blood and peritoneal fluid. A sample from each organ is fixed in formalin, embedded in paraffin and received standard histopathologic examination of H&E stained slides. Five additional animals are sacrificed 7d following treatment and have histopathologic examination of the organs listed above. More extensive toxicity studies are not necessary until high therapeutic efficacy is firmly established.

T-cell response to tumor is also quantified. These experiments correlate in vitro measures of T cell response to tumor with therapeutic outcome. Two related hypotheses are tested in this experiment. The first hypothesis is that rrVSV that expresses GM-CSF or IL-12 elicits a greater T-cell response to tumor than rrVSV that express no cytokine. The second hypothesis is that the magnitude of the T cell response correlates positively with survival. Animals who do not attain a certain minimum T cell response do not achieve cure of their tumors. Several assays of T cell response are performed to find the one that correlates best with survival and can therefore serve as an in vitro surrogate marker of therapeutic response. This test is invaluable in clinical trials in humans to help decide who is responding to therapy and who requires additional therapy.

In vitro T-cell assays include EliSpot, multicolor flow cytometry, qRT-PCR and killing assays are performed. The advantage of EliSpot is high sensitivity. Multicolor flow cytometry labels cell markers such as CD4 or CD8 and intracellular cytokines such as IFNγ or TNFα on the same cells (Lamikanra, A., Z. K. Pan, S. N. Isaacs, T. C. Wu, and Y. Paterson. 2001. Regression of established human papillomavirus type 16 (HPV-16) immortalized tumors in vivo by vaccinia viruses expressing different forms of HPV-16 E7 correlates with enhanced CD8(+) T-cell responses that home to the tumor site. Journal of Virology 75:9654-9664; Lawson, N. D., E. A. Stillman, M. A. Whitt, and J. K. Rose. 1995. Recombinant vesicular stomatitis viruses from DNA [published erratum appears in Proc Natl Acad Sci USA Sep. 12, 1995;92(19): 9009]. Proceedings of the National Academy of Sciences of the United States of America 92:4477-4481). The advantage of this method is that it details which cell type has been activated. qRT-PCR is a more recent methodology that can be performed on freshly harvested T-cells to quantify MRNA message for IFNγ and TNFαc. High mRNA expression in these cells has been reported to correlate well with a therapeutic T-cell response (Perez-Diez, A., P. J. Spiess, N. P. Restifo, P. Matzinger, and F. M. Marincola. 2002. Intensity of the vaccine elicited immune response determines tumor clearance. Journal of Immunology 168:338-347). In addition to these assays which will detect a T cell response to any tumor antigen, soluble MHC-peptide tetramer reagents to specifically quantify T-cells that recognize the immunodominant antigen from rat neu, is used.

Functional activity of activated T-cells is tested in vivo and in vitro. In vivo assays consist of the following: measuring delayed type hypersensitivity (DTH) response to experimental versus control tumors and using flow cytometry to quantify the survival of CFSE labeled experimental and control tumors following intravenous injection. In vitro, T cells from treated animals as effectors in chromium release killing assays with experimental and control tumors as targets are used.

The antibody response to tumor and virus is quantified. The antibody response with survival is also correlated. Serum is tested for antibody to virus by virus neutralization assays and to tumor by flow cytometry using appropriate standard curves. Lindencrona et al. found no role for antibodies in immunologic rejection of Her2/neu expressing tumors following immunization but others have shown a therapeutic effect of anti-tumor antibodies. (Lindencrona, J. A., S. Preiss, T. Kammertoens, T. Schuler, M. Piechocki, W. Z. Wei, B. Seliger, T. Blankenstein, and R. Kiessling. 2004. CD4+ T cell-mediated HER-2/neu-specific tumor rejection in the absence of B cells. International Journal of Cancer 109:259-264).

The hypothesis is that antibody responses do not differ significantly among treatment groups and do not influence therapeutic outcome. The importance of antibodies by studying the effects of B cell depletion on therapeutic outcome is tested. Reduction of the antibody response to virus may indirectly improve outcome.

The present invention is not to be limited in scope by the specific embodiments described herein. Indeed, various modifications of the invention in addition to those described herein will become apparent to those skilled in the art from the foregoing description and accompanying Figures. Various references are cited herein, the disclosure of which are incorporated by reference in their entireties.

CITED REFERENCES

Balachandran, S., Porosnicu, M., Barber, G. N., 2001. Oncolytic activity of vesicular stomatitis virus is effective against tumors exhibiting aberrant p53, Ras, or myc function and involves the induction of apoptosis. J. Virol. 75, 3474-3479.

Bergman, I., Barmada, M. A., Griffin, J. A., Slamon, D. J., 2001. Treatment of meningeal breast cancer xenografts in the rat using an anti-p185/HER2 antibody. Clin. Cancer Res. 7, 2050-2056.

Bergman, I., Whitaker-Dowling, P., Gao, Y., Griffin, J. A., Watkins, S. C., 2003. Vesicular stomatitis virus expressing a chimeric Sindbis glycoprotein containing an Fc antibody binding domain targets to Her2/neu overexpressing breast cancer cells. Virology 316, 337-347.

Bucheit, A. D., Kumar, S., Grote, D. M., Lin, Y., von, M., Cattaneo, R. B., Fielding, A. K., 2003. An oncolytic measles virus engineered to enter cells through the CD20 antigen. Mol. Ther. 7, 62-72.

de Mattos, C. A., de Mattos, C. C., Rupprecht, C. E., 2001. Rhabdoviruses. In: Knipe, D., Howley, P. (Eds.), Fundamental Virology. Lippincott Williams & Wilkins, Philadelphia, pp. 1245-1277.

Dubuisson, J., Rice, C. M., 1993. Sindbis virus attachment: isolation and characterization of mutants with impaired binding to vertebrate cells. J. Virol. 67, 3363-3374.

Fernandez, M., Porosnicu, M., Markovic, D., Barber, G. N., 2002. Genetically engineered vesicular stomatitis virus in gene therapy: application for treatment of malignant disease. J. Virol. 76, 895-904.

Hammond, A. L., Plemper, R. K., Zhang, J., Schneider, U., Russell, S. J., Cattaneo, R., 2001. Single-chain antibody displayed on a recombinant 610 measles virus confers entry through the tumor-associated carcinoem-bryonic antigen. J. Virol. 75, 2087-2096.

Jiang, A., Chu, T. H., Nocken, F., Cichutek, K., Domburg, R., 1998. Cell-type-specific gene transfer into human cells with retroviral vectors that display single-chain antibodies. J. Virol. 72, 10148-10156.

Jost, C. R., Titus, J. A., Kurucz, I., Segal, D. M., 1996. A single-chain bispecific Fv2 molecule produced in mammalian cells redirects lysis by 617 activated CTL. Mol. Immunol. 33, 211-219.

Khare, P. D., Shao-Xi, L., Kuroki, M., Hirose, Y., Arakawa, F., Nakamura, K., Tomita, Y., Kuroki, M., 2001. Specifically targeted killing of carcinoembryonic antigen (CEA)-expressing cells by a retroviral vector displaying single-chain variable fragmented antibody to CEA and carrying the gene for inducible nitric oxide synthase. Cancer Res. 61, 370-375.

Lawson, N. D., Stillman, E. A., Whitt, M. A., Rose, J. K., 1995. Recombinant vesicular stomatitis viruses from DNA. Proc. Natl. Acad. Sci. U.S.A. 625 92, 4477-4481.

Marin, M., Noel, D., Valsesia-Wittman, S., Brockly, F., Etienne-Julan, M., Russell, S., Cosset, F. L., Piechaczyk, M., 1996. Targeted infection of human cells via major histocompatibility complex class I molecules by Moloney murine leukemia virus-derived viruses displaying single-chain antibody fragment-envelope fusion proteins. J. Virol. 70, 2957-2962.

Martin, F., Chowdhury, S., Neil, S. J., Chester, K. A., Cosset, F. L., Collins, M. K., 2003. Targeted retroviral infection of tumor cells by receptor cooperation. J. Virol. 77, 2753-2756.

Morizono, K., Bristol, G., Xie, Y. M., Kung, S. K., Chen, I. S., 2001. Antibody-directed targeting of retroviral vectors via cell surface antigens. J. Virol. 75, 8016-8020.

Ohno, K., Sawai, K., Iijima, Y., Levin, B., Meruelo, D., 1997. Cell-specific targeting of Sindbis virus vectors displaying IgG-binding domains of 639 protein A. Nat. Biotechnol. 15, 763-767.

Peng, K. W., Donovan, K. A., Schneider, U., Cattaneo, R., Lust, J. A., Russell, S. J., 2003. Oncolytic measles viruses displaying a single-chain antibody against CD38, a myeloma cell marker. Blood 101, 2557-2562.

Phinney, B. S., Blackburn, K., Brown, D. T., 2000. The surface conformation of Sindbis virus glycoproteins E1 and E2 at neutral and low pH, as determined by mass spectrometry-based. mapping. J. Virol. 74, 646 5667-5678.

Ring, C. J., 2002. Cytolytic viruses as potential anti-cancer agents. J. Gen. 648 Virol. 83, 491-502.

Rose, J. K., Whitt, M. A., 2001. Rhabdoviridae: the viruses and their replication. In: Knipe, D., Howley, P. (Eds.), Fundamental Virology. Lippincott Williams & Wilkins, Philadelphia, pp. 1221-1244.

Russell, S. J., 1994. Replicating vectors for cancer therapy: a question of strategy. Semin. Cancer Biol. 5, 437-443.

Sariola, M., Saraste, J., Kuismanen, E., 1995. Communication of post-Golgi elements with early endocytic pathway: regulation of endoproteolytic cleavage of Semliki Forest virus p62 precursor. J. Cell Sci. 108, 2465-2475.

Sawai, K., Meruelo, D., 1998. Cell-specific transfection of choriocarcinoma cells by using Sindbis virus hCG expressing chimeric vector. Biochem. Biophys. Res. Commun. 248, 315-323.

Schnell, M. J., Buonocore, L., Kretzschmar, E., Johnson, E., Rose, J. K., 1996. Foreign glycoproteins expressed from recombinant vesicular stomatitis viruses are incorporated efficiently into virus particles. Proc. Natl. Acad. Sci. U.S.A. 93, 11359-11365.

Schnell, M. J., Johnson, J. E., Buonocore, L., Rose, J. K., 1997. Construction of a novel virus that targets HIV-1-irifected cells and controls HIV-1 infection. Cell 90, 849-857.

Schnell, M. J., Buonocore, L., Boritz, E., Ghosh, H. P., Chernish, R., Rose, J. K., 1998. Requirement for a non-specific glycoprotein cytoplasmic domain sequence to drive efficient budding of vesicular stomatitis virus. EMBO J. 17, 1289-1296.

Slamon, D. J., Leyland-Jones, B., Shak, S., Fuchs, H., Paton, V., Bajamonde, A., Fleming, T., Eiermann, W., Wolter, J., Pegram, M., Baselga, J., Norton, L., 2001. Use of chemotherapy plus a monoclonal antibody against HER2 for metastatic breast cancer that overexpresses 676 HER2. N. Engl. J. Med. 344, 783-792.

Smith, T. J., Cheng, R. H., Olson, N. H., Peterson, P., Chase, E., Kuhn, R. J., Baker, T. S., 1995. Putative receptor binding sites on alphaviruses as visualized by cryoelectron microscopy. Proc. Natl. Acad. Sci. U.S.A. 92, 10648-10652.

Stojdl, D. F., Lichty, B., Knowles, S., Marius, R., Atkins, H., Sonenberg, N., Bell, J. C., 2000. Exploiting tumor-specific defects in the interferon pathway with a previously unknown oncolytic virus. Nat. Med. 6, 821-825.

Watson, D. G., Moehring, J. M., Moehring, T. J., 1991. A mutant CHO-K1 strain with resistance to Pseudomonas exotoxin A and alphaviruses fails to cleave Sindbis virus glycoprotein PE2. J. Virol. 65, 2332-2339.

Wildner, O., 2001. Oncolytic viruses as therapeutic agents. Ann. Med. 33, 291-304.

Yang, Q., Mamounas, M., Yu, G., Kennedy, S., Leaker, B., Merson, J., Wong-Staal, F., Yu, M., Barber, J. R., 1998. Development of novel cell surface CD34-targeted recombinant adeno-associated virus vectors for gene therapy. Hum. Gene Ther. 9, 1929-1937.

Zhang, W., Mukhopadhyay, S., Pletnev, S. V., Baker, T. S., Kuhn, R. J., Rossmann, M. G., 2002. Placement of the structural proteins in Sindbis virus. J. Virol. 76, 11645-11658.

Zwiebel, J. A., 2001. Cancer gene and oncolytic virus therapy. Semin. Oncol. 28, 336-343.

Aarts, W. M., J. Schlom, and J. W. Hodge. 2002. Vector-based vaccinelcytokine combination therapy to enhance induction of immune responses to a self-antigen and antitumor activity. Cancer Res. 62:5770-5777.

Ali, S. A., J. Lynam, C. S. McLean, C. Entwisle, P. Loudon, J. M. Rojas, S. E. McArdle, G. Li, S. Mian, and R. C. Rees. 2002. Tumor regression induced by intratumor therapy with a disabled infectious single cycle (DISC) herpes simplex virus (HSV) vector, DISC/HSV/murine granulocyte-macrophage colony-stimulating factor, correlates with antigen-specific adaptive immunity. Journal of Immunology 168:3512-3519.

Amici, A., A. Smorlesi, G. Noce, G. Santoni, P. Cappelletti, L. Capparuccia, R. Coppari, R. Lucciarini, C. Petrelli, and M. Provinciali. 2000. DNA vaccination with full-length or truncated neu induces protective immunity against the development of spontaneous mammary tumors in HER-2/neu transgenic mice. Gene Therapy 7:703-706.

Bachmann, M. F., U. Kalinke, A. Althage, G. Freer, C. Burkhart, H. Roost, M. Aguet, H. Hengartner, and R. M. Zinkernagel. 1997. The role of antibody concentration and avidity in antiviral protection. Science 276:2024-2027.

Balachandran, S., M. Porosnicu, and G. N. Barber. 2001. Oncolytic activity of vesicular stomatitis virus is effective against tumors exhibiting aberrant p53, Ras, or myc function and involves the induction of apoptosis. Journal of Virology 75:3474-3479.

Beatty, G. and Y. Paterson. 2001. IFN-gamrna-dependent inhibition of tumor angiogenesis by tumor-infiltrating CD4+T cells requires tumor responsiveness to IFN-gamma. Journal of Immunology 166:2276-2282.

Bergman, I., M. Ahdab-Barmada, S. S. Kemp, J. A. Griffin, and N. K. Cheung. 1997. A rat model of leptomeningeal human neoplastic xenografts. J. Neurooncol. 34:221-231.

Bergman, I., E. Arbit, M. Rosenblum, S. M. Larson, G. Heller, and N. K. Cheung. 1993. Treatment of spinal epidural neuroblastoma xenografts in rats using anti-GD2 monoclonal antibody 3F8. J. Neurooncol. 15:235-242.

Bergman, I., M. A. Barmada, J. A. Griffin, and D. J~Slamon. 2001. Treatment of meningeal breast cancer xenografts in the rat using an anti-pI85/HER2 antibody. Clinical Cancer Research 7:2050-2056.

Bergman, I., M. A. Bannada, G.Heller, J. A. Griffin, and N. K. Cheung. 1999. Treatment of neoplastic meningeal xenografts by intraventricular administration of an anti-ganglioside monoclonal antibody, 3F8. International Journal of Cancer 82:538-548.

Bergman, I., P. H. Basse, M. A. Barmada, J. A. Griffin, and N. K. Cheung. 2000. Comparison of in vitro antibody-targeted cytotoxicity using mouse, rat and human effectors. Cancer Immunology & Immunotherapy 49:259-266.

Bergman, I., G. J. Burckart, C. R. PoW, R. Venkataramanan, M. A. Barmada, J. A. Griffin, and N. K. Cheung. 1998. Pharmacokinetics of IgG and IgM anti-ganglioside antibodies in rats and monkeys after intrathecal administration. Journal of Pharmacology & Experimental Therapeutics 284: 111-115.

Bergman, I., C. R. PoW, R. Venkataramanan, G. J. Burckart, M. Stabin, M. A. Barmada, J. A. Grifrm, and N. K. Cheung. 1999. Intrathecal administration of an anti-ganglioside antibody results in specific accumulation with meningeal neoplastic xenografts in nude rats. Journal of Immunotherapy. 22: 114-123.

Bergman, I., P. Whitaker-Dowling, Y. Gao, J. A. Griffin, and S. C. Watkins. 2003. Vesicular stomatitis virus expressing a chimeric Sindbis glycoprotein containing an Fc antibody binding domain targets to Her2/neu overexpressing breast cancer cells. Virology 316:337-347:

Bussfeld, D., M. Nain, P. Hofmann, D. Gemsa, and H. Sprenger. 2000. Selective induction of the monocyte attracting chemokines MCP-1 and IP-10 in vesicular stomatitis virus-infected human monocytes. Journal of Interferon & Cytokine Research 20:615-621.

Buteau, C., S. N. Markovic, and E. Celis. 2002. Challenges in the development of effective peptide vaccines for cancer. [Review] [90 refs]. Mayo Clinic Proceedings 77:339-349.

Cerny, A., C. Heusser, S. Sutter, A. W. Huegin, H. Bazin, H. Hengartner, and R. M. Zinkernagel. 1986. Generation of agammaglobulinaemic mice by prenatal and postnatal exposure to polyclonal or monoclonal anti-IgM antibodies. Scandinavian Journal of Immunology 24:437-445.

Cerny, A., S. Sutter, H. Bazin, H. Hengartner, and R. M. Zinkernagel. 1988. Clearance of lymphocytic choriomeningitis virus in antibody- and B-cell-deprived mice. Journal of Virology 62: 1803-1807.

Chu E and DeVita V T. 2001. Principles of Cancer Management: Chemotherapy, p. 289-306. In H. S. R. S. DeVita V T Jr. (ed.), Cancer: Principles and Practice of Oncology. Lippincott, Williams & Wilkins, Philadelphia.

de Mattos C A, de Mattos C C, and Rupprecht C E. 2001. Rhabdoviruses, p. 1245-1277. In D. Knipe and P. Howley (eds.), Fundamental Virology. Lippincott Williams & Wilkins, Philadelphia.

Dubuisson, J. and C. M. Rice. 1993. Sindbis virus attachment: isolation and characterization of mutants with impaired binding to vertebrate cells. Journal of Virology 67:3363-3374.

Elzey, B. D., D. R. Siemens, T. L. Ratliff, and D. M. Lubaroff. 2001. Immunization with type 5 adenovirus recombinant for a tumor antigen in combination with recombinant canarypox virus (ALVAC) cytokine gene delivery induces destruction of established prostate tumors. International Journal of Cancer 94:842-849.

Ercolini, A. M., J. P. Machiels, Y. C. Chen, J. E. Slansky, M. Giedlen, R. T. Reilly, and E. M. Jaffee. 2003. Identification and characterization of the immunodominant rat HER-2/neu 1/1HC class I epitope presented by spontaneous mammary tumors from HER-2/neu-transgenic mice. Journal of Immunology 170:4273-4280.

Fernandez, M., M. Porosnicu, D. Markovic, and G. N. Barber; 2002. Genetically engineered vesicular stomatitis virus in gene therapy: application for treatment of malignant disease. Journal of Virology 76 :895-904.

Fernandez, M., M. Porosnicu, D. Markovic, and G. N. Barber. 2002. Genetically engineered vesicular stomatitis virus in gene therapy: application for treatment of malignant disease. Journal of Virology 76 :895-904.

Fuchs, E. J. and P. Matzinger. 1996. Is cancer dangerous to the immune system? [Review] [46 refs]. Seminars in Immunology 8:271-280.

Griffith, T. S., M. Kawakita, J. Tian, J. Ritchey, J. Tartaglia, I. Sehgal, T. C. Thompson, W. Zhao, and T. L. Ratliff. 2001. Inhibition of murine prostate tumor growth and activation of immunoregulatory cells with recombinant canarypox viruses. J. Natl. Cancer Inst. 93:998-1007.

Gunn, G. R., A. Zubair, C. Peters, Z. K. Pan, T. C. Wu, and Y. Paterson. 2001. Two Listeria monocytogenes vaccine vectors that express different molecular forms of human papilloma virus-16 (HPV-16) E7 induce qualitatively different T cell immunity that correlates with their ability to induce regression of established tumors immortalized by HPV-16. Journal of Immunology 167:6471-6479.

Guy, C. T., M. A. Webster, M. Schaller, T. J. Parsons, R. D. Cardiff, and W. J. Muller~1992. Expression of the neu protooncogene in the mammary epithelium of transgenic mice induces metastatic disease. Proceedings of the National Academy of Sciences of the United States of America 89: 10578-10582.

Heise, C. C., A. M; Williams, S. Xue, Mi Propst; and 'D. H. Kim; 1999. Intravenous administration of ONYX-015, a selectively replicating adenovirus, induces antitumoral efficacy. Cancer Res. 59:2623-2628.

Hu, H. M., H. Winter, J. Ma, M. Croft, W. J. Urba, and B. A. Fox. 2002. CD28, TNF receptor, and IL-12 are critical for CD4-independent cross-priming of therapeutic antitumor CD8+ T cells. Journal of Immunology 169:4897-4904.

Igarashi, T., T. Ohtsu, H. Fujii, Y. Sasaki, Y. Morishima, M. Ogura, Y. Kagami, T. Kinoshita, M. Kasai, Y. Kiyama, Y. Kobayashi, K. Tobinai, and C. IDEe. 2001. Re-treatment of relapsed indolent B-celllymphoma with rituximab. International Journal of Hematology 73:213-221.

Kalinke, D., E. M. Bucher, B. Ernst, A. Oxenius, H. P. Roost, S. Geley, R. Kofler, R. M. Zinkernagel, and H. Hengartner. 1996. The role of somatic mutation in the generation of the protective humoral immune response against vesicular stomatitis virus. Immunity 5:639-652.

Kim, S. H., J. F. Carew, D. A. Kooby, J. Shields, C. Entwisle, S. Patel, J. P. Shah, and Y. Fong. 2000. Combination gene therapy using multiple immunomodulatory genes transferred by a defective infectious single cycle herpes virus in squamous cell cancer. Cancer Gene Therapy 7:1279-1285.

Lamikanra, A., Z. K. Pan, S. N. Isaacs, T. C. Wu, and Y. Paterson. 2001. Regression of established human papillomavirus type 16 (HPV-16) immortalized tumors in vivo by vaccinia viruses expressing different forms of HPV-16 E7 correlates with enhanced CD8(+) T-cell responses that home to the tumor site. Journal of Virology 75:9654-9664.

Lawson, N. D., E. A. Stillman, M. A. Whitt, and J. K. Rose. 1995. Recombinant vesicular stomatitis viruses from DNA [published erratum appears in Proc Natl Acad Sci USA Sep. 12, 1995; 92(19): 9009]. Proceedings of the National Academy of Sciences of the United States of America 92:4477-4481.

Li, B., J. M. Rosen, J. McMenamin-Balano, W. J. Muller, and A. S. Perkins. 1997. neJ]/ERBB2 cooperates with p53-172H during mammary tumorigenesis in transgenic mice. Molecular & Cellular Biology 17:3155-3163.

Lindencrona, J. A., S. Preiss, T. Kammertoens, T. Schuler, M. Piechocki, W. Z. Wei, B. Seliger, T. Blankenstein, and R. Kiessling. 2004. CD4+ T cell-mediated HER-2/neu-specific tumor rejection in the absence of B cells. International Journal of Cancer 109:259-264.

Lipsky P E and Diamond B. 2001. Autoimmunity and autoimmune diseases, p. 1839-1843. In Brauwald E. Fauci A S, Isselbacher K J, Kasper D L, Hauser S L, Longo D L, and Jameson J L (eds.), Harrison's principles of internal medicine. McGraw-Hill, New York.

Matzinger, P. 1998. An innate sense of danger. [Review] [86 refs]. Seminars in Immunology 10:399-415.

Miller, G., V. G. Pillarisetty, A. B. Shah, S. Lahrs, Z. Xing, and R. P. DeMatteo. 2002. Endogenous granulocyte-macrophage colony-stimulating factor overexpression in vivo results in the long-term recruitment of a distinct dendritic cell population with enhanced immunostimulatory function. Journal of Immunology 169:2875-2885.

Miller, M. A., C. L. Lavine, S. D. Klas, L. M. Pfeffer, and M. A. Whitt. 2004. Recombinant replication-restricted VSV as an expression vector for murine cytokines. Protein Expression & Purification 33:92-103.

Morizono, K., G. Bristol, Y. M. Xie, S. K. Kung, and I. S. Chen. 2001. Antibody-directed targeting of retroviral vectors via cell surface antigens. Journal of Virology 75:8016-8020.

Mwangi, W., W. C. Brown, H. A. Lewin, C. J. Howard, J. C. Hope, T. V! Baszlerj P; Caplazi, J. Abbott, and G. H. Palmer: 2002. DNA-encoded fetal liver tyrosine kinase 3 ligand and granulocyte macrophage-colony stimulating factor increase dendritic cell recruitment to the inoculation site and enhance antigen-specific CD4+. T cell responses induced by DNA vaccination of outbred animals. Journal of Immunology 169:3837-3846.

Ohas W, P. S., S. Oehen, K. Buerki, H. Pircher, C. T. OhasW, B. Odermatt, B. Malissen, R. M. Zinkernagel, and H. Hengartner. 1991. Ablation of "tolerance" and induction of diabetes by virus infection in viral antigen transgenic mice. Cell 65:305-317.

Ohno, K., K. Sawai, Y. Iijima, B. Levin, and D. Meruelo. 1997. Cell-specific targeting of Sindbis virus vectors displaying IgG-binding domains of protein A. Nature Biotechnology 15:763-767.

Parker, J. N., G. Y. Gillespie, C. E. Love, S. Randall, R. J. Whitley, and J. M. Markert. 2000. Engineered herpes simplex virus expressing IL-12 in the treatment of experimental murine brain tumors. Proceedings of the National Academy of Sciences of the United States of America 97:2208-2213.

Penichet, M. L., P. M. Challita, S. U. SWn, S. L. Sampogna, J. D. Rosenblatt, Morrison, and S L. 1999. In vivo properties of three human HER2/neu-expressing murine cell lines in immunocompetent mice. Laboratory Animal Science 49: 179-188.

Perez-Diez, A., P. J. Spiess, N. P. Restifo, P. Matzinger, and F. M. Marincola. 2002. Intensity of the vaccine elicited immune response determines tumor clearance. Journal of Immunology 168:338-347.

Phan, G. Q., P. Attia, S. M. Steinberg, D. E. White, and S. A. Rosenberg. 2001. Factors associated with response to high-dose interleukin-2 in patients with metastatic melanoma. J. Clin. Oncol. 19:3477-3482.

Pilon, S. A., M. P. Piechocki, and W. Z. Wei. 2001. Vaccination with cytoplasmic ErbB-2 DNA protects mice from mammary tumor growth without anti-ErbB-2 antibody. Journal of Immunology 167:3201-3206.

Pu, Z., J. A. Carrero, and E. R. Unanue. 2002. Distinct recognition by two subsets of T cells of an MHC class peptide complex. Proceedings of the National Academy of Sciences of the United States of America 99:8844-8849.

Putzer, B. M., T. Stiewe, F. Rodicker, O~ScWldgen, S. Ruhm, O. Dirsch, M. Fiedler, U. Damen, B. Tennant, C. Scherer, F. L. Graham, and M. Roggendorf. 2001. Large nontransplanted hepatocellular carcinoma in woodchucks: treatment with adenovirus-mediated delivery of interleukiri 121B7.1 genes. J. NatL Cancer Inst. 93:472-479.

Qin, H. and S. K. Chatterjee. 1996. Cancer gene therapy using tumor cells infected with recombinant vaccinia virus expressing GM-CSF. Human Gene Therapy 7:1853-1860.

Quinones-Kochs, M. I., M. J. Schnell, L. Buonocore, and J. K. Rose. 2001. Mechanisms of loss of foreign gene expression in recombinant vesicular stomatitis viruses. Virology 287:427-435.

Reilly, R. T., J. P. Machiels, L. A. Emens, A. M. Ercolini, F. I. Okoye, R. Y. Lei, D. Weintraub, and E. M. Jaffee. 2001. The collaboration of both humoral and cellular HER-2/neu7targeted immune responses is required for the complete eradication of HER-2/neu-expressing tumors. Cancer Res. 61:880-883.

Rose J K and Whitt M A. 2001. Rhabdoviridae: The Viruses and Their Replication, p. 1221-1244. /n D. Knipe and P. Howley (eds.), Fundamental Virology. Lippincott Williams & Wilkins, Philadelphia.

Rosenfeld, M. R., I. Bergman, L. Schramm, J. A. Griffin, M. G. Kaplitt, and P. I. Meneses. 1997. Adeno associated viral vector gene transfer into leptomeningeal xenografts. J. Neurooncol. 34:139-144.

Sawai, K and D. Meruelo 1998. Cell-specific transfection choriocarcinoma cells by using Sindbis virus hCG expressing chimeric vector. Biochemical & Biophysical Research Communications 248:315-323.

Schnell, M: J, L. Buonocore, E. Kretzschmar, E. Johnson, andj: K. Rose; 1996. Foreign glycoproteins expressed from recombinant vesicular stomatitis viruses are incorporated efficiently into virus particles. Proceedings of the National Academy of Sciences of the United States of America 93:11359-11365. Schnell, M. J., L. Buonocore, M. A. Whitt, and J. K. Rose. 1996. The minimal conserved transcription stop-start signal promotes stable expression of a foreign gene in vesicular stomatitis virus. Journal of Virology 70:2318-2323.

Shankaran, V., H. Ikeda, A. T. Bruce, J. M. White, P. E. Swanson, L. J. Old, and R. D. Schreiber. 2001. IFNgamma and lymphocytes prevent primary tumour development and shape tumour immunogenicity. Nature 410 :1107-1111.

Stern, B. V., B. O. Boehm, and M. Tary-Lehmann. 2002. Vaccination with tumor peptide in CpG adjuvant protects via IFN-gamma-dependent CD4 cell immunity. Journal of Immunology 168:6099-6105.

Toda, M., S. D. Rabkin, H. Kojima, and R. L. Martuza. 1999. Herpes simplex virus as an in situ cancer vaccine for the induction of specific anti-tumor immunity. Human Gene Therapy 10:385-393.

Wu, J. T., H. M. Byrne, D. H. Kirn, and L. M. Wein. 2001. Modeling and analysis of a virus that replicates selectively in tumor cells. Bulletin of Mathematical Biology 63:731-768.

Yamazaki, M., R. Zhang, F. H. Straus, M. Messina, B. G. Robinson, K. Hashizume, and L. J. DeGroot. 2002. Effective gene therapy for medullary thyroid carcinoma using recombinant adenovirus inducing tumor-specific expression of interleukin-12. Gene Therapy 9:64-74.

Yang, Y. A., O. Dukhanina, B. Tang, M. Mamura, J. J. Letterio, J. MacGregor, S. C. Patel, S. Kbozin, Z. Y. Liu, J. Green, M. R. Anver, G. Merlino, and L. M. Wakefield. 2002. Life~ime exposure to a soluble TGF-beta antagonist protects mice against metastasis without adverse side effects.[comment]. Journal of Clinical Investigation 109: 1607-1615.

Zelazny, E., B. Li, A. M. Anagnostopoulos, A. Coleman, and A. S. Perkins. 2001. Cooperating oncogenic events in murine mammary tumorigenesis: assessment of ErbB2, mutant p53, and mouse mammary tumor virus. Experimental & Molecular Pathology 70: 183-193.

Zhou, H., W. D. Chen, X. Qin, K. Lee, L. Liu, S. D. Markowitz, andS. L. Gerson. 2001. MMTV promoter hypomethylation is linked to spontaneous and MNU associated c-neu expression and mammary carcinogenesis in MMTV c-neu transgenic mice. Oncogene 20:6009-6017.

Balachandran, S. and Barber, G. N. 2000. Vesicular stomatitis virus (VSV) therapy of tumors. *Iubmb Life* 50, 135-138.

Balachandran, S., Porosnicu, M., and Barber, G. N. 2001a. Oncolytic activity of vesicular stomatitis virus is effective against tumors exhibiting aberrant p53, Ras, or myc function and involves the induction of apoptosis. *Journal of Virology* 75, 3474-3479.

Balachandran, S., Porosnicu, M., and Barber, G. N. 2001b. Oncolytic activity of vesicular stomatitis virus is effective against tumors exhibiting aberrant p53, Ras, or myc function and involves the induction of apoptosis. *Journal of Virology* 75, 3474-3479.

Balachandran, S., Roberts, P. C., Kipperman, T., Bhalla, K. N., Compans, R. W., Archer, D. R., and Barber, G. N. 2000. Alpha/beta interferons potentiate virus-induced apoptosis through activation of the FADD/Caspase-8death signaling pathway. *Journal of Virology* 74, 1513-1523.

Bergman, I., Arbit, E., Rosenblum, M., Larson, S. M., Heller, G., and Cheung, N. K. 1993. Treatment of spinal epidural neuroblastoma xenografts in rats using anti-GD2 monoclonal antibody 3F8. *Journal of Neuro-Oncology* 15, 235-242.

Bergman, I., Barmada, M. A., Heller, G., Griffin, J. A., and Cheung, N. K. 1999. Treatment of neoplastic meningeal xenografts by intraventricular administration of an anti-ganglioside monoclonal antibody, 3F8. *International Journal of Cancer* 82, 538-548.

Chan, R., Muller, W. J., and Siegel, P. M. 1999. Oncogenic activating mutations in the neu/erbB-2 oncogene are involved in the induction of mammary tumors. [Review] [34 refs]. *Annals of the New York Academy of Sciences* 889, 45-51.

Chew, H. K. 2002. Medical management of breast cancer: today and tomorrow. [Review] [75 refs]. *Cancer Biotherapy & Radiopharmaceuticals* 17, 137-149.

Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J. 1999. Multinational study of the efficacy and safety of humanized anti-HER2 monoclonal antibody in women who have HER2-overexpressing metastatic breast cancer that has progressed after chemotherapy for metastatic disease. *Journal of Clinical Oncology* 17, 2639-2648.

Danova, M., Porta, C., Ferrari, S., and Riccardi, A. 2001. Strategies of medical treatment for metastatic breast cancer (Review). [Review] [64 refs]. *International Journal of Oncology* 19, 733-739.

Fernandez, M., Porosnicu, M., Markovic, D., and Barber, G. N. 2002. Genetically engineered vesicular stomatitis virus in gene therapy: application for treatment of malignant disease. *Journal of Virology* 76, 895-904.

Hindle, W. 2002. Breast cancer: introduction. [Review] [33 refs]. *Clinical Obstetrics & Gynecology* 45, 738-745.

Kahn, J. S., Schnell, M. J., Buonocore, L., and Rose, J. K. 1999. Recombinant vesicular stomatitis virus expressing respiratory syncytial virus (RSV) glycoproteins: RSV fusion protein can mediate infection and cell fusion. *Virology* 254, 81-91.

Kern, J. A., Schwartz, D. A., Nordberg, J. E., Weiner, D. B., Greene, M. I., Torney, L., and Robinson, R. A. 1990. p185 neu expression in human lung adenocarcinomas predicts shortened survival. *Cancer Research* 50, 5184-5187.

Nemunaitis, J., Cunningham, C., Tong, A. W., Post, L., Netto, G., Paulson, A. S., Rich, D., Blackburn, A., Sands, B., Gibson, B., Randlev, B., and Freeman, S. 2003. Pilot trial of intravenous infusion of a replication-selective adenovirus (ONYX-015) in combination with chemotherapy or IL-2 treatment in refractory cancer patients. *Cancer Gene Therapy* 10, 341-352.

Niehans, G. A., Singleton, T. P., Dykoski, D., and Kiang, D. T. 1993. Stability of HER-2/neu expression over time and at multiple metastatic sites. *Journal of the National Cancer Institute* 85, 1230-1235.

Pegram, M. D., Lipton, A., Hayes, D. F., Weber, B. L., Baselga, J. M., Tripathy, D., Baly, D., Baughman, S. A., Twaddell, T., Glaspy, J. A., and Slamon, D. J. 1998. PHASE II STUDY OF RECEPTOR-ENHANCED CHEMOSENSITIVITY USING RECOMBINANT HUMANIZED ANTI-P185(HER2/NEU) MONOCLONAL ANTIBODY PLUS CISPLATIN IN PATIENTS WITH HER2NEU-OVEREXPRESSING METASTATIC BREAST CANCER REFRACTORY TO CHEMOTHERAPY TREATMENT. *Journal of Clinical Oncology* 16, 2659-2671.

Plakhov, I. V., Arlund, E. E., Aoki, C., and Reiss, C. S. 1995. The earliest events in vesicular stomatitis virus infection of the murine olfactory neuroepithelium and entry of the central nervous system. *Virology* 209, 257-262.

Press, M. F., Cordon-Cardo, C., and Slamon, D. J. 1990. Expression of the HER-2/neu proto-oncogene in normal human adult and fetal tissues. *Oncogene* 5, 953-962.

Press, M. F., Pike, M. C., Hung, G., Zhou, J. Y., Ma, Y., George, J., Dietz-Band, J., James, W., Slamon, D. J., Batsakis, J. G., and et al. 1994. Amplification and overexpression of HER-2/neu in carcinomas of the salivary gland: correlation with poor prognosis. *Cancer Research* 54, 5675-5682.

Reilly, R. T., Gottlieb, M. B., Ercolini, A. M., Machiels, J. P., Kane, C. E., Okoye, F. I., Muller, W. J., Dixon, K. H., and Jaffee, E. M. 2000. HER-2/neu is a tumor rejection target in tolerized HER-2/neu transgenic mice. *Cancer Research* 60, 3569-3576.

Ring, C. J. 2002. Cytolytic viruses as potential anti-cancer agents. [Review] [159 refs]. *Journal of General Virology* 83, 491-502.

Rott, O., Herzog, S., and Cash, E. 1994. Autoimmunity caused by host cell protein-containing viruses. *Medical Microbiology & Immunology* 183, 195-204.

Russell, S. J. 1994. Replicating vectors for gene therapy of cancer: risks, limitations and prospects. [Review]. *European Journal of Cancer* 30A, 1165-1171.

Schnell, M. J., Buonocore, L., Boritz, E., Ghosh, H. P., Chemish, R., and Rose, J. K. 1998. Requirement for a non-specific glycoprotein cytoplasmic domain sequence to drive efficient budding of vesicular stomatitis virus. *EMBO Journal* 17, 1289-1296.

Schnell, M. J., Buonocore, L., Kretzschmar, E., Johnson, E., and Rose, J. K. 1996a. Foreign glycoproteins expressed from recombinant vesicular stomatitis viruses are incorporated efficiently into virus particles. *Proceedings of the National Academy of Sciences of the United States of America* 93, 11359-11365.

Schnell, M. J., Buonocore, L., Whitt, M. A., and Rose, J. K. 1996b. The minimal conserved transcription stop-start signal promotes stable expression of a foreign gene in vesicular stomatitis virus. *Journal of Virology* 70, 2318-2323.

Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. 2001. Use of chemotherapy plus a monoclonal antibody against HER2 for metastatic breast cancer that overexpresses HER2. [comment]. *New England Journal of Medicine* 344, 783-792.

Stojdl, D. F., Lichty, B., Knowles, S., Marius, R., Atkins, H., Sonenberg, N., and Bell, J. C. 2000. Exploiting tumor-specific defects in the interferon pathway with a previously unknown oncolytic virus. *Nature Medicine* 6, 821-825.

Stojdl, D. F., Lichty, B. D., tenOever, B. R., Paterson, J. M., Power, A. T., Knowles, S., Marius, R., Reynard, J., Poliquin, L., Atkins, H., Brown, E. G., Durbin, R. K., Durbin, J. E., Hiscott, J., and Bell, J. C. 2003a. VSV strains with defects in their ability to shutdown innate immunity are potent systemic anti-cancer agents. *Cancer Cell* 4, 263-275.

Stojdl, D. F., Lichty, B. D., tenOever, B. R., Paterson, J. M., Power, A. T., Knowles, S., Marius, R., Reynard, J., Poliquin, L., Atkins, H., Brown, E. G., Durbin, R. K., Durbin, J. E., Hiscott, J., and Bell, J. C. 2003b. VSV strains with defects in their ability to shutdown innate immunity are potent systemic anti-cancer agents. *Cancer Cell* 4, 263-275.

Tyler, K L. and Nathanson, N. (2001). Pathogenesis of Viral Infections. In "Fundamental Virology" (D. Knipe and P. Howley, Eds.), pp. 199-244. Lippincott Williams & Wilkins, Philadelphia.

Vassalli, J. D., Lombardi, T., Wohlwend, A., Montesano, R., and Orci, L. 1986. Direct cell-to-cell transmission of vesicular stomatitis virus. *Journal of Cell Science* 85, 125-131.

Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., Shak, S., Stewart, S. J., and Press, M. 2002. Efficacy and safety of trastuzumab as a single agent in first-line treatment of HER2-overexpressing metastatic breast cancer. *Journal of Clinical Oncology* 20, 719-726.

Wu, J. T., Byrne, H. M., Kirn, D. H., and Wein, L. M. 2001. Modeling and analysis of a virus that replicates selectively in tumor cells. *Bulletin of Mathematical Biology* 63, 731-768.

Zelazny, E., Li, B., Anagnostopoulos, A. M., Coleman, A., and Perkins, A. S. 2001. Cooperating oncogenic events in murine mammary tumorigenesis: assessment of ErbB2, mutant p53, and mouse mammary tumor virus. *Experimental & Molecular Pathology* 70, 183-193.

---

We claim:

1. An isolated recombinant vesicular stomatitis virus for producing a cytolytic effect in a target cell comprising (i) a modified Sindbis virus E2 protein replacing the G protein of vesicular stomatitis virus at the viral surface, where the modification decreases infectivity of the virus toward a cell that is not a target cell; and (ii) a single chain antibody that binds to an antigen present on a target cell.

2. The recombinant virus of claim 1, wherein the modification of the Sindbis virus E2 protein is an insertion, deletion, or substitution of one or more amino acid residues at positions selected from the group consisting of position 69, 70, 71, 72, 73, 74, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 21 and 260.

3. The recombinant virus of claim 1, wherein the single chain antibody binds to an antigen selected from the group consisting of HER2/neu, EphA3, EGFR, CD4, CD8, CD20, MAGE, BAGE, GAGE, NY-ESO-1, TRP2, gp100, Melan-A/MART1, ganglioside and PSMA.

4. The recombinant virus of claim 2, wherein the single chain antibody binds to an antigen selected from the group consisting of HER2/neu, EphA3, EGFR, CD4, CD8, CD20, MAGE, BAGE, GAGE, NY-ESO-1, TRP2, gp100, Melan-A/MART1, ganglioside and PSMA.

5. The recombinant virus of claim 1, further comprising, in expressible form, a gene encoding a protein selected from the group consisting of GM-CSF, interleukin-12, interferon beta, interferon gamma, interleukin-10, urokinase, tumor necrosis factor-α, interleukin-4, herpesvirus thymidine kinase, purine nucleoside phosphorylase, cytosine deaminase, and EGFP.

6. The recombinant virus of claim 2, further comprising, in expressible form, a gene encoding a protein selected from the group consisting of GM-CSF, interleukin-12, interferon beta, interferon gamma, interleukin-10, urokinase, tumor necrosis factor-α, interleukin-4, herpesyirus thymidine kinase, purine nucleoside phosphorylase, cytosine deaminase, and EGFP.

7. The recombinant virus of claim 3, further comprising, in expressible form, a gene encoding a protein selected from the group consisting of GM-CSF, interleukin-12, interferon beta, interferon gamma, interleukin-10, urokinase, tumor necrosis factor-α, interleukin-4, herpesyirus thymidine kinase, purine nucleoside phosphorylase, cytosine deaminase, and EGFP.

* * * * *